US007078487B2

(12) United States Patent
Jüppner et al.

(10) Patent No.: US 7,078,487 B2
(45) Date of Patent: Jul. 18, 2006

(54) PTH1R RECEPTORS

(75) Inventors: Harald Jüppner, Cambridge, MA (US); David A Rubin, Needham, MA (US)

(73) Assignee: The General Hospital Corporation, Boston, MA (US)

( * ) Notice: Subject to any disclaimer, the term of this patent is extended or adjusted under 35 U.S.C. 154(b) by 73 days.

(21) Appl. No.: 10/372,095

(22) Filed: Feb. 25, 2003

(65) Prior Publication Data

US 2003/0162256 A1    Aug. 28, 2003

Related U.S. Application Data

(62) Division of application No. 09/449,632, filed on Nov. 30, 1999, now Pat. No. 6,451,220.

(60) Provisional application No. 60/110,467, filed on Nov. 30, 1998.

(51) Int. Cl.
*C07K 14/72* (2006.01)
*C07K 14/435* (2006.01)

(52) U.S. Cl. ...................... 530/350; 530/399

(58) Field of Classification Search ............ 530/350, 530/300
See application file for complete search history.

(56) References Cited

U.S. PATENT DOCUMENTS

| 4,423,037 A | 12/1983 | Rosenblatt et al. |
| 5,010,010 A | 4/1991 | Gautvik et al. |
| 5,208,041 A | 5/1993 | Sindrey |
| 5,496,801 A | 3/1996 | Holthuis et al. |
| 5,616,560 A | 4/1997 | Geddes et al. |
| 5,693,616 A | 12/1997 | Krstenansky et al. |
| 5,695,955 A | 12/1997 | Krstenansky et al. |
| 5,798,225 A | 8/1998 | Krstenansky et al. |
| 5,814,603 A | 9/1998 | Oldenburg et al. |
| 6,417,333 B1 | 7/2002 | Bringhurst et al. |
| 6,495,662 B1 | 12/2002 | Gardella et al. |
| 6,537,965 B1 | 3/2003 | Bringhurst et al. |
| 6,541,220 B1 | 4/2003 | Juppner et al. |

FOREIGN PATENT DOCUMENTS

| WO | WO 92/01810 A1 | 2/1992 |
| WO | WO 92/17602 A1 | 10/1992 |
| WO | WO 01/23427 A1 | 4/2001 |

OTHER PUBLICATIONS

Bergwitz, C., et al., "Residues in the Membrane-spanning and Extracellular Loop Regions of the Parathyroid Hormone (PTH) -2 Receptor Determine Signaling Selectivity for PTH and PTH-related Peptide," *J. Biol. Chem. 272*:28861-28868, The American Society for Biochemistry and Molecular Biology, Inc. (Nov. 1997).

Bergwitz, C., et al., "Identification, Functional Characterization, and Developmental Expression of Two Nonallelic Parathyroid Hormone (PTH)/PTH-Related Peptide Receptor Isoforms in Xenopus laevis (Daudin)," *Endocrinol.139*:723-732, The Endocrine Society (Feb. 1998).

Bettoun, J.D., et al., "Cloning and Characterization of the Promoter Regions of the Human Parathyroid Hormone (PTH)/PTH-Related Peptide Receptor Gene: Analysis of Deoxyribonucleic Acid from Normal Subjects and Patients with Pseudohypoparathyroidism Type 1b," *J. Clin. Endocrinol. Metab. 82*:1031-1040, The Endocrine Society (Apr. 1997).

Bettoun, J.D., et al., "Developmental Upregulation of Human Parathyroid Hormone (PTH)/PTH-related Peptide Receptor Gene Expression from Conserved and Human-specific Promoters," *J. Clin. Invest. 102*:958-967, The American Society for Clinical Investigation, Inc. (Sep. 1998).

Broadus, A.E., and Stewart, A.F., "Parathyroid Hormone-Related Protein," in *The Parathyroids*, Bilezikian, J.P., ed., Raven Press, Ltd., New York, NY, pp. 259-294 (1994).

Gaich, G., et al., "Amino-Terminal Parathyroid Hormone-Related Protein: Specific Binding and Cytosolic Calcium Responses in Rat Insulinoma Cells," *Endocrinol. 132*:1402-1409, The Endocrine Society (1993).

(Continued)

*Primary Examiner*—Ruixiang Li
(74) *Attorney, Agent, or Firm*—Sterne, Kessler, Goldstein & Fox P.L.L.C.

(57) ABSTRACT

The present invention relates to novel parathyroid hormone (PTH) and parathyroid hormone related protein (PTHrP) receptors (PTH1R and PTH3R) isolated from zebrafish. The receptors of the present invention share homology with previously identified parathyroid hormone (PTH)/parathyroid related protein (PTHrP) receptors. Isolated nucleic acid molecules are provided encoding the zebrafish PTH1R and PTH3R receptors. PTH1R and PTH3R receptor polypeptides are also provided, as are vectors, host cells and recombinant methods for producing the same. The invention further relates to screening methods for identifying agonists and antagonists of PTH1R and PTH3R receptor activity and to diagnostic and therapeutic methods.

7 Claims, 18 Drawing Sheets

OTHER PUBLICATIONS

Gardella, T.J., et al., "Converting Parathyroid Hormone-related Peptide (PTHrP) into a Potent PTH-2 Receptor Agonist," *J. Biol. Chem.* 271:19888-19893, The American Society for Biochemistry and Molecular Biology, Inc. (1996).

Iida-Klein, A., et al., "Truncation of the Carboxyl-terminal Region of the Rat Parathyroid Hormone (PTH)/PTH-related Peptide Receptor Enhances PTH Stimulation of Adenylyl Cyclase but Not Phospholipase C," *J. Biol. Chem.* 270:8458-8465, The American Society for Biochemistry and Molecular Biology, Inc. (1995).

Iida-Klein, A., et al., "Structural Requirements of Parathyroid Hormone/Parathyroid Hormone-Related Peptide Receptors for Phospholipase C Activation and Regulation of Phosphate Uptake," *Miner. Electrolyte Metab.* 21:177-179, S. Karger Medical and Scientific Publishers (1995).

Inomata, N., et al., "Characterization of a Novel Parathyroid Hormone (PTH) Receptor with Specificity for the Carboxyl-Terminal Region of PTH- (1-84)," *Endocrinol.* 136:4732-4740, The Endocrine Society (1995).

Jing, S., et al., "GDNF-Induced Activation of the Ret Protein Tyrosine Kinase Is Mediated by GDNFR-α, a Novel Receptor for GDNF," *Cell* 85:1113-1124, Cell Press (1996).

Joun, H., et al., "Tissue-Specific Transcription Start Sites and Alternative Splicing of the Parathyroid Hormone (PTH)/PTH-Related Peptide (PTHrP) Receptor Gene: A New PTH/PTHrP Receptor Splice Variant that Lacks the Signal Peptide," *Endocrinol.* 138:1742-1749, The Endocrine Society (Apr. 1997).

Jüppner, H., et al., "A G Protein-Linked Receptor for Parathyroid Hormone and Parathyroid Hormone-Related Peptide," *Science* 254:1024-1026, American Association for the Advancement of Science (1991).

Karaplis, A.C., et al., "Lethal skeletal dysplasia from targeted disruption of the parathyroid hormone-related peptide gene," *Genes & Devel.* 8:277-289, Cold Spring Harbor Laboratory Press (1994).

Kong, X.-F., et al., "The Rat, Mouse and Human Genes Encoding the Receptor for Parathyroid Hormone and Parathyroid Hormone-related Peptide are Highly Homologous," *Biochem. Biophys. Res. Comm.* 200:1290-1299, Academic Press, Inc. (1994).

Kovacs, C.S., et al., "Parathyroid hormone-related peptide (PTHrP) regulates fetal-placental calcium transport through a receptor distinct from the PTH/PTHrP receptor," *Proc. Natl. Acad. Sci. USA* 93:15233-15238, National Academy Press (1996).

Lanske, B., et al., "PTH/PTHrP Receptor in Early Development and Indian Hedgehog-Regulated Bone Growth," *Science* 273:663-666, American Association for the Advancement of Science (1996).

Lee, C., et al., "Role of the Extracellular Regions of the Parathyroid Hormone (PTH)/PTH-Related Peptide Receptor in Hormone Binding," *Endocrin.* 135:1488-1495, The Endocrine Society (1994).

McCuaig, K.A., et al., "Molecular cloning of the gene encoding the mouse parathyroid hormone/parathyroid hormone-related peptide receptor," *Proc. Natl. Acad. Sci. USA* 91:5051-5055, National Academy Press (1994).

Mikayama, T., et al., "Molecular cloning and functional expression of a cDNA encoding glycosylation-inhibiting factor," *Proc. Natl. Acad. Sci. USA* 90:10056-10060, National Academy Press (1993).

Orloff, J.J., et al., "Analysis of PTHRP binding and signal transduction mechanisms in benign and malignant squamous cells," *Amer. J. Physiol.* 262:E599-E607, American Physiological Society (1992).

Orloff, J.J., et al., "A Midregion Parathyroid Hormone-Related Peptide Mobilizes Cytosolic Calcium and Stimulates Formation of Inositol Triphosphate in a Squamous Carcinoma Cell Line," *Endocrinol.* 137:5376-5385, The Endocrine Society (1996).

Orloff, J.J., et al., "Further Evidence for a Novel Receptor for Amino-Terminal Parathyroid Hormone-Related Protein on Keratinocytes and Squamous Carcinoma Cell Lines," *Endocrinol.* 136:3016-3023, The Endocrine Society (1995).

Potts, Jr., J.T., and Jüppner, H., "Parathyroid Hormone and Parathyroid Hormone-Related Peptide in Calcium Homeostasis, Bone Metabolism, and Bone Development: The Proteins, Their Genes, and Receptors," in *Metabolic Bone Disease*, 3rd Edition, Avioli, L.V., and Krane, S.M., eds.,Academic Press, San Diego, CA, pp. 51-94 (1998).

Rieger, R., et al., Glossary of Genetics and Cytogenetics, 4th ed., Springer-Verlag, Berlin, German Democratic Republic, pp. 16-19 (1976).

Rubin, D.A., et al., "Molecular Cloning and Expression of Receptors for Parathyroid Hormone (PTH) and PTH-Related (PTHrP) Protein in Zebrafish," *Am. Zoologist* 36:97A, Abstract No. 373, Society for Integrative and Comparative Biology (1996).

Rubin, D.A., and Jüppner, H., "Parathyroid Hormone (PTH)/PTH-Related (PTHRP) Receptor Cloning and in Situ Hybridization in the Zebrafish, Danio Rerio," *Am. Zoologoist* 37:181A, Abstract No. 651, Society for Integrative and Comparative Biology (Dec. 1997).

Rubin, D.A., et al., "Molecular Cloning of a Zebrafish cDNA Encoding a Novel Parathyroid Hormone (PTH)/PTH-related Protein (PTHrP) Receptor (PPR)," *Bone* 23:S255, Abstract No. T224, Elsevier Science (Nov. 1998).

Rubin, D.A., and Jüppner, H., "Zebrafish Express the Common Parathyroid Hormone/Parathyroid Hormone-related Peptide Receptor (PTH1R) and a Novel Receptor (PTH3R) That Is Preferentially Activated by Mammalian and Fugufish Parathyroid Hormone-related Peptide," *J. Biol. Chem.* 274:28185-28190, The American Society for Biochemistry and Molecular Biology, Inc. (Oct. 1999).

Schipani, E., et al., "Identical Complementary Deoxyribonucleic Acids Encode a Human Renal and Bone Parathyroid Hormone (PTH)/PTH-Related Peptide Receptor," *Endocrinol.* 132:2157-2165, The Endocrine Society (1993).

Schipani, E., et al., "Pseudohypoparathyroidism Type Ib Is not Caused by Mutations in the Coding Exons of the Human Parathyroid Hormone (PTH)/PTH-Related Peptide Receptor Gene," *J. Clin. Endocrinol. Metab.* 80:1611-1621, The Endocrine Society (1995).

Sutcliffe, J.G., et al., "Antibodies That React with Predetermined Sites on Proteins," *Science* 219:660-666, American Association for the Advancement of Science (1983).

Takasu, H., et al., "The 69-84 Amino Acid Region of the Parathyroid Hormone Molecule Is Essential for the Interaction of the Hormone with the Binding Sites with Carboxyl-Terminal Specificity," *Endocrinol.* 137:5537-5543, The Endocrine Society (1996).

Takasu, H., and Bringhurst, F.R., "Type-1 Parathyroid Hormone (PTH)/PTH-Related Peptide (PTHrP) Receptors Activate Phospholipase C in Response to Carboxyl-Truncated Analogs of PTH(1-34)," *Endocrinol. 139*:4293-4299, The Endocrine Society (Oct. 1998).

Takasu, H., et al., "Human PTH/PTHrP receptors and Type-2 PTH Receptors Show Discordant Selectivity for Human PTH Analogs with Amino-Terminal Modifications," *Bone 23*:S255, Abstract No. T223, Elsevier Science (Nov. 1998).

Treanor, J.J.S., et al., "Characterization of a multicomponent receptor for GDNF," *Nature 382*:80-83, Nature Publishing Group (1996).

Turner, P.R., et al., "Transmembrane Residues Together with the Amino Terminus Limit the Response of the Parathyroid Hormone (PTH) 2 Receptor to PTH-related Peptide," *J. Biol. Chem. 273*:3830-3837, The American Society for Biochemistry and Molecular Biology, Inc. (Feb. 1998).

Voet, D., and Voet, J.G., *Biochemistry*. John Wiley & Sons, Inc. pp. 126-128, 228-234 (1990).

Wu, T.L., et al., "Structural and Physiologic Characterization of the Mid-region Secretory Species of Parathyroid Hormone-related Protein," *J. Biol. Chem. 271*:24371-24381, The American Society for Biochemistry and Molecular Biology, Inc. (1996).

Yamamoto, S., et al., "Parathyroid Hormone-Related Peptide- (1-34) [PTHrP- (1-34)] Induces Vasopressin Release from the Rat Supraoptic Nucleus in Vitro through a Novel Receptor Distinct from a Type I or Type II PTH/PTHrP Receptor," *Endocrinol. 138*:2066-2072, The Endocrine Society (May 1997).

Yamamoto, S., et al., "Centrally Administered Parathyroid Hormone (PTH)-Related Protein (1-34) But Not PTH(1-34) Stimulates Arginine-Vasopressin Secretion and Its Messenger Ribonucleic Acid Expression in Supraoptic Nucleus of the Conscious Rats," *Endocrinol. 138*:383-388, The Endocrine Society (Jan. 1998).

International Search Report for International Application No. PCT/US99/28207, mailed Apr. 18, 2000.

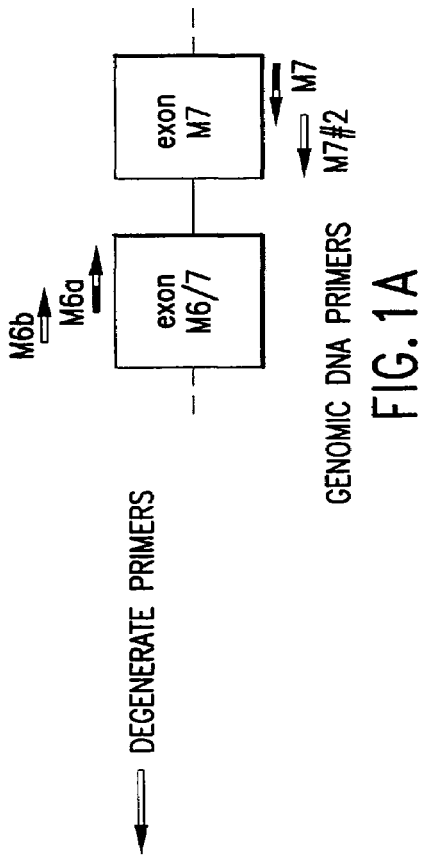
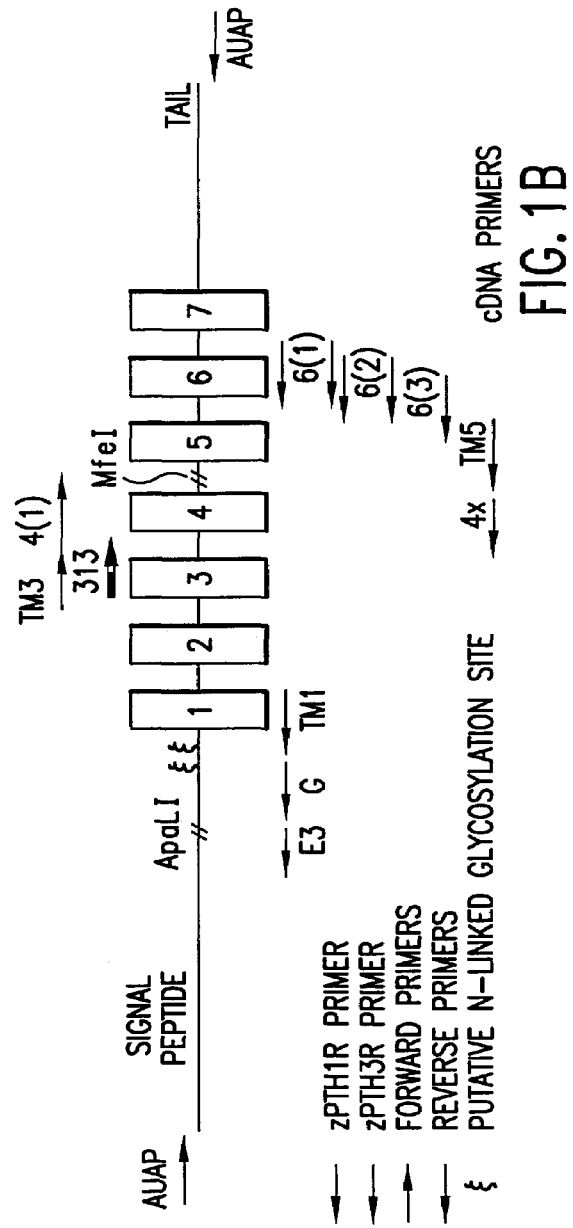

```
   1 TTCTCTCCAA TCGACGCGAC TGCCATGTCC TGAAGAGAAA CAGGAGCTCT
  51 CTGGAGAGCA GGAGTTCTGG AAAAGGTCAA AGGTCCTGGG TTAAGCATGG
 101 TGTCAGTGGA GGTCTCTGTG GCTTTAGTGC TGTGCTGTGT TTTGATGGGA
 151 GCCAGAGCTC TGATTGATTC AGATGATGTC ATCACAAGAG ATGAACAGAT
 201 CTTTCTCCTC ATTGGTGCGC GGTCGAGGTG TGAGAGAACC ATCCGTGCAC
 251 AGTCAGACGT GGTCAGAGAG AATAACTGCG CTCCTGAGTG GGATGGGATC
 301 ATTTGCTGGC CCACAGGAAA ACCCAATCAG ATGGTGGCAG TTCTGTGTCC
 351 TGAGTACATC TATGACTTCA ACCACAGAGG ATACGCGTAT CGACACTGTG
 401 ATGCATCAGG TAACTGGGAG CAGGTGTCCA TTATAAACCG GACGTGGGCA
 451 AACTACACGG AATGCACCAC TTACCTGCAC ACCAACCACA GTGATCAGGA
 501 GGAAGTGTTT GAGCGCCTTT ACCTCATGTA CACTATTGGA TACTCCATAT
 551 CACTGGCAGC GTTACTGGTG GCGGTCTCTA TCCTTTGCTA TTTCAAACGT
 601 CTCCACTGCA CTCGTAACTA CATCCACATC CACCTCTTCA CCTCGTTCAT
 651 ATGTCGAGCA ATCAGTATTT TTGTGAAAGA CGCCGTTCTT TACGCCGTCA
 701 CGAATGATGG AGAACTAGAA GATGGGGCAG TGGAACAAAG ACCCATGGTG
 751 GGCTGCAAGG CTGCTGTGAC CCTCTTCCTG TATCTGTTGG CGACCAATCA
 801 TTATTGGATC CTGGTGGAGG GTTTGTACTT GCATAGTCTG ATCTTCATGG
 851 CCTTCCTGTC TGATAAGAAC TGCCTGTGGG CTTTGACAAT CATAGGCTGG
 901 GGGATCCCAG CAGTGTTTGT GTCTATATGG GTCAGTGCCA GGGTGTCTCT
 951 GGCAGACACA CAGTGCTGGG ATATCAGTGC AGGCAATTTG AAATGGATTT
1001 ATCAAGTACC AATCCTGGCA GCCATTGTTG TAAACTTCTT CCTCTTCCTC
1051 AATATCATCA GGGTTTTGGC CTCTAAGTTG TGGGAAACAA ACACGGGAAA
1101 ACTGGACCCT AGACAGCAGT ACAGGAAGCT GCTGAAGTCA ACAATGGTGC
1151 TGATGCCACT GTTTGGAGTT CATTACATGC TGTTCATGGC TCTTCCGTAC
1201 ACTGATGTGA CTGGTTTGCT GTGGCAGATT CTGATGCATT ACGAGATGCT
1251 CTTCAATTCT TCACAGGGTT TCTTTGTGGC GTTTATTTAC TGCTTCTGCA
1301 ATGGGGAGGT GCAGGCAGAG GTGAAGAAGG CCTGGTTGCG ACGCAGTCTT
1351 GCGTTAGACC AGAAGCAGAA GGCTCGAGTC CACAGCAGTG CGGGATGTGG
1401 AAGTGGTTAC TATGGAGGAA TGATGTCCCA CACCACCACA CAGAGCGTGT
1451 GTCTCAGTGT CAGTGGTGCT AAAGGCGGTC ATTCTCTGCA CACCATAGGA
1501 GCCAAAGGAC AATCCCGTCT ACAACATTCA GGAAACTTAC CCGGTACGCG
1551 CCTCAGGGCG CATAGACTTT GTTTTACCCA GTGGTCCCAA AGCAGAAAGA
1601 GACTCCATGC AGACAGAGCA GCAGGAATGC AGAGGAAAGC GAGCATGATT
1651 TTGAGCCATA TTTCGTAGCG G
```

FIG.1C (PTH3R Nucleotide SEQ)

```
1     ttacaccata actcacagga gatcacatct ctggacacat ctccaacaag tctctctttq
61    aaacatctac aattggactg acaaatctct tctttaatca aggatctgag ttaatacaaa
121   aaaaaatctg atgaatggaa gaaaatcatc tgtgatggta ttccagaagt taaaatctca
181   acaaaaacaa acaacgggtc ggacttcaac agatgtgtgt ccgcttgaca cggcagcatc
241   agaaagaaac aacatctta acacaatgaa gaagtaatgg ctgcaaacgt ctgcgcttct
301   ctccacatcg acgcgactgc catgtcctga agagaaacag gagctctctg gagagcagga
361   gttctggaaa aggtcaaagg tcctgggtta agcatggtgt cagtggaggt ctctgtggct
421   ttagtgctgt gctgtgtttt gatgggagcc agagctctga ttgattcaga tgatgtcatc
481   acaagagatg aacagatctt tctcctcatt ggtgcgcggt cgaggtgtga gagaaccatc
541   cgtgcacagt cagacgtggt cagagagaat aactgcgctc ctgagtggga tgggatcatt
601   tgctggccca caggaaaacc caatcagatg gtggcagttc tgtgtcctga gtacatctat
661   gacttcaacc acagaggata cgcgtatcga cactgtgatg catcaggtaa ctgggagcag
721   gtgtccatta taaaccggac gtgggcaaac tacacggaat gcaccactta cctgcacacc
781   aaccacagtg atcaggagga agtgtttgag cgcctttacc tcatgtacac tattggataç
841   tccatatcac tggcagcgtt actggtggcg gtctctatcc tttgctattt caaacgtctc
901   cactgcactc gtaactacat ccacatccac ctcttcacct cgttcatatg tcgagcaatc
961   agtatttttg tgaaagacgc cgttctttac gccgtcacga atgatggaga actagaagat
1021  ggggcagtgg aacaaagacc catggtgggc tgcaaggctg ctgtgaccct cttcctgtat
1081  ctgttggcga ccaatcatta ttggatcctg gtggagggtt tgtacttgca tagtctgatc
1141  ttcatggcct tcctgtctga taagaactgc ctgtgggctt tgacaatcat aggctgggg
1201  atcccagcag tgtttgtgtc tatatgggtc agtgccaggg tgtctctggc agacacacag
1261  tgctgggata tcagtgcagg caatttgaaa tggatttatc aagtaccaat cctggcagcc
1321  attgttgtaa acttcttcct cttcctcaat atcatcaggg ttttggcctc taagttgtgg
1381  gaaacaaaca cgggaaaact ggaccctaga cagcagtaca ggaagctgct gaagtcaaca
1441  atggtgctga tgccactgtt tggagttcat tacatgctgt tcatggctct tccgtacact
1501  gatgtgactg gtttgctgtg gcagattctg atgcattacg agatgctctt caattcttca
1561  caggggtttct ttgtggcgtt tatttactgc ttctgcaatg ggaggtgca ggcagaggtg
1621  aagaaggcct ggttgcgacg cagtcttgcg ttagaccaga agcagaaggc tcgagtccac
1681  agcagtgcgg gatgtggaag tggttactat ggaggaatga tgtcccacac cacaacacag
1741  agcgtgtgtc ttagtgtcag tggtgctaaa ggcggtcatt ctctgcacac cataggagcc
1801  aaaggacaat cccgtctaca acattcagga aacttacccg gctacgcgcc tcagggcgca
1861  tagacttgt tttacccagt ggtcccaaag cagaaagaga ctccatgcag acagagcagc
1921  aggaatgcag aggaaagcga gcatgatttt gagccatatt tcgtagcgga tgaggaacat
1981  tctggatcca tgtcttggaa agaactagaa acgatgcttt gatgtaactt gctggatatt
2041  ataaagtggt gcttgctatt gtcagaagtt ctaagttata aaagcttggt ttttgcccag
2101  aatcaaaaca ttcaataata attgnagctt tttatctcca aaaaaaaaaa aa (SEQ ID NO:3)
```

FIG. 1D (PTH1R A.A. SEQ.)
```
   ATGGGAGCCACGCTGATCGTACGCACTTTAGGCTTTCTCTTCTGCGGCACCTTGCTGAGT
   +---------+---------+---------+---------+---------+---------+
   TACCCTCGGTGCGACTAGCATGCGTGAAATCCGAAAGAGAAGACGCCGTGGAACGACTCA
``` a   1   M  G  A  T  L  I  V  R  T  L  G  F  L  F  C  G  T  L  L  S   - SIGNAL PEPTIDE

```
   TTCGTCTATGGTCTGGTCGATGCAGATGATGTCCTCACAAAGGAGGAGCAAATCTATCTT
   +---------+---------+---------+---------+---------+---------+
   AAGCAGATACCAGACCAGCTACGTCTACTACAGGAGTGTTTCCTCCTCGTTTAGATAGAA
``` a   21  F  V  Y  G | L  V  D  A  D  D  V  L  T  K  E  E  Q  I  Y  L   -

```
   CTGTTCAACGCAAAACGAAAATGTGAGCGAGCAATCAAGTCCAAGCATAAAACGTCTGAG
   +---------+---------+---------+---------+---------+---------+
   GACAAGTTGCGTTTTGCTTTTACACTCGCTCGTTAGTTCAGGTTCGTATTTTGCAGACTC
``` a   41  L  F  N  A  K  R  K  C  E  R  A  I  K  S  K  H  K  T  S  E   -

```
   GGATCCTGTCTGCCAGAGTGGGATGGCATCCTATGTTGGCCCGAGGGAGTTCCTGGAAAG
   +---------+---------+---------+---------+---------+---------+
   CCTAGGACAGACGGTCTCACCCTACCGTAGGATACAACCGGGCTCCCTCAAGGACCTTTC
``` a   61  G  S  C  L  P  E  W  D  G  I  L  C  W  P  E  G  V  P  G  K   -

```
   ATGGTGTCCACTTCATGCCCAGAGTACATATATGACTTCAACCACAAAGGTCATGCCTAC
   +---------+---------+---------+---------+---------+---------+
   TACCACAGGTGAAGTACGGGTCTCATGTATATACTGAAGTTGGTGTTTCCAGTACGGATG
``` a   81  M  V  S  T  S  C  P  E  Y  I  Y  D  F  N  H  K  G  H  A  Y   -

```
   CGGCGCTGCGACCTGAACGGGACCTGGGAACTGGCCTCACATAACAACAAAACCTGGGCT
   +---------+---------+---------+---------+---------+---------+
   GCCGCGACGCTGGACTTGCCCTGGACCCTTGACCGGAGTGTATTGTTGTTTTGGACCCGA
``` a   101 R  R  C  D  L  N  G  T  W  E  L  A  S  H  N  N  K  T  W  A   -

```
   AATTACAGCGAATGTGCCAAATTCTTCCCCCATTATAACCAGAACCAGGAGAGGGAGGTT
   +---------+---------+---------+---------+---------+---------+
   TTAATGTCGCTTACACGGTTTAAGAAGGGGGTAATATTGGTCTTGGTCCTCTCCCTCCAA
``` a   121 N  Y  S  E  C  A  K  F  F  P  H  Y  N  Q  N  Q  E  R  E  V   -

```
   TTCGACAGACTTTACCTGATCTACACAGTGGGCTACTCCATCTCTCTGGGATCACTTATG
   +---------+---------+---------+---------+---------+---------+
   AAGCTGTCTGAAATGGACTAGATGTGTCACCCGATGAGGTAGAGAGACCCTAGTGAATAC
```

FIG.2A-1

(PTH1R A.A. SEQ.)

a 141 F D R L Y L I Y |T V G Y S I S L G S L M   - TM1

```
GTGGCCACAGTCATCCTCGGATACTTTCGACGGCTCCACTGCACCAGGAACTACATCCAC
+---------+---------+---------+---------+---------+---------
CACCGGTGTCAGTAGGAGCCTATGAAAGCTGCCGAGGTGACGTGGTCCTTGATGTAGGTG
``` a 161 V A T V I L G Y F| R R L H C T R N Y |I H  -

```
ATGCACCTGTTTCTATCGTTCATGTTGAGGGCCATTAGTATCTTCGTGAAGGATGTGGTG
+---------+---------+---------+---------+---------+---------
TACGTGGACAAAGATAGCAAGTACAACTCCCGGTAATCATAGAAGCACTTCCTACACCAC
``` a 181 M H L F L S F M L R A I S I F V K D V| V   - TM2

```
CTGTACTCTGGTTCGGCGCTGCAGGAAATGGAACGAATCACTGTGGAGGATCTCAAATCC
+---------+---------+---------+---------+---------+---------
GACATGAGACCAAGCCGCGACGTCCTTTACCTTGCTTAGTGACACCTCCTAGAGTTTAGG
``` a 201 L Y S G S A L Q E M E R I T V E D L K S  -

```
ATCACTGAAGCCCCTCCTGCCAACAAAACCCAGTTTATCGGCTGTAAGGTGGCGGTGACG
+---------+---------+---------+---------+---------+---------
TAGTGACTTCGGGGAGGACGGTTGTTTTGGGTCAAATAGCCGACATTCCACCGCCACTGC
``` a 221 I T E A P P A N K T Q F I G C K |V A V T   - TM3

```
CTCTTCTTGTACTTCTTGGCCACTAATTATTACTGGATTCTGGTGGAAGGCCTGTACCTG
+---------+---------+---------+---------+---------+---------
GAGAAGAACATGAAGAACCGGTGATTAATAATGACCTAAGACCACCTTCCGGACATGGAC
``` a 241 L F L Y F L A T N Y Y W I L V E G L Y L  -

```
CACAGCCTTATCTTCATGACCTTCTTCTCAGACAGGAAGTACCTCTGGGGCTTCACTCTG
+---------+---------+---------+---------+---------+---------
GTGTCGGAATAGAAGTACTGGAAGAAGAGTCTGTCCTTCATGGAGACCCCGAAGTGAGAC
``` a 261 H S |L I F M T F F S D R K Y L W| G F T L   - TM4

```
ATTGGTTGGGGTGTTCCTGCGATGTTTGTCACCATCTGGGCGAGTGTTAGAGCCACACTT
+---------+---------+---------+---------+---------+---------
TAACCAACCCCACAAGGACGCTACAAACAGTGGTAGACCCGCTCACAATCTCGGTGTGAA
```

FIG.2A-2

(PTH1R A.A. SEQ.)

a 281 I G V G V P A M F V T I W A S V R A T L -

```
GCTGACACTGAGTGCTGGGATTTGAGTGCAGGAAACCTGAAATGGATTGTGCAGATCCCC
+---------+---------+---------+---------+---------+---------
CGACTGTGACTCACGACCCTAAACTCACGTCCTTTGGACTTTACCTAACACGTCTAGGGG
``` a 301 A D T E C W D L S A G N L K W I V Q I P - TM5

```
ATTCTTACTGCAATTGTTGTCAATTTTTTGTTGTTCCTGAATATAATTCGAGTCTTGGCA
+---------+---------+---------+---------+---------+---------
TAAGAATGACGTTAACAACAGTTAAAAAACAACAAGGACTTATATTAAGCTCAGAACCGT
``` a 321 I L T A I V V N F L L F L N I I R V L A -

```
ACAAAACTTCGAGAAACAAATGCGGGCAGATGTGACACCAGACAACAATATAGGAAGCTG
+---------+---------+---------+---------+---------+---------
TGTTTTGAAGCTCTTTGTTTACGCCCGTCTACACTGTGGTCTGTTGTTATATCCTTCGAC
``` a 341 T K L R E T N A G R C D T R Q Q Y R K L -

```
CTGAAGTCGACTCTGGTCCTCATGCCGTTGTTCGGTGTTCACTACATAGTCTTCATGGCG
+---------+---------+---------+---------+---------+---------
GACTTCAGCTGAGACCAGGAGTACGGCAACAAGCCACAAGTGATGTATCAGAAGTACCGC
``` a 361 L K S T L V L M P L F G V H Y I V F M A - TM6

```
ATGCCTTACACAGAAGTTTCTGGAGTACTGTGGCAAATCCAGATGCATTATGAAATGCTC
+---------+---------+---------+---------+---------+---------
TACGGAATGTGTCTTCAAAGACCTCATGACACCGTTTAGGTCTACGTAATACTTTACGAG
``` a 381 M P Y T E V S G V L W Q I Q M H Y E M L - TM7

```
TTTAACTCAGTCCAGGGATTCTTTGTTGCGATTATATATTGCTTCTGCAACGGAGAGGTC
+---------+---------+---------+---------+---------+---------
AAATTGAGTCAGGTCCCTAAGAAACAACGCTAATATATAACGAAGACGTTGCCTCTCCAG
``` a 401 F N S V Q G F F V A I I Y C F C N G E V -

```
CAAGCGGAAATCAAGAAGGCCTGGAACAGAAGGACTCTTGCTCTGGACTTCAAGAGAAAA
+---------+---------+---------+---------+---------+---------
GTTCGCCTTTAGTTCTTCCGGACCTTGTCTTCCTGAGAACGAGACCTGAAGTTCTCTTTT
```

FIG.2A-3

(PTH1R A.A. SEQ.)

a 421 Q A E I K K A W N R R T L A L D F K R K -

```
GCCAGGAGCGGCAGTAACACATACAGCTATGGACCCATGGTTTCTCACACCAGTGTTACC
+---------+---------+---------+---------+---------+---------
CGGTCCTCGCCGTCATTGTGTATGTCGATACCTGGGTACCAAAGAGTGTGGTCACAATGG
``` a 441 A R S G S N T Y S Y G P M V S H T S V T -

```
AATGTGACGGCGCGGGGGCCGCTGGCCCTTCACCTCACCAACCGACTGGGGCACGTCACC
+---------+---------+---------+---------+---------+---------
TTACACTGCCGCGCCCCCGGCGACCGGGAAGTGGAGTGGTTGGCTGACCCCGTGCAGTGG
``` a 461 N V T A R G P L A L H L T N R L G H V T -

```
ACTAACGGCCACAGAAACCTTCCGGGATACATAAAAAACGGCTCCGTTTCAGAAAACTCC
+---------+---------+---------+---------+---------+---------
TGATTGCCGGTGTCTTTGGAAGGCCCTATGTATTTTTTGCCGAGGCAAAGTCTTTTGAGG
``` a 481 T N G H R N L P G Y I K N G S V S E N S -

```
ATCCCGTCCTCGGGTCACGAGCTTCACATTCAGGAGGAAGAGCCTTCGAAGACCTTCCAG
+---------+---------+---------+---------+---------+---------
TAGGGCAGGAGCCCAGTGCTCGAAGTGTAAGTCCTCCTTCTCGGAAGCTTCTGGAAGGTC
``` a 501 I P S S G H E L H I Q E E E P S K T F Q -

```
ATGGAGAAAACCATCCAGGTGGTGGAGGAGGAAAGAGAAACCGTCATGT
+---------+---------+---------+---------+--------
TACCTCTTTTGGTAGGTCCACCACCTCCTCCTTTCTCTTTGGCAGTACA
``` a 521 M E K T I Q V V E E E R E T V M -
(SEQ ID NO: 2)

FIG.2A-4

PTH3R Amino Acid Sequence

```
     ATGGTGTCAGTGGAGGTCTCTGTGGCTTTAGTGCTGTGTGCTGTGTTTTGATGGGAGCCAGA
 97  ---+---------+---------+---------+---------+---------+------ 156
     TACCACAGTCACCTCCAGAGACACCGAAATCACGACACGACACAAAACTACCCTCGGTCT
``` a     M   V   S   V   E   V   S   V   A   L   V   L   C   C   V   L   M   G   A   R   -

```
     GCTCTGATTGATTCAGATGATGTCATCACAAGAGATGAACAGATCTTTCTCCTCATTGGT
157  ---+---------+---------+---------+---------+---------+------ 216
     CGAGACTAACTAAGTCTACTACAGTAGTGTTCTCTACTTGTCTAGAAAGAGGAGTAACCA
``` a    A   L   I   D   S   D   D   V   I   T   R   D   E   Q   I   F   L   L   I   G   -

```
     GCGCGGTCGAGGTGTGAGAGAACCATCCGTGCACAGTCAGACGTGGTCAGAGAGAATAAC
217  ---+---------+---------+---------+---------+---------+------ 276
     CGCGCCAGCTCCACACTCTCTTGGTAGGCACGTGTCAGTCTGCACCAGTCTCTCTTATTG
``` a    A   R   S   R   C   E   R   T   I   R   A   Q   S   D   V   V   R   E   N   N   -

```
     TGCGCTCCTGAGTGGGATGGGATCATTTGCTGGCCCACAGGAAAACCCAATCAGATGGTG
277  ---+---------+---------+---------+---------+---------+------ 336
     ACGCGAGGACTCACCCTACCCTAGTAAACGACCGGGTGTCCTTTTGGGTTAGTCTACCAC
``` a    C   A   P   E   W   D   G   I   I   C   W   P   T   G   K   P   N   Q   M   V   -

```
     GCAGTTCTGTGTCCTGAGTACATCTATGACTTCAACCACAGAGGATACGCGTATCGACAC
337  ---+---------+---------+---------+---------+---------+------ 396
     CGTCAAGACACAGGACTCATGTAGATACTGAAGTTGGTGTCTCCTATGCGCATAGCTGTG
``` a    A   V   L   C   P   E   Y   I   Y   D   F   N   H   R   G   Y   A   Y   R   H   -

```
     TGTGATGCATCAGGTAACTGGGAGCAGGTGTCCATTATAAACCGGACGTGGGCAAACTAC
397  ---+---------+---------+---------+---------+---------+------ 456
     ACACTACGTAGTCCATTGACCCTCGTCCACAGGTAATATTTGGCCTGCACCCGTTTGATG
``` a    C   D   A   S   G   N   W   E   Q   V   S   I   I   N   R   T   W   A   N   Y   -

```
     ACGGAATGCACCACTTACCTGCACACCAACCACAGTGATCAGGAGGAAGTGTTTGAGCGC
457  ---+---------+---------+---------+---------+---------+------ 516
     TGCCTTACGTGGTGAATGGACGTGTGGTTGGTGTCACTAGTCCTCCTTCACAAACTCGCG
``` a    T   E   C   T   T   Y   L   H   T   N   H   S   D   Q   E   E   V   F   E   R   -

FIG.2B-1

```
     CTTTACCTCATGTACACTATTGGATACTCCATATCACTGGCAGCGTTACTGGTGGCGGTC
517  ---+---------+---------+---------+---------+---------+------ 576
     GAAATGGAGTACATGTGATAACCTATGAGGTATAGTGACCGTCGCAATGACCACCGCCAG
``` a      L   Y   L   M   Y   T   I   G   Y   S   I   S   L   A   A   L   L   V   A   V   -

```
     TCTATCCTTTGCTATTTCAAACGTCTCCACTGCACTCGTAACTACATCCACATCCACCTC
577  ---+---------+---------+---------+---------+---------+------ 636
     AGATAGGAAACGATAAAGTTTGCAGAGGTGACGTGAGCATTGATGTAGGTGTAGGTGGAG
``` a      S   I   L   C   Y   F   K   R   L   H   C   T   R   N   Y   I   H   I   H   L   -

```
     TTCACCTCGTTCATATGTCGAGCAATCAGTATTTTTGTGAAAGACGCCGTTCTTTACGCC
637  ---+---------+---------+---------+---------+---------+------ 696
     AAGTGGAGCAAGTATACAGCTCGTTAGTCATAAAAACACTTTCTGCGGCAAGAAATGCGG
``` a      F   T   S   F   I   C   R   A   I   S   I   F   V   K   D   A   V   L   Y   A   -

```
     GTCACGAATGATGGAGAACTAGAAGATGGGGCAGTGGAACAAAGACCCATGGTGGGCTGC
697  ---+---------+---------+---------+---------+---------+------ 756
     CAGTGCTTACTACCTCTTGATCTTCTACCCCGTCACCTTGTTTCTGGGTACCACCCGACG
``` a      V   T   N   D   G   E   L   E   D   G   A   V   E   Q   R   P   M   V   G   C   -

```
     AAGGCTGCTGTGACCCTCTTCCTGTATCTGTTGGCGACCAATCATTATTGGATCCTGGTG
757  ---+---------+---------+---------+---------+---------+------ 816
     TTCCGACGACACTGGGAGAAGGACATAGACAACCGCTGGTTAGTAATAACCTAGGACCAC
``` a      K   A   A   V   T   L   F   L   Y   L   L   A   T   N   H   Y   W   I   L   V   -

```
     GAGGGTTTGTACTTGCATAGTCTGATCTTCATGGCCTTCCTGTCTGATAAGAACTGCCTG
817  ---+---------+---------+---------+---------+---------+------ 876
     CTCCCAAACATGAACGTATCAGACTAGAAGTACCGGAAGGACAGACTATTCTTGACGGAC
``` a      E   G   L   Y   L   H   S   L   I   F   M   A   F   L   S   D   K   N   C   L   -

```
     TGGGCTTTGACAATCATAGGCTGGGGGATCCCAGCAGTGTTTGTGTCTATATGGGTCAGT
877  ---+---------+---------+---------+---------+---------+------ 936
     ACCCGAAACTGTTAGTATCCGACCCCCTAGGGTCGTCACAAACACAGATATACCCAGTCA
``` a      W   A   L   T   I   I   G   W   G   I   P   A   V   F   V   S   I   W   V   S   -

FIG.2B-2

```
         GCCAGGGTGTCTCTGGCAGACACACAGTGCTGGGATATCAGTGCAGGCAATTTGAAATGG
   937   ---+---------+---------+---------+---------+---------+------  996
         CGGTCCCACAGAGACCGTCTGTGTGTCACGACCCTATAGTCACGTCCGTTAAACTTTACC

α        A  R  V  S  L  A  D  T  Q  C  W  D  I  S  A  G  N  L  K  W   -

ATTTATCAAGTACCAATCCTGGCAGCCATTGTTGTAAACTTCTTCCTCTTCCTCAATATC
   997   ---+---------+---------+---------+---------+---------+------  1056
         TAAATAGTTCATGGTTAGGACCGTCGGTAACAACATTTGAAGAAGGAGAAGGAGTTATAG

α        I  Y  Q  V  P  I  L  A  A  I  V  V  N  F  F  L  F  L  N  I   -

ATCAGGGTTTTGGCCTCTAAGTTGTGGGAAACAAACACGGGAAAACTGGACCCTAGACAG
  1057   ---+---------+---------+---------+---------+---------+------  1116
         TAGTCCCAAAACCGGAGATTCAACACCCTTTGTTTGTGCCCTTTTGACCTGGGATCTGTC

α        I  R  V  L  A  S  K  L  W  E  T  N  T  G  K  L  D  P  R  Q   -

CAGTACAGGAAGCTGCTGAAGTCAACAATGGTGCTGATGCCACTGTTTGGAGTTCATTAC
  1117   ---+---------+---------+---------+---------+---------+------  1176
         GTCATGTCCTTCGACGACTTCAGTTGTTACCACGACTACGGTGACAAACCTCAAGTAATG

α        Q  Y  R  K  L  L  K  S  T  M  V  L  M  P  L  F  G  V  H  Y   -

ATGCTGTTCATGGCTCTTCCGTACACTGATGTGACTGGTTTGCTGTGGCAGATTCTGATG
  1177   ---+---------+---------+---------+---------+---------+------  1236
         TACGACAAGTACCGAGAAGGCATGTGACTACACTGACCAAACGACACCGTCTAAGACTAC

α        M  L  F  M  A  L  P  Y  T  D  V  T  G  L  L  W  Q  I  L  M   -

CATTACGAGATGCTCTTCAATTCTTCACAGGGTTTCTTTGTGGCGTTTATTTACTGCTTC
  1237   ---+---------+---------+---------+---------+---------+------  1296
         GTAATGCTCTACGAGAAGTTAAGAAGTGTCCCAAAGAAACACCGCAAATAAATGACGAAG

α        H  Y  E  M  L  F  N  S  S  Q  G  F  F  V  A  F  I  Y  C  F   -

TGCAATGGGGAGGTGCAGGCAGAGGTGAAGAAGGCCTGGTTGCGACGCAGTCTTGCGTTA
  1297   ---+---------+---------+---------+---------+---------+------  1356
         ACGTTACCCCTCCACGTCCGTCTCCACTTCTTCCGGACCAACGCTGCGTCAGAACGCAAT

```
        GACCAGAAGCAGAAGGCTCGAGTCCACAGCAGTGCGGGATGTGGAAGTGGTTACTATGGA
   1357 ---+---------+---------+---------+---------+---------+------ 1416
        CTGGTCTTCGTCTTCCGAGCTCAGGTGTCGTCACGCCCTACACCTTCACCAATGATACCT a       D  Q  K  Q  K  A  R  V  H  S  S  A  G  C  G  S  G  Y  Y  G  -

GGAATGATGTCCCACACCACCACACAGAGCGTGTGTCTCAGTGTCAGTGGTGCTAAAGGC
   1417 ---+---------+---------+---------+---------+---------+------ 1476
        CCTTACTACAGGGTGTGGTGGTGTGTCTCGCACACAGAGTCACAGTCACCACGATTTCCG a       G  M  M  S  H  T  T  T  Q  S  V  C  L  S  V  S  G  A  K  G  -

GGTCATTCTCTGCACACCATAGGAGCCAAAGGACAATCCCGTCTACAACATTCAGGAAAC
   1477 ---+---------+---------+---------+---------+---------+------ 1536
        CCAGTAAGAGACGTGTGGTATCCTCGGTTTCCTGTTAGGGCAGATGTTGTAAGTCCTTTG a       G  H  S  L  H  T  I  G  A  K  G  Q  S  R  L  Q  H  S  G  N  -

TTACCCGGCTACGCGCCTCAGGACACAGAGACTTTGTTTTACCCAGTGGTCCCAAAGCAG
   1537 ---+---------+---------+---------+---------+---------+------ 1596
        AATGGGCCGATGCGCGGAGTCCTGTGTCTCTGAAACAAAATGGGTCACCAGGGTTTCGTC a       L  P  G  Y  A  P  Q  D  T  E  T  L  F  Y  P  V  V  P  K  Q  -

AAAGAGACTCCATGCAGACAGAGCAGCAGGAATGCAGAGGAAAGCGAGCATGATTTTGAG
   1597 ---+---------+---------+---------+---------+---------+------ 1656
        TTTCTCTGAGGTACGTCTGTCTCGTCGTCCTTACGTCTCCTTTCGCTCGTACTAAAACTC a       K  E  T  P  C  R  Q  S  S  R  N  A  E  E  S  E  H  D  F  E  -

CCATATTTCGTAGCGGATGAGGAACATTCTGGATCCATGTCTTGGAAAGAACTAGAAACG
   1657 ---+---------+---------+---------+---------+---------+------ 1716
        GGTATAAAGCATCGCCTACTCCTTGTAAGACCTAGGTACAGAACCTTTCTTGATCTTTGC a       P  Y  F  V  A  D  E  E  H  S  G  S  M  S  W  K  E  L  E  T  -

ATGCTTTGA
   1717 ---+----- 1725
        TACGAAACT a       M  L  *   - (SEQ IS NO: 4)
```

FIG.2B-4

```
                Signal Peptide
zPTH3R    ┌─M  VSVEVSV    ALVLCC  VLMGARA─┐                                         LIDSDDVITR@EQIFLLIGARSRCERTIR
zPTH1R    │ M  GATLIVRTLGF LFCGTLLSFYYG   │                                                      LVDADDVLTKEEQIYLLFNAKRKCERAIK
zPTH2R    └─M  LTVSL      LILCKP  SSPSPVKIIPVDDLPATAELRASVLRVSLPKTF IKSFLNHLLQAGEDGEITAEEQVQMLLDAKLQC  LQKVSSDDPA
                                                                                  #    #
zPTH3R    AQSDVVRENNCAPEWDGIICWPTGKPNQMVAVLCPEYIYDFNHRGYAYRHCDASGNMEQVSIINRTWANYTECTTYL HTNHSDQEEVFERLYLMYT@GY
zPTH1R    SKHKTSEGSCLPEWDGILCWPEGVPGKMVSTSCPEYIYDFNHKGHAYRRCDLNGTWELASHNNKTWANYSECAKFFPHYNQNQEREVFDRLYLIYTVGY
zPTH2R       VGVCVPEWDGLICWPQGFPGTLTKTPCGYIYDFNHAAHAYRRCDSNGSSVLAESSNKTWNNYTECIK  SPEPNKKRQVFFERLHIMYTVGY zPTH3R    SISLAALLVAVSILCYFRRLHCTRNYIHIHLFTSF@CRAISIFVKDAVLYAVTNDGELEDGAVEQRP                MVGCKAAVTLFLYLLATN
zPTH1R    SISLGSLMVATVILGYFRRLHCTRNYIHMHLFLSFMLRAISIFVKDVVLYSGSALQEMERITVEDLKSITEA   PPANKTQFIGCKVAVTLFLYFLAIN
zPTH2R    AVSFSSLLVAIFIIGYFRRLHCTRNYIHMHLFVSFMLRAASIFVKDHVVHTSAGLQESDAVLM N  NFTNAVDVAPVDTSQYMGCKVTVLLFIYFLAIN zPTH3R    @YWILVEGLYLHSLIFMAFLSDKNCL_WA@TIIGWGIPAVFVSIWSAR@SLADTQCWD@SAGNLKWIYQVPILAAIVVNFFLFLNIIRVLA@KLWETNTG
zPTH1R    YYWILVEGLYLHSLIFMIFFSDRKYLWGFTLIGWMGYPAMFVTIWASVRATLADIECWDLSAGNLKWIVQIPILTAIVVNFLLFLNIIRVLATKLRETNAG
zPTH2R    YYWILVEGLYLHSLIFMAFLSDSKYLWGFTLIGWMGYPAVFVAAWAVRATLADARCWELSAGNIKWIYQEPILTAIGLNFILFVNIVRVLATKIRETNGG zPTH3R    KLDPRQQYRKLLKSTMVLMPLFGVHYM@FMALPYI@VTGLLWQIILMHYEMLFNSSQGFFVAF@YCFCNGEVQAEVKKAWLRRSLALDQKQKARVHSSAGC
zPTH1R    RCDTRQQYRKLLKSTLVLMPLFGVHYIVFGVHYIVFMAMPYTEVSGVLWQIQMHYEMLFNSVQGFFVAIIYCFCNGEVQAEIKKAWNRRTLALDFKRKARSGSNT Y
zPTH2R    RYDTRKQYRKLLAKSTQVLVFVFGVHYIVFVGMPHT FEGLGWEERMYCELFFNSFQGFFVSIIYCYCNGEVQTEIKKTWTRWNLAFDWKGPVVCGSNR Y zPTH3R    GSGYYGGMSHTTQSVC  LSVSG  AKGGHSLHTIGAKGQSRLQHSGNLPGYA PQD  TET LFY  PVV  PKQKETPCRQSSRNAEESEHDFEPYF
zPTH1R    S  YGPMVSHTSVTNV   TARG PLALHLTNRLGHV   TTNGHRNLPGYIKNGSVS ENSIPSSGHE LHIQEEEPSKT      FQMEKTI  Q
zPTH2R    GSVLTGLNNS TSSQSLAAGGPGTIRSTTLFSSRVYRSSGGPTVSTHATLPGYVL    NSD     ADSLPP    SIPEEP  EDSAKQVDDILLKESLPTR zPTH3R    VADEEHSCSSMSWKELETML  (SEQ ID NO:4)
zPTH1R    VVEEERETVM           (SEQ ID NO:2)
zPTH2R    PSSGLEDD       EETL  (SEQ ID NO:5)
```

FIG. 3

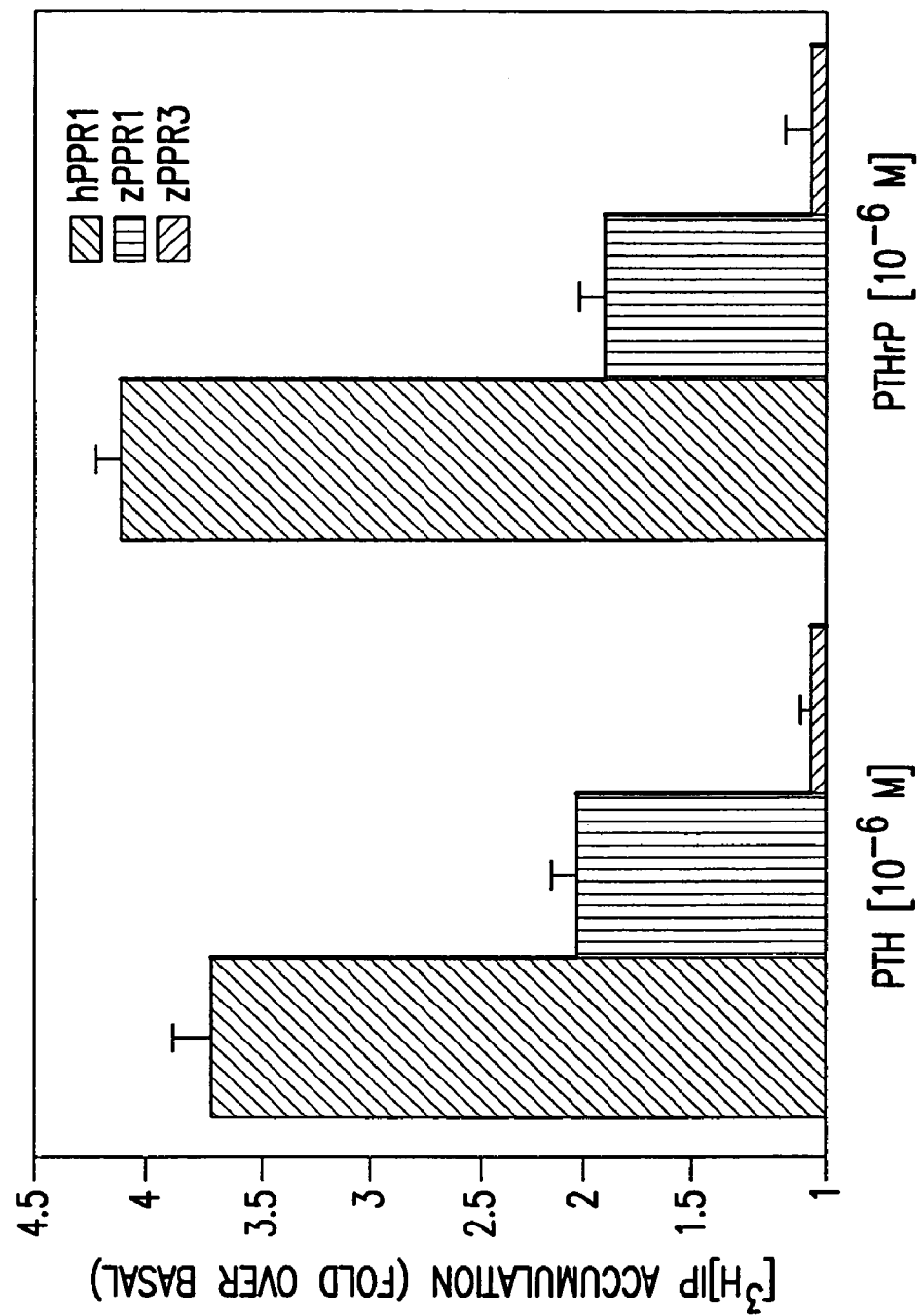

PTH1R RECEPTORS

This application is a divisional application of U.S. non-provisional application 09/449,632 filed on Nov. 30, 1999 now U.S. Pat No. 6,541,220, which claims the benefit of the filing date of U.S. provisional application 60/110,467 filed on Nov. 30, 1998, both herein incorporated by reference.

STATEMENT AS TO RIGHTS TO INVENTIONS MADE UNDER FEDERALLY-SPONSORED RESEARCH AND DEVELOPMENT

Part of the work performed during development of this invention utilized U.S. Government funds. The U.S. Government has certain rights in this invention.

BACKGROUND OF THE INVENTION

1. Field of the Invention

The present invention is related to the fields of molecular biology, developmental biology, physiology, neurobiology and medicine. The invention provides polynucleotides encoding the zebrafish PTH1R receptor and polynucleotides for a novel zebrafish PTH3R receptor, as well as vectors and cells containing said polynucleotides. The invention further provides polypeptides for the PTH1R and PTH3R receptors. The polynucleotides and polypeptides of the invention are useful for the identification of agonist and antagonists of PTH1R or PTH3R receptor function and as reagents in the treatment of diseases or disorders associated with PTH1R or PTH3R function.

2. Related Art

The parathyroid hormone (PTH)/PTH-related peptide (PTHrP) receptor (PTH1R) mediates in mammals and frogs the actions of PTH and PTHrP. Both peptides, most likely evolved through a gene duplication event from a common ancestral gene, and have retained limited homology within the amino-terminal region. Because of their structural conservation, PTH and PTHrP bind with similar affinity to the PTH1R, and activate this common receptor with similar or indistinguishable efficacy. Due to this unusual ligand-specificity, the PTH1R mediates the endocrine actions of PTH, the most important peptide regulator of calcium homeostasis in mammals, and the autocrine/paracrine actions of PTHrP, which is important for normal chondrocyte proliferation and differentiation (Karaplis, et al., (1997)); Lanske, et al., (1996)), and most likely for other, still incompletely defined functions including pancreas, skin, and breast development, as well as tooth eruption (Wysolmerski, et al., (1996)).

In addition to the PTH1R, a PTH type-2 receptor (PTH2R) has been isolated from mammals and teleosts (Usdin, et al., (1995); Rubin, et al. (1999)), and at least the human PTH2R is activated by PTH and a recently isolated hypothalamus peptide (Usdin, et al., (1999)). Its biological importance remains uncertain, as does the importance of additional receptors for which there is growing biological and pharmacological evidence. For example, receptors with specificity for amino-terminal PTH and PTHrP have been described for keratinocytes, squamous carcinoma cell lines, and central nervous system cells (Orloff et al., (1995 and 1996); Fukayama, et al., (1995)), and there is evidence for a PTHrP-selective receptor in the mammalian supraoptic nucleus (Yamamoto et al., (1997) and (1998)). In addition, the midregional portion of PTHrP stimulates an increase in intracellular free calcium in some cell lines and increases placental calcium transport (Kovacs et al., (1996); Wu et al., (1996); Orloff et al., (1996)), and the carboxy-terminal portion of PTH binds to a distinct receptor on clonal cell lines (Inomata, et al., (1995); Takasu, et al., (1998)).

Research on the parathyroid hormone (PTH) has been extensive. Formulations of PTH and compounds with PTH activity have been described (see U.S. Pat. Nos. 5,496,801; 5,814,603; 5,208,041;), and methods to produce the same are also known (see U.S. Pat. Nos. 5,616,560 and 5,010,010). In addition, analogs and inhibitors of PTH may be found in the prior art (see U.S. Pat. Nos. 4,423,037; 5,693,616; 5,695,955 and 5,798,225).

Thus, the invention furthers the art by focusing on PTH receptors and providing reagents and methods that are distinct and separate from PTH.

SUMMARY OF THE INVENTION

The present invention provides isolated nucleic acid molecules comprising a polynucleotide encoding a novel PTH1R receptor having the amino acid sequence shown in FIG. 2A (SEQ ID NO:2) or the amino acid sequence encoded by the cDNA clone deposited in a bacterial host with the ATCC as patent deposit PTA-916 on Nov. 4, 1999. The present invention also relates to recombinant vectors, which include the isolated nucleic acid molecules of the present invention, and to host cells containing the recombinant vectors, as well as to methods of making such vectors and host cells and for using them for production of PTH1R polypeptides or peptides by recombinant techniques. The invention further provides an isolated PTH1R polypeptide having an amino acid sequence encoded by a polynucleotide described herein.

The present invention also provides isolated nucleic acid molecules comprising a polynucleotide encoding a novel PTH3R receptor having the amino acid sequence shown in FIG. 2B (SEQ ID NO:4) or the amino acid sequence encoded by the cDNA clone deposited in a bacterial host with the ATCC as patent deposit PTA-915 on Nov. 4, 1999. The present invention also relates to recombinant vectors, which include the isolated nucleic acid molecules of the present invention, and to host cells containing the recombinant vectors, as well as to methods of making such vectors and host cells and for using them for production of PTH3R polypeptides or peptides by recombinant techniques. The invention further provides an isolated PTH3R polypeptide having an amino acid sequence encoded by a polynucleotide described herein.

The present invention also provides a screening method for identifying compounds capable of enhancing or inhibiting a cellular response induced by the PTH1R or PTH3R receptor, which involves contacting cells which express the PTH1R or PTH3R receptor with the candidate compound, assaying a cellular response, and comparing the cellular response to a standard cellular response, the standard being assayed when contact is made in absence of the candidate compound; whereby, an increased cellular response over the standard indicates that the compound is an agonist and a decreased cellular response over the standard indicates that the compound is an antagonist.

In another aspect, a screening assay for agonists and antagonists is provided which involves determining the effect a candidate compound has on PTH or PTHrP binding to the PTH1R or PTH3R receptor. In particular, the method involves contacting the PTH1R or PTH3R receptor with a PTH or PTHrP polypeptide and a candidate compound and determining whether PTH or PTHrP polypeptide binding to the PTH1R or PTH3R receptor is increased or decreased due to the presence of the candidate compound.

An additional aspect of the invention is related to a method for treating an individual in need of an increased level of PTH1R or PTH3R activity in the body comprising administering to such an individual a composition comprising a therapeutically effective amount of an isolated PTH1R or PTH3R polypeptide of the invention or an agonist thereof.

A still further aspect of the invention is related to a method for treating an individual in need of a decreased level of PTH1R or PTH3R receptor activity in the body comprising, administering to such an individual a composition comprising a therapeutically effective amount of an PTH1R or PTH3R antagonist.

The invention further provides a diagnostic method useful during diagnosis or prognosis of diseases and disorders associated with PTH1R or PTH3R receptor expression or function.

BRIEF DESCRIPTION OF THE FIGURES

FIG. 1. A) Schematic representation of exons M6/7 and M7 (A), and of the cDNA encoding the PTH1R or the PTH3R (B). Vertical boxes depict the predicted location of the membrane-spanning helices; recognition sites for restriction enzymes are shown by //. For and Rev arrows indicate the approximate location of primers used for RT-PCR, 5' RACE, and 3' RACE for zPTH1R and zPTH3R. C) The nucleotide sequence of the PTH1R receptor cDNA. D) The nucleotide sequence of the PTH3R receptor cDNA.

⇐, degenerate primers; ←, zPTH1R-specific; ◂, zPTH3R-specific; ζ, potential sites for N-linked glycosylation.

FIG. 2A) The amino acid sequence of the PTH1R receptor; B) The amino acid sequence of the PTH3R receptor.

FIG. 3 Alignment of the amino acid sequences of the zPTH1R, zPTH2R, and zPTH3R. The sequences were aligned using the GAP and pileup algorithms of the GCG package (Genetics Computer Group, Wisconsin). Conserved consensus sites for potential N-glycosyjation are identified by #; Gaps were introduced to maximize sequence homology. The seventeen residues which are lacking in one splice variant of the characterized zPTH2R (Rubin et al., (1999)) are boxed; the residues which are predicted to comprise the signal peptide are outlined with a stippled box; and those residues which are likely to be PTH3R-specific are boxed.

FIG. 4A-D. COS-7 cells transiently expressing the zPTH1R or the zPTH3R were evaluated for competitive inhibition of radioligand binding (A,B) and agonist-stimulated cAMP production (C,D). Binding studies (as described in Materials and Methods) used either $^{125}$I-[Nle$^{8,21}$,Tyr$^{34}$]rPTH-(1-34)amide (Panel A) or $^{125}$I-[Tyr$^{36}$]hPTHrP-(1-36)amide (Panel B) as radioligand and varying amounts of unlabeled peptide. Data are expressed as % of maximal binding. Cyclic AMP accumulation is expressed as % of maximal for the zPTH1R (C) or the zPTH3R (D); basal cAMP accumulation was 3-4 pmol/well for either receptor; maximal accumulation of 106.2 pmol/well for the zPTH1R, and 285.4 pmol/well for the zPTH3R. ■□, PTH; ●○, PTHrP; filled symbols represent zPTH1R, open symbols represent zPTH3R. All data represent the mean±SEM of at least three independent transfections.

FIG. 5. Accumulation of total IP in COS-7 cells transiently expressing the zPTH1R, or the zPTH3R or the hPTH1R. Hydrolysis of total IPs was assessed as described in the absence or presence of PTHrP ($10^{-6}$ M) or PTH ($10^{-6}$ M). Data are expressed as fold above basal and represent the mean±SEM of at two independent experiments.

Figure 4A:
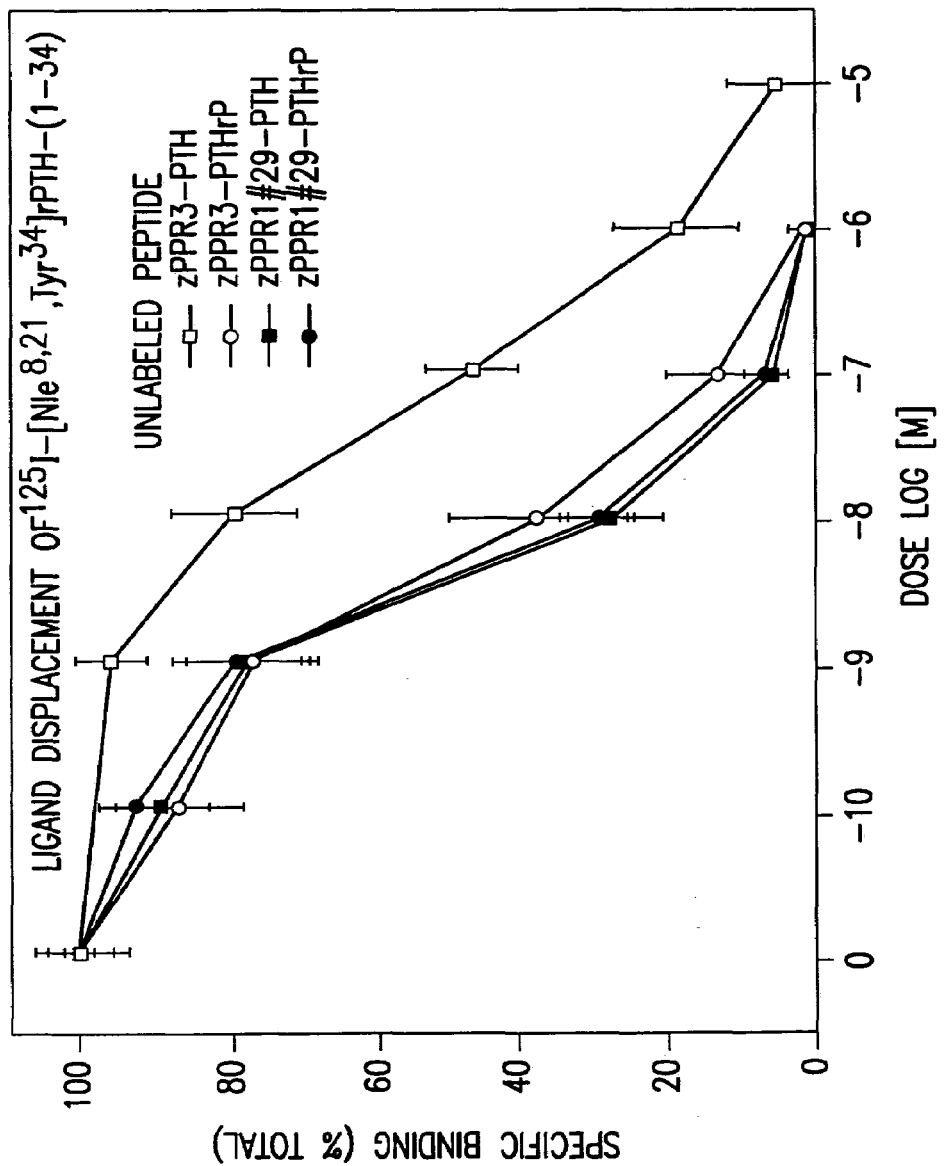
Figure 4B:
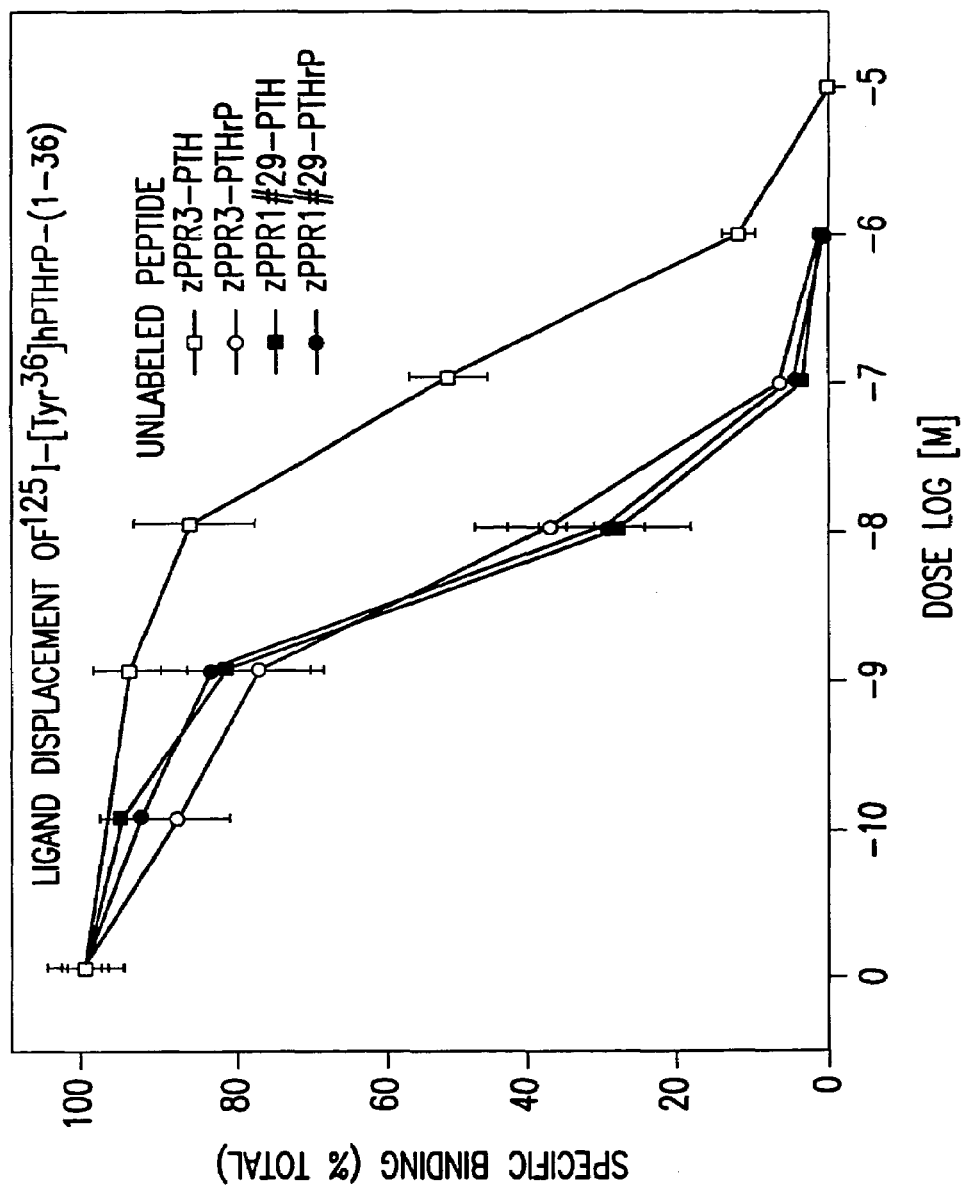
Figure 4C:
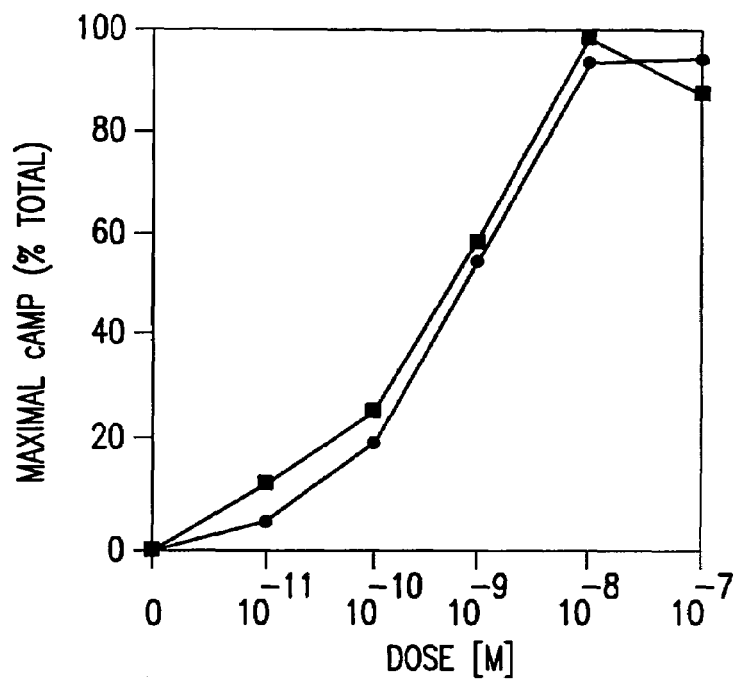
Figure 4D:
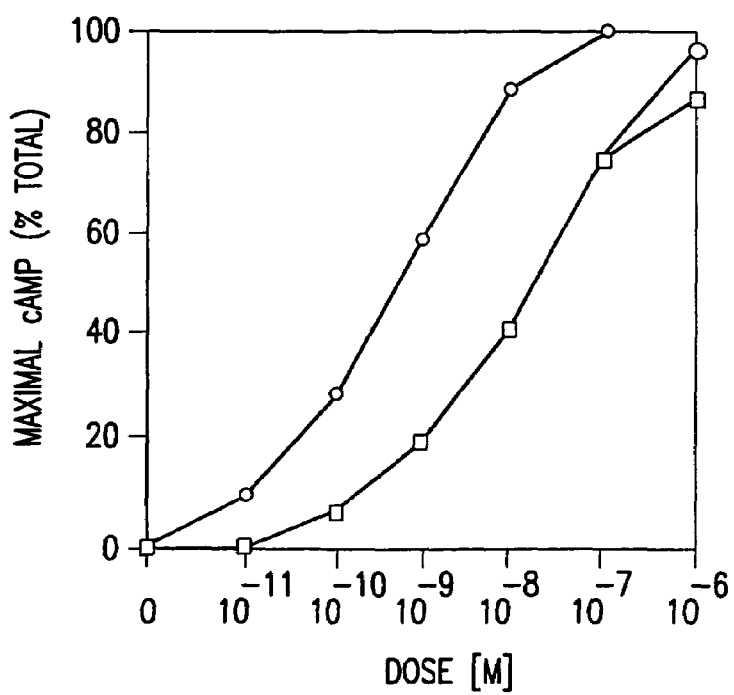
Figure 6:
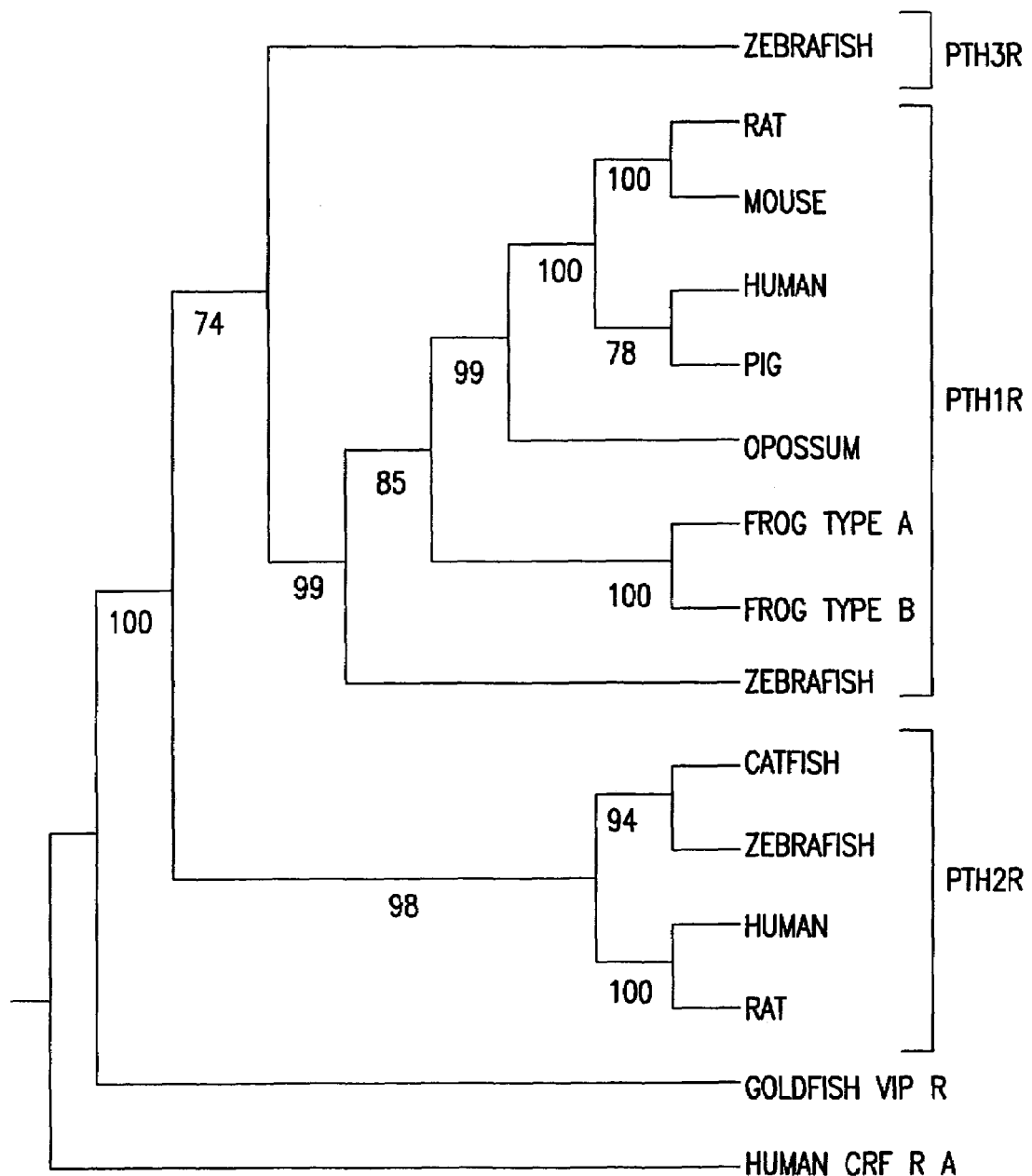

FIG. 6. A phylogenetic analysis, as described in Materials and Methods, indicated that the single most parsimonious tree had a length of 1549 steps, and a consistency index excluding uninformative characters of 0.863. The bootstrap confidence intervals are shown next to the branch points and indicate the percentage of trials which support a given branch in 100 branch-and-bound iterations.

Figure 7:
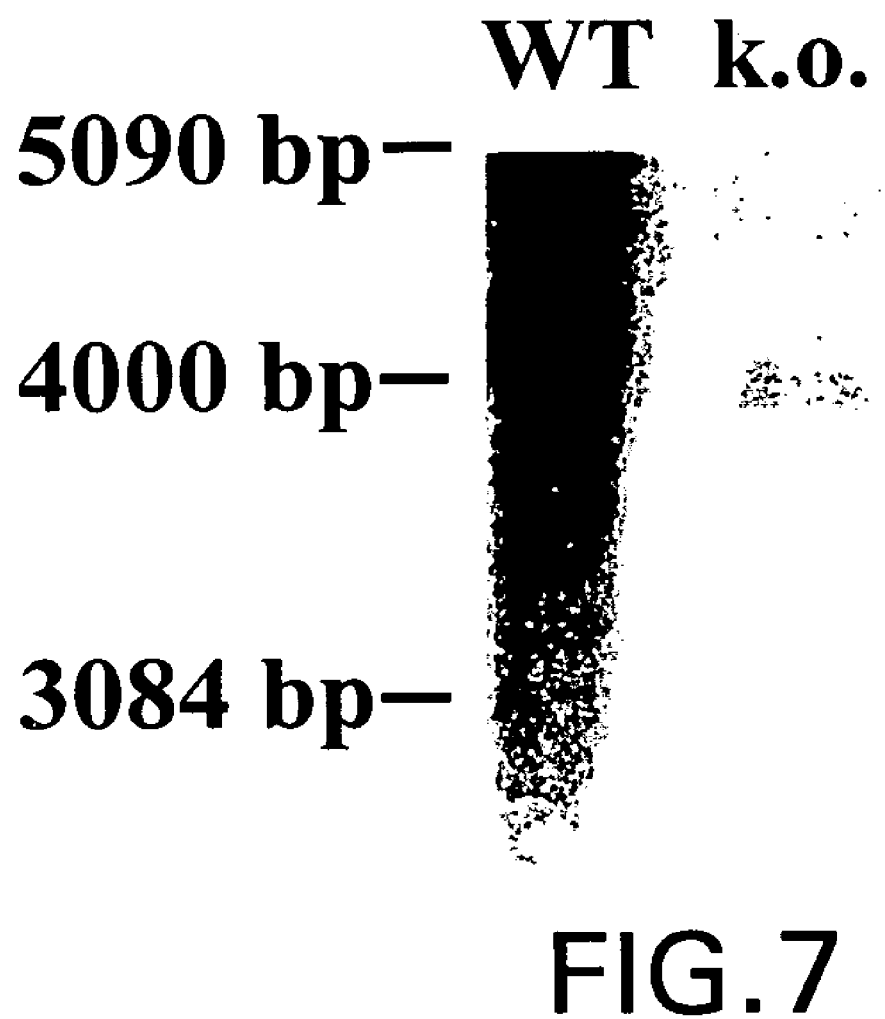

FIG. 7. Southern blot analysis of wild-type (left lane) and PTH/PTHrP receptor knock out mouse genomic DNA (right lane) probed with PTH3R.

DETAILED DESCRIPTION OF THE PREFERRED EMBODIMENTS

The present invention provides novel PTH receptor nucleic acids and proteins (Rubin and Jüppner, (1999)). More specifically, the present invention provides isolated nucleic acid molecules comprising a polynucleotide encoding a novel PTH1R polypeptide having the amino acid sequence shown in FIG. 2A (SEQ ID NO:2), which was determined by sequencing a cloned cDNA. The PTH1R protein of the present invention shares sequence homology with previously identified PTH1R and PTH2R sequences. The nucleotide sequence shown in FIG. 1C (SEQ ID NO:1) was obtained by sequencing a cDNA clone (zPTH1R), which was deposited on Nov. 4, 1999 at the American Type Culture Collection, 10801 University Boulevard, Manassas, Va. 20110-2209, and given accession number PTA-916. The cDNA was inserted between the EcoRI and SphI site of plasmid pcDNAI/Amp (Invitrogen).

The present invention also provides isolated nucleic acid molecules comprising a polynucleotide encoding a novel PTH3R polypeptide having the amino acid sequence shown in FIG. 2B (SEQ ID NO:4), which was determined by sequencing a cloned cDNA. The PTH3R protein of the present invention shares sequence homology with the PTH1R protein sequence of the invention and other PTH1R and PTH2R protein sequences previously. The nucleotide sequence shown in FIG. 1C (SEQ ID NO:3) was obtained by sequencing a cDNA clone(zPTH3R), which was deposited on Nov. 4, 1999 at the American Type Culture Collection, 10801 University Boulevard, Manassas, Va. 20110-2209, and given accession number PTA-915. The cDNA was inserted between the BamHI and NotI site of plasmid pcDNAI/Amp (Invitrogen).

Nucleic Acid Molecules

Unless otherwise indicated, all nucleotide sequences determined by sequencing a DNA molecule herein were determined by manual sequencing, and all amino acid sequences of polypeptides encoded by DNA molecules determined herein were predicted by translation of a DNA sequence determined as above. Therefore, as is known in the art for any DNA sequence determined by this approach, any nucleotide sequence determined herein may contain some errors. Nucleotide sequences determined by manual sequencing are typically at least about 95% to at least about 99.9% identical to the actual nucleotide sequence of the sequenced DNA molecule. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Using the information provided herein, such as the nucleotide sequence in FIG. 1C or 1D, a nucleic acid molecule of the present invention encoding a PTH1R or PTH3R polypeptide, respectively, may be obtained using standard cloning and screening procedures, such as those for cloning cDNAs using mRNA as starting material. Illustrative of the invention, the nucleic acid molecule described in FIG. 1C (SEQ ID NO:1) was discovered using oligonucleotide primers in a polymerase chain reaction (PCR) with total RNA isolated from adult zebrafish. The determined nucleotide sequence of the PTH1R cDNA of FIG. 1C (SEQ ID NO:1) contains an open reading frame encoding a protein of about 536 amino acid residues, with a predicted leader sequence of about 24 amino acid residues, and a deduced molecular weight of about 61.4 kDa for the non-glycosylated form. The amino acid sequence of the predicted mature PTH1R receptor is shown in FIG. 2A from amino acid residue about 25 to residue about 536. The PTH1R protein shown in FIG. 2A (SEQ ID NO:2) is about 76% identical to human PTH1R sequence and about 68% identical to human PTH2R sequence.

Also illustrative of the invention is the nucleic acid molecule described in FIG. 1D (SEQ ID NO:3) was discovered in a zebrafish 1DNA library (Clontech). The determined nucleotide sequence of the FIG. 1D (SEQ ID NO:3) contains an open reading frame encoding a protein of about 542 amino acid residues, with a predicted leader sequence of about 21 amino acid residues, and a deduced molecular weight of about 59.2 kDa. The PTH3R protein shown in FIG. 2B (SEQ ID NO:4) is about 68% and 57% similar to human PTH1R and human PTH2R, respectively.

As indicated, the present invention also provides the mature form(s) of the PTH1R and PTH3R receptors of the present invention. According to the signal hypothesis, proteins secreted by mammalian cells have a signal or secretory leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species on the protein. Further, it has long been known that the cleavage specificity of a secreted protein is ultimately determined by the primary structure of the complete protein, that is, it is inherent in the amino acid sequence of the polypeptide. Therefore, the present invention provides a nucleotide sequence encoding the mature PTH1R polypeptides having the amino acid sequence encoded by the cDNA clone deposited in a bacterial host with the ATCC as patent deposit PTA-916 on Nov. 4, 1999 and as shown in FIG. 2A (SEQ ID NO:2). The present invention also provides a nucleotide sequence encoding the mature PTH3R polypeptides having the amino acid sequence encoded by the cDNA clone deposited in a bacterial host with the ATCC as patent deposit PTA-915 on Nov. 4, 1999 and as shown in FIG. 2B (SEQ ID NO:4). By the mature PTH1R protein having the amino acid sequence encoded by the cDNA clone contained in the bacterial host deposited with the ATCC as patent deposit PTA-916 is meant the mature form(s) of the PTH1R receptor produced by expression in a mammalian cell (e.g., COS cells, as described below) of the complete open reading frame encoded by the zebrafish DNA sequence of the clone contained in the vector in the deposited host. By the mature PTH3R protein having the amino acid sequence encoded by the cDNA clone contained in the bacterial host deposited with the ATCC as patent deposit PTA-915 is meant the mature form(s) of the PTH3R receptor produced by expression in a mammalian cell (e.g., COS cells, as described below) of the complete open reading frame encoded by the zebrafish DNA sequence of the clone contained in the vector in the deposited host. As indicated below, the mature PTH1R receptor having the amino acid sequence encoded by the cDNA clone deposited with the ATCC as patent deposit PTA-916 may or may not differ from the predicted "mature" PTH1R protein shown in FIG. 2A (amino acids from about 25 to about 536) depending on the accuracy of the predicted cleavage. The mature PTH3R receptor having the amino acid sequence encoded by the cDNA clone deposited with the ATCC as patent deposit PTA-915 may or may not differ from the predicted "mature" PTH3R protein shown in FIG. 2B (amino acids from about 22 to about 542) depending on the accuracy of the predicted cleavage site.

Methods for predicting whether a protein has a secretory leader as well as the cleavage point for that leader sequence are available. For instance, the methods of McGeoch (*Virus Res.* 3:271–286 (1985)) and von Heinje (*Nucleic Acids Res.* 14:4683–4690 (1986)) can be used. The accuracy of predicting the cleavage points of known mammalian secretory proteins for each of these methods is in the range of 75–80%, von Heinje, supra. However, the two methods do not always produce the same predicted cleavage point(s) for a given protein. A computational method may be found in the computer program "PSORT" (K. Nakai and M. Kanehisa, *Genomics* 14:897–911 (1992)), which is an expert system for predicting the cellular location of a protein based on the amino acid sequence. As part of this computational prediction of localization, the methods of McGeoch and von Heinje are incorporated.

In the present case, the predicted amino acid sequence of the complete PTH1R and PTH3R polypeptides of the present invention were analyzed for structural properties by comparison to the rat PTH1R sequence. This analysis provided predicted a cleavage site between amino acids 24 and 25 in FIG. 2A (SEQ ID NO:2) and a cleavage site between amino acids 21 and 22 in FIG. 2B (SEQ ID NO:4). Thus, the leader sequence for the PTH1R receptor protein is predicted to consist of amino acid residues 1–24 in FIG. 2A (amino acids 1 to 24 in SEQ ID NO:2), while the predicted mature PTH1R protein consists of residues 25–536 (amino acids 25 to 536 in SEQ ID NO:2). The leader sequence for the PTH3R receptor protein is predicted to consist of amino acid residues 1–21 in FIG. 2B (amino acids 1–21 in SEQ ID NO:4), while the predicted mature PTH3R protein consists of residues 22–542 (amino acids 22 to 542 in SEQ ID NO:4).

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

As one of ordinary skill would appreciate, however, due to the possibilities of sequencing errors, the PTH 1 R receptor polypeptide encoded by the deposited cDNA comprises about 536 amino acids, but may be anywhere in the range of 510–561 amino acids; and the leader sequence of this protein is about 24 amino acids, but may be anywhere in the range of about 10 to about 30 amino acids. As one of ordinary skill would also appreciate, however, due to the possibilities of sequencing errors, the PTH3R receptor polypeptide encoded by the deposited cDNA comprises about 542 amino acids, but may be anywhere in the range of 500–550 amino acids; and the leader sequence of this protein is about 24 amino acids, but may be anywhere in the range of about 15 to about 35 amino acids.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) shown in FIG. 1C (SEQ ID NO:1) or FIG. 1D (SEQ ID NO:3); DNA molecules comprising the coding sequence for the PTH1R receptor shown in FIG. 2A (SEQ ID NO:2) or the PTH3R receptor shown FIG. 2B (SEQ ID NO:4); and DNA molecules which comprise a sequence substantially different from those described above but which, due to the degeneracy of the genetic code, still encode the PTH1R or the PTH3R receptor. Of course, the genetic code is well known in the art. Thus, it would be routine for one skilled in the art to generate such degenerate variants.

In another aspect, the invention provides isolated nucleic acid molecules encoding the PTH1R polypeptide having an amino acid sequence encoded by the cDNA clone contained in the plasmid deposited with the ATCC as patent deposit PTA-916 on Nov. 4, 1999. Another aspect, the invention provides isolated nucleic acid molecules encoding the PTH3R polypeptide having an amino acid sequence encoded by the cDNA clone contained in the plasmid deposited with the ATCC as patent deposit PTA-915 on Nov. 4, 1999. Preferably, these nucleic acid molecules will encode the mature polypeptides encoded by the above-described deposited cDNA clones. In a further embodiment, nucleic acid molecules are provided encoding the PTH1R or the PTH3R polypeptide or the PTH1R or the PTH3R polypeptide lacking the N-terminal methionine. The invention also provides an isolated nucleic acid molecule having the nucleotide sequence shown in SEQ ID NO:1 or the nucleotide sequence of the PTH1R cDNA contained in the above-described deposited clone, or a nucleic acid molecule having a sequence complementary to one of the above sequences. Such isolated molecules, particularly DNA molecules, are useful as probes for gene mapping, by in situ hybridization with chromosomes, and for detecting expression of the PTH1R gene in human tissue, for instance, by Northern blot analysis. The invention also provides an isolated nucleic acid molecule having the nucleotide sequence shown in SEQ ID NO:3 or the nucleotide sequence of the cDNA contained in the above-described deposited clone, or a nucleic acid molecule having a sequence complementary to one of the above sequences. Such isolated molecules, particularly DNA molecules, are useful as probes for gene mapping, by in situ hybridization with chromosomes, and for detecting expression of the gene in human tissue, for instance, by Northern blot analysis.

The present invention is further directed to fragments of the isolated nucleic acid molecules described herein. By a fragment of an isolated nucleic acid molecule having the nucleotide sequence of the deposited cDNAs or the nucleotide sequence shown in FIG. 1C (SEQ ID NO:1) or FIG. 1D (SEQ ID NO:3) is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments of about 50–1550 nt in length, and more preferably at fragments least about 600 nt in length are also useful according to the present invention as are fragments corresponding to most, if not all, of the nucleotide sequence of the deposited cDNAs or as shown in FIG. 1C (SEQ ID NO:1) or FIG. 1D (SEQ ID NO:3). By a fragment at least 20 nt in length, for example, is intended fragments which include 20 or more contiguous bases from the nucleotide sequence of the deposited cDNAs or the nucleotide sequence as shown in FIG. 1C (SEQ ID NO: 1) or FIG. 1D (SEQ ID NO:3).

Preferred nucleic acid fragments of the present invention include nucleic acid molecules encoding: a polypeptide comprising the PTH1R receptor extracellular domain (predicted to constitute amino acid residues from about 25 to about 147 in FIG. 2A (or amino acid residues from about 25 to about 147 in SEQ ID NO:2)); a polypeptide comprising the PTH1R receptor transmembrane domain (predicted to constitute amino acid residues from about 148 to about 416 in FIG. 2A (or amino acid residues from about 148 to about 416 in SEQ ID NO:2)); and a polypeptide comprising the PTH1R receptor extracellular domain with all or part of the transmembrane domain deleted. As above with the leader sequence, the amino acid residues constituting the PTH1R receptor extracellular and transmembrane domains have been predicted. Thus, as one of ordinary skill would appreciate, the amino acid residues constituting these domains may vary slightly (e.g., by about 1 to about 15 amino acid residues) depending on the criteria used to define each domain.

Preferred nucleic acid fragments of the present invention also include nucleic acid molecules encoding: a polypeptide comprising the PTH3R receptor extracellular domain (predicted to constitute amino acid residues from about 22 to about 145 in FIG. 2B (or amino acid residues from about 22 to about 145 in SEQ ID NO:4)); a polypeptide comprising the PTH3R receptor transmembrane domain (predicted to constitute amino acid residues from about 146 to about 402 in FIG. 2B (or amino acid residues from about 146 to about 402 in SEQ ID NO:4); and a polypeptide comprising the PTH3R receptor extracellular domain with all or part of the transmembrane domain deleted. As above with the leader sequence, the amino acid residues constituting the PTH3R receptor extracellular and transmembrane domains have been predicted by computer analysis. Thus, as one of ordinary skill would appreciate, the amino acid residues constituting these domains may vary slightly (e.g., by about 1 to about 15 amino acid residues) depending on the criteria used to define each domain.

Preferred nucleic acid fragments of the present invention also include nucleic acid molecules encoding epitope-bearing portions of the PTH1R or PTH3R receptor protein. As one skilled in the art would know, a nucleic acid sequence may be used to predict the polypeptide sequence encoded therein. Such information may then be used to predict antigenic determinants in the polypeptide that may be related to the corresponding polynucleotide regions encoding the antigenic determinants identified by the analysis. Methods for predicting the antigenic determinants of a polypeptide are well known in the art.

Methods for determining other such epitope-bearing portions of the PTH1R or the PTH3R protein are described in detail below.

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clones contained in the bacterial hosts deposited with the ATCC as patent deposit PTA-915 or patent deposit PTA-916. By "stringent hybridization conditions" is intended overnight incubation at 42° C. in a solution comprising: 50% formamide, 5×SSC (150 mM NaCl, 15 mM trisodium citrate), 50 mM sodium phosphate (pH 7.6),5×Denhardt's solution, 10% dextran sulfate, and 20 g/ml denatured, sheared salmon sperm DNA, followed by washing the filters in 0.1×SSC at about 65° C.

In another aspect, the invention provides an isolated nucleic acid molecule comprising a polynucleotide which hybridizes under low stringency hybridization conditions to a portion of the polynucleotide in a nucleic acid molecule of the invention described above, for instance, the cDNA clones contained in the bacterial hosts deposited with the ATCC as patent deposit PTA-915 or patent deposit PTA-916. By "low stringency hybridization conditions" is intended overnight incubation at 42° C. in a solution comprising: 30% formamide, 5×SSC (150 mM NaCl, 15 mM trisodium citrate), 50 mM sodium phosphate (pH 7.6), 5×Denhardt's solution, 10% dextran sulfate, and 20 g/ml denatured, sheared salmon sperm DNA, followed by washing the filters in a solution of 2×SSC or 1×SSC or 0.5×SSC at about 55° C. or 60° C. or 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotide (e.g., the deposited cDNAs or the nucleotide sequence as shown in FIG. 1C (SEQ ID NO:1) or FIG. 1D (SEQ ID NO:3).

Of course, a polynucleotide which hybridizes only to a poly A sequence (such as the 3' terminal poly(A) tract of the PTH1R receptor cDNA shown in FIG. 1C (SEQ ID NO:1) or the 3' terminal poly(A) tract of the PTH3R receptor cDNA shown in FIG. 1D (SEQ ID NO:3)), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention which encode a PTH1R or PTH3R polypeptide may include, but are not limited to those encoding the amino acid sequence of the mature polypeptides, by themselves; the coding sequence for the mature polypeptides and additional sequences, such as those encoding the amino acid leader or secretory sequence, such as a pre-, or pro- or prepro-protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities. Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are commercially available. As described in Gentz et al., Proc. Natl. Acad. Sci. USA 86:821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., Cell 37: 767 (1984). As discussed below, other such fusion proteins include the PTH1R receptor fused to Fc at the N- or C-terminus.

The present invention further relates to variants of the nucleic acid molecules of the present invention, which encode portions, analogs or derivatives of the PTH1R or PTH3R receptor. Variants may occur naturally, such as a natural allelic variant. By an "allelic variant" is intended one of several alternate forms of a gene occupying a given locus on a chromosome of an organism. Genes II, Lewin, B., ed., John Wiley & Sons, New York (1985). Non-naturally occurring variants may be produced using art-known mutagenesis techniques.

Such variants include those produced by nucleotide substitutions, deletions or additions, which may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the PTH1R or PTH3R receptor or portions thereof. Also especially preferred in this regard are conservative substitutions.

Further embodiments of the invention include isolated nucleic acid molecules comprising a polynucleotide having a nucleotide sequence at least 50%, 55%,60%, 65%,70%, 75%,80%, 85%,90%, 91%, 92%, 93%,94%,95%,96%, 97%, 98%, or 99% identical to (a) a nucleotide sequence encoding the full-length PTH1R polypeptide having the complete amino acid sequence in SEQ ID NO:2, including the predicted leader sequence; (b) a nucleotide sequence encoding the polypeptide having the amino acid sequence in SEQ ID NO:2, but lacking the N-terminal methionine; (c) a nucleotide sequence encoding the mature PTH1R receptor (full-length polypeptide with the leader removed) having the amino acid sequence at positions from about 25 to about 536 in SEQ ID NO:2; (d) a nucleotide sequence encoding the full-length PTH1R polypeptide having the complete amino acid sequence including the leader encoded by the cDNA clone deposited with the ATCC as patent deposit PTA-916; (e) a nucleotide sequence encoding the mature PTH1R receptor having the amino acid sequence encoded by the cDNA clone deposited with the ATCC as patent deposit PTA-916; (f) a nucleotide sequence encoding the PTH1R receptor extracellular domain; (g) a nucleotide sequence encoding the PTH1R receptor transmembrane domain; (h) a nucleotide sequence encoding the PTH1R receptor extracellular domain with all or part of the transmembrane domain deleted; and (i) a nucleotide sequence complementary to any of the nucleotide sequences in (a), (b), (c), (d), (e), (f), (g) or (h).

Embodiments of the invention also include isolated nucleic acid molecules comprising a polynucleotide having a nucleotide sequence at least 50%, 55%, 60%, 65%,70%, 75%,80%,85%, 90%,91%,92%,93%, 94%,95%, 96%, 97%, 98%, or 99% identical to (a) a nucleotide sequence encoding the full-length PTH3R polypeptide having the complete amino acid sequence in FIG. 2B (SEQ ID NO:4), including the predicted leader sequence; (b) a nucleotide sequence encoding the polypeptide having the amino acid sequence in SEQ ID NO:4, but lacking the N-terminal methionine; (c) a nucleotide sequence encoding the mature PTH3R receptor (full-length polypeptide with the leader removed) having the amino acid sequence at positions from about 22 to about 542 in SEQ ID NO:4; (d) a nucleotide sequence encoding the full-length PTH3R polypeptide having the complete amino acid sequence including the leader encoded by the cDNA clone deposited with the ATCC as patent deposit PTA-915; (e) a nucleotide sequence encoding the mature PTH3R receptor having the amino acid sequence encoded by the cDNA deposited with the ATCC as patent deposit PTA-915; (f) a nucleotide sequence encoding the PTH3R receptor extracellular domain; (g) a nucleotide sequence encoding the PTH3R receptor transmembrane domain; (h) a nucleotide sequence encoding the PTH3R receptor extracellular domain with all or part of the transmembrane domain deleted; and (i) a nucleotide sequence complementary to any of the nucleotide sequences in (a), (b), (c), (d), (e), (f), (g), or (h).

By a polynucleotide having a nucleotide sequence at least, for example, 95% "identical" to a reference nucleotide sequence encoding a PTH1R or PTH3R polypeptide is intended that the nucleotide sequence of the polynucleotide is identical to the reference sequence except that the polynucleotide sequence may include up to five point mutations per each 100 nucleotides of the reference nucleotide sequence encoding the PTH1R or PTH3R receptor. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 50%, 55%, 60%, 65%,70%, 75%, 80%, 85%,90%, 91%, 92%, 93%, 94%, 95%, 96%, 97%, 98%, or 99% identical to, for instance, the nucleotide sequence shown in FIG. 1C or 1D or to the nucleotides sequence of the deposited cDNA clones can be determined conventionally using known computer programs such as the Bestfit program (Wisconsin Sequence Analysis Package, Version 8 for Unix, Genetics Computer Group, University Research Park, 575 Science Drive, Madison, Wis. 53711. Bestfit uses the local homology algorithm of Smith and Waterman, Advances in Applied Mathematics 2: 482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 50%, 55%, 60%, 65%, 70%, 75%, 80%, 85%, 90%, 91%, 92%, 93%, 94%, 95%, 96%, 97%, 98%, or 99% identical to the nucleic acid sequence shown in FIG. 1C (SEQ ID NO:1) or FIG. 1D (SEQ ID NO:3) or to the nucleic acid sequence of the deposited cDNAs, irrespective of whether they encode a polypeptide having PTH1R or PTH3R receptor activity. This is because even where a particular nucleic acid molecule does not encode a polypeptide having PTH1R or PTH3R receptor activity, one of skill in the art would still know how to use the nucleic acid molecule, for instance, as a hybridization probe or a polymerase chain reaction (PCR) primer. Uses of the nucleic acid molecules of the present invention that do not encode a polypeptide having PTH1R or PTH3R receptor activity include, inter alia, (1) isolating the PTH1R or PTH3R receptor gene or allelic variants thereof in a cDNA library; (2) in situ hybridization (e.g., "FISH") to metaphase chromosomal spreads to provide precise chromosomal location of the PTH1R or PTH3R receptor gene, as described in Verma et al., *Human Chromosomes: A Manual of Basic Techniques*, Pergamon Press, New York (1988); and (3) Northern Blot analysis for detecting PTH1R or PTH3R receptor mRNA expression in specific tissues.

Preferred, however, are nucleic acid molecules having sequences at least 50%, 55%, 60%, 65%, 70%, 75%, 80%, 85%, 90%, 91%, 92%, 93%, 94%, 95%, 96%, 97%, 98%, or 99% identical to the nucleic acid sequence shown in FIG. 1C (SEQ ID NO:1) or FIG. 1D (SEQ ID NO:3) or to the nucleic acid sequence of the deposited cDNA which do, in fact, encode a polypeptide having PTH1R or PTH3R receptor activity. By "a polypeptide having PTH1R or PTH3R receptor activity" is intended polypeptides exhibiting activity similar, but not necessarily identical, to an activity of the PTH1R or PTH3R receptor of the invention, as measured in a particular biological assay. For example, PTH1R or PTH3R receptor activity can be measured using competition binding experiments of labeled PTH or PTHrP to cells expressing the candidate PTH1R or PTH3R polypeptide as described in Treanor et al., *Nature* 382:80–83 (1996) or Jing et al., *Cell* 85: 1113–1124 (1996).

As demonstrated in Examples 3 and 4 herein, assays to address PTH1R and PTH3R function are well known in the art. Any cell line expressing the PTH1R or PTH3R receptor, or variants thereof, may be used to assay ligand binding and second messenger activation as described in Examples 3 and 4. Of course, due to the degeneracy of the genetic code, one of ordinary skill in the art will immediately recognize that a large number of the nucleic acid molecules having a sequence at least 95%, 96%, 97%, 98%, or 99% identical to the nucleic acid sequence of the deposited cDNAs or the nucleic acid sequence shown in FIG. 1C (SEQ ID NO:1) or FIG. 1D (SEQ ID NO:3) will encode a polypeptide "having PTH1R or PTH3R receptor activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having PTH1R or PTH3R protein activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U. et al., "Deciphering the Message in Protein Sequences: Tolerance to Amino Acid Substitutions," *Science* 247:1306–1310 (1990), wherein the authors indicate that proteins are surprisingly tolerant of amino acid substitutions.

The invention also provides a method for the isolation of a nucleic acid molecule comprising: (a) selecting a fragment of SEQ ID NO:3 as a nucleic acid probe; (b) hybridizing said probe overnight to at least one test sequence by incubation at 42° C. in a solution of 30% formamide, 5×SSC (150 mM NaCl, 15 mM trisodium citrate), 50 mM sodium phosphate (pH 7.6), 5×Denhardt's solution, 10% dextran sulfate, and 20 g/ml denatured, sheared salmon sperm DNA; (c) removing nonhydridized probe by washing with a solution of 2×SSC or 1×SSC or 0.5×SSC at about 55° C. or 60° C. or 65° C.; and (d) identifying a target sequence bound by said probe; wherein said identified target sequence is at least about 50%, 55%, 60%, 65%, 70%, 75%, 80%, 85%, 90%, 91%, 92%, 93%, 94%, 95%, 96%, 97%, 98%, or 99% identical to a sequence selected from the group consisting of: (e) a nucleotide sequence encoding the PTH3R receptor having the complete amino acid sequence at positions from about 1 to about 542 in (SEQ ID NO:4); (f) a nucleotide sequence encoding the PTH3R receptor having the amino acid sequence at positions from about 2 to about 542 in (SEQ ID NO:4); (g) a nucleotide sequence encoding the mature PTH3R receptor having the amino acid sequence at positions from about 22 to about 542 in (SEQ ID NO:4); (h) a nucleotide sequence encoding the PTH3R receptor having the complete amino acid sequence encoded by the cDNA clone deposited with the ATCC as patent deposit PTA-915; (i) a nucleotide sequence encoding the mature PTH3R receptor having the amino acid sequence encoded by the cDNA clone deposited with the ATCC as patent deposit PTA-915; (j) a nucleotide sequence encoding the PTH3R extracellular domain; (k) a nucleotide sequence encoding the PTH3R transmembrane domain; and (l) a nucleotide sequence complementary to any of the nucleotide sequences in (e), (f), (g), (h), (i), (j) or (k).

The invention also provides a method for the isolation of a nucleic acid molecule comprising: (a) selecting a fragment of SEQ ID NO:1 as a nucleic acid probe; (b) hybridizing said probe overnight to at least one test sequence by incubation at 42° C. in a solution of 30% formamide, 5×SSC (150 mM NaCl, 15 mM trisodium citrate), 50 mM sodium phosphate (pH 7.6), 5×Denhardt's solution, 10% dextran sulfate, and 20 g/ml denatured, sheared salmon sperm DNA; (c) removing nonhydridized probe by washing with a solution of 2×SSC or 1×SSC or 0.5×SSC at about 55° C. or 60° C. or 65° C.; and (d) identifying a target sequence bound by said probe; wherein said identified target sequence is at least about 50%, 55%, 60%, 65%, 70%, 75%, 80%, 85%, 90%, 91%, 92%, 93%, 94%, 95%, 96%, 97%, 98%, or 99% identical to a sequence selected from the group consisting of: (e) a nucleotide sequence encoding the PTH1R receptor having the complete amino acid sequence at positions from about 1 to about 536 in SEQ ID NO:2; (f) a nucleotide sequence encoding the PTH1R receptor having the amino acid sequence at positions from about 2 to about 536 in SEQ ID NO:2; (g) a nucleotide sequence encoding the mature PTH1R receptor having the amino acid sequence at positions from about 25 to about 536 in SEQ ID NO:2; (h) a nucleotide sequence encoding the PTH1R receptor having the complete amino acid sequence encoded by the cDNA clone deposited with the ATCC as patent deposit PTA-916; (i) a nucleotide sequence encoding the mature PTH1R receptor having the amino acid sequence encoded by the cDNA deposited with the ATCC as patent deposit PTA-916; (j) a nucleotide sequence encoding the PTH1R extracellular domain; (k) a nucleotide sequence encoding the PTH1R transmembrane domain; and (l) a nucleotide sequence complementary to any of the nucleotide sequences in (e), (f), (g), (h), (i), (j) or (k).

Vectors and Host Cells

The present invention also relates to vectors which include the isolated DNA molecules of the present invention, host cells which are genetically engineered with the recombinant vectors, and the production of PTH1R or PTH3R polypeptides or fragments thereof by recombinant techniques.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the *E. coli lac, trp* and *tac* promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in *E. coli* and other bacteria. Representative examples of appropriate hosts include, but are not limited to, bacterial cells, such as *E. coli, Streptomyces* and *Salmonella typhimurium* cells; fungal cells, such as yeast cells; insect cells such as *Drosophila* S2 and *Spodoptera* Sf9 cells; animal cells such as CHO, COS and Bowes melanoma cells; and plant cells. Appropriate culture mediums and conditions for the above-described host cells are known in the art.

Among vectors preferred for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fe portion proves to be a hindrance to use in therapy and diagnosis, for example when the fusion protein is to be used as antigen for immunizations. In drug discovery, for example, human proteins, such as, hIL5-receptor has been fused with Fe portions for the purpose of high-throughput screening assays to identify antagonists of hIL-5. See, D. Bennett et al., *Journal of Molecular Recognition*, Vol. 8:52–58 (1995) and K. Johanson et al., *The Journal of Biological Chemistry*, Vol. 270, No. 16:9459–9471 (1995).

The PTH1R or PTH3R receptor can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

PTH1R and PTH3R Polypeptides and Fragments

The invention further provides an isolated PTH1R or PTH3R polypeptide having the amino acid sequence encoded by the deposited cDNAs, or the amino acid sequence in FIG. 2A (SEQ ID NO:2) or FIG. 2B (SEQ ID NO:4), or a peptide or polypeptide comprising a portion of the above polypeptides.

It will be recognized in the art that some amino acid sequences of the PTH1R or PTH3R receptor can be varied without significant effect of the structure or function of the protein. If such differences in sequence are contemplated, it should be remembered that there will be critical areas on the protein which determine activity. Thus, the invention further includes variations of the PTH1R or PTH3R receptor which show substantial PTH1R or PTH3R receptor activity or which include regions of PTH1R or PTH3R protein such as the protein portions discussed below. Such mutants include deletions, insertions, inversions, repeats, and type substitutions. As indicated above, guidance concerning which amino acid changes are likely to be phenotypically silent can be found in Bowie, J. U., et al., "Deciphering the Message in Protein Sequences: Tolerance to Amino Acid Substitutions," *Science* 247:1306–1310 (1990).

Thus, the fragment, derivative or analog of the polypeptide of FIG. 2A (SEQ ID NO:2) or FIG. 2B (SEQ ID NO:4), or that encoded by the deposited cDNAs, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the PTH1R or PTH3R protein. The prevention of aggregation is highly desirable. Aggregation of proteins not only results in a loss of activity but can also be problematic when preparing pharmaceutical formulations, because they can be immunogenic. (Pinckard et al., *Clin Exp. Immunol.* 2:331–340(1967); Robbins et al., *Diabetes* 36:838–845 (1987); Cleland et al. *Crit. Rev. Therapeutic Drug Carrier Systems* 10:307–377 (1993)).

The replacement of amino acids can also change the selectivity of binding to cell surface receptors. Ostade et al., *Nature* 361:266–268 (1993) describes certain mutations resulting in selective binding of TNF-α to only one of the two known types of TNF receptors. Thus, the PTH1R or PTH3R receptor of the present invention may include one or more amino acid substitutions, deletions or additions, either from natural mutations or human manipulation.

As indicated, changes are preferably of a minor nature, such as conservative amino acid substitutions that do not significantly affect the folding or activity of the protein (see Table 1).

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Amino acids in the PTH1R or PTH3R protein of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as receptor binding or in vitro proliferative activity. Sites that are critical for ligand-receptor binding can also be determined by structural analysis such as crystallization, nuclear magnetic resonance or photoaffinity labeling (Smith et al., *J. Mol. Biol.* 224: 899–904 (1992) and de Vos et al. *Science* 255:306–312 (1992)).

The polypeptides of the present invention are preferably provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell. For example, a recombinantly produced version of the antimicrobial peptide polypeptide can be substantially purified by the one-step method described in Smith and Johnson, *Gene* 67:31–40 (1988).

The polypeptides of the present invention are preferably provided in an isolated form, and preferably are substantially purified. A recombinantly produced version of the PTH1R or PTH3R receptor can be substantially purified by the one-step method described in Smith and Johnson, *Gene* 67:31–40 (1988).

The polypeptides of the present invention also include the polypeptide encoded by the deposited PTH1R cDNA including the leader, the polypeptide encoded by the deposited the cDNA minus the leader (i.e., the mature protein), the polypeptide of FIG. 2A (SEQ ID NO:2) including the leader, the polypeptide of FIG. 2A (SEQ ID NO:2) minus the leader, the extracellular domain, the transmembrane domain, a polypeptide comprising amino acids about 1 to about 536 in SEQ ID NO:2, and a polypeptide comprising amino acids about 2 to about 536 in SEQ ID NO:2, as well as polypeptides which are at least 95% identical, still more preferably at least 96%, 97%, 98% or 99% identical to the polypeptides described above, and also include portions of such polypeptides with at least 30 amino acids and more preferably at least 50 amino acids.

The polypeptides of the present invention also include the polypeptide encoded by the deposited PTH3R cDNA including the leader, the polypeptide encoded by the deposited the cDNA minus the leader (i.e., the mature protein), the polypeptide of FIG. 2 (SEQ ID NO:4) including the leader, the polypeptide of FIG. 4 (SEQ ID NO:4) minus the leader, the extracellular domain, the transmembrane domain, a polypeptide comprising amino acids about 1 to about 542 in SEQ ID NO:4, and a polypeptide comprising amino acids about 2 to about 542 in SEQ ID NO:4, as well as polypeptides which are at least 95% identical, still more preferably at least 96%, 97%, 98% or 99% identical to the polypeptides described above, and also include portions of such polypeptides with at least 30 amino acids and more preferably at least 50 amino acids.

By a polypeptide having an amino acid sequence at least, for example, 95% "identical" to a reference amino acid sequence of a PTH1R or PTH3R polypeptide is intended that the amino acid sequence of the polypeptide is identical to the reference sequence except that the polypeptide sequence may include up to five amino acid alterations per each 100 amino acids of the reference amino acid of the PTH1R or PTH3R receptor. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 50%, 55%, 60%, 65%, 70%, 75%, 80%, 85%, 90%, 91%, 92%, 93%, 94%, 95%, 96%, 97%, 98%, or 99% identical to, for instance, the amino acid sequence shown in FIG. 2A (SEQ ID NO:2) or FIG. 2B (SEQ ID NO:4) or to the amino acid sequence encoded by deposited cDNA clones can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

The polypeptide of the present invention could be used as a molecular weight marker on SDS-PAGE gels or on molecular sieve gel filtration columns using methods well known to those of skill in the art.

As described in detail below, the polypeptides of the present invention can also be used to raise polyclonal and monoclonal antibodies, which are useful in assays for detecting PTH1R or PTH3R expression as described below or as agonists and antagonists capable of enhancing or inhibiting PTH1R or PTH3R receptor function. Further, such polypeptides can be used in the yeast two-hybrid system to "capture" PTH1R or PTH3R receptor binding proteins which are also candidate agonist and antagonist according to the present invention. The yeast two hybrid system is described in Fields and Song, *Nature* 340:245–246 (1989).

In another aspect, the invention provides a peptide or polypeptide comprising an epitope-bearing portion of a polypeptide of the invention. The epitope of this polypeptide portion is an immunogenic or antigenic epitope of a polypeptide described herein. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad. Sci. USA* 81:3998–4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) Antibodies that react with predetermined sites on proteins. *Science* 219:660–666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals.

Antigenic epitope-bearing peptides and polypeptides of the invention are therefore useful to raise antibodies, including monoclonal antibodies, that bind specifically to a polypeptide of the invention. See, for instance, Wilson et al., *Cell* 37:767–778 (1984) at 777. Antigenic epitope-bearing peptides and polypeptides of the invention preferably contain a sequence of at least seven, more preferably at least nine and most preferably between at least about 15 to about 30 amino acids contained within the amino acid sequence of a polypeptide of the invention.

Thus, one skilled in the art will have the requisite knowledge to select antigenic epitope bearing regions from the polypeptides in FIG. 2A (SEQ ID NO:2) and FIG. 2B (SEQ ID NO:4).

The epitope-bearing peptides and polypeptides of the invention may be produced by any conventional means. For example, Houghten provides a general method for the rapid solid-phase synthesis of large numbers of peptides: specificity of antigen-antibody interaction at the level of individual amino acids Houghten, R. A., *Proc. Natl. Acad. Sci. USA* 82:5131–5135 (1985)). This "Simultaneous Multiple Peptide Synthesis (SMPS)" process is further described in U.S. Pat. No. 4,631,211 to Houghten et al. (1986).

As one of skill in the art will appreciate, PTH1R or PTH3R polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., *Nature* 331: 84–86 (1988)). Fusion proteins that have a disulfide-linked dimeric structure due to the IgG part can also be more efficient in binding and neutralizing other molecules than the monomeric PTH1R or PTH3R protein or protein fragment alone (Fountoulakis et al., *J. Biochem* 270:3958–3964 (1995)).

Diagnosis and Prognosis

It is believed that certain tissues in mammals with certain diseases and disorders express significantly decreased levels of the PTH1R or PTH3R receptor and mRNA encoding the PTH1R or PTH3R receptor when compared to a corresponding "standard" mammal, i.e., a mammal of the same species not having the disorder. Further, it is believed that enhanced levels of the PTH1R or PTH3R receptor can be detected in certain body fluids (e.g., sera, plasma, urine, and spinal fluid) from mammals with cancer when compared to sera from mammals of the same species not having the disorder. Thus, the invention provides a diagnostic method useful during diagnosis of diseases and disorders, for example, which involves assaying the expression level of the gene encoding the PTH1R or PTH3R receptor in mammalian cells or body fluid and comparing the gene expression level with a standard PTH1R or PTH3R receptor gene expression level, whereby an decrease in the gene expression level over the standard is indicative of certain disorders.

Where a diagnosis of a disorder has already been made according to conventional methods, the present invention is useful as a prognostic indicator, whereby patients exhibiting decreased PTH1R or PTH3R gene expression will experience a worse clinical outcome relative to patients expressing the gene at a higher level.

By "assaying the expression level of the gene encoding the PTH1R or PTH3R protein" is intended qualitatively or quantitatively measuring or estimating the level of the PTH1R or PTH3R protein or the level of the mRNA encoding the PTH1R or PTH3R receptor in a first biological sample either directly (e.g., by determining or estimating absolute protein level or mRNA level) or relatively (e.g., by comparing to the PTH1R or PTH3R protein level or mRNA level in a second biological sample).

Preferably, the PTH1R or PTH3R protein level or mRNA level in the first biological sample is measured or estimated and compared to a standard PTH1R or PTH3R protein level or mRNA level, the standard being taken from a second biological sample obtained from an individual not having the cancer. As will be appreciated in the art, once a standard PTH1R or PTH3R protein level or mRNA level is known, it can be used repeatedly as a standard for comparison.

By "biological sample" is intended any biological sample obtained from an individual, cell line, tissue culture, or other source which contains PTH1R or PTH3R protein or mRNA. Biological samples include mammalian body fluids (such as sera, plasma, urine, synovial fluid and spinal fluid) which contain PTH1R or PTH3R protein, and ovarian, prostate, heart, placenta, pancreas liver, spleen, lung, breast, neural, and umbilical tissue.

The present invention is useful for detecting disorders in mammals. In particular the invention is useful during diagnosis of diseases and disorders in mammals involving PTH1R or PTH3R receptor expression or function. Mutations that affect PTH1R or PTH3R sequence and/or expression levels of PTH1R or PTH3R could be diagnostic for patients with diseases or disorders of a developmental, physiological or neurological nature. Preferred mammals include monkeys, apes, cats, dogs, cows, pigs, horses, rabbits and humans. Particularly preferred are humans.

Total cellular RNA can be isolated from a biological sample using the single-step guanidinium-thiocyanate-phenol-chloroform method described in Chomczynski and Sacchi, *Anal. Biochem.* 162:156–159(1987). Levels of mRNA encoding the PTH1R or PTH3R receptor are then assayed using any appropriate method. These include Northern blot analysis (Harada et al., *Cell* 63:303–312 (1990)), S1 nuclease mapping (Fujita et al., *Cell* 49:357–367 (1987)), the polymerase chain reaction (PCR), reverse transcription in combination with the polymerase chain reaction (RT-PCR) (Fujita et al., *Cell* 49:357–367(1987)), and reverse transcription in combination with the ligase chain reaction (RT-LCR).

Assaying PTH1R or PTH3R protein levels in a biological sample can occur using antibody-based techniques. For example, PTH1R or PTH3R protein expression in tissues can be studied with classical immunohistological methods (Jalkanen, M., et al., *J. Cell. Biol.* 101:976–985 (1985); Jalkanen, M., et al., *J. Cell. Biol.* 105:3087–3096 (1987)). Other antibody-based methods useful for detecting PTH1R or PTH3R receptor gene expression include immunoassays, such as the enzyme linked immunosorbent assay (ELISA) and the radioimmunoassay (RIA).

Suitable labels are known in the art and include enzyme labels, such as glucose oxidase, and radioisotopes, such as iodine ($^{125}$I, $^{121}$I), carbon ($^{14}$C), sulfur ($^{35}$S), tritium ($^{3}$H), indium ($^{112}$In), and technetium ($^{99m}$Tc), and fluorescent labels, such as fluorescein and rhodamine, and biotin.

Agonists and Antagonists of the PTH1R or PTH3R

The present invention also provides a screening method for identifying compounds capable of enhancing or inhibiting a cellular response induced by the PTH1R or PTH3R receptor, which involves contacting cells which express the PTH1R or PTH3R receptor with the candidate compound, assaying a cellular response, and comparing the cellular response to a standard cellular response, the standard being assayed when contact is made in absence of the candidate compound; whereby, an increased cellular response over the standard indicates that the compound is an agonist and a decreased cellular response over the standard indicates that the compound is an antagonist.

In another aspect, a screening assay for agonists and antagonists is provided which involves determining the effect a candidate compound has on PTH or PTHrP binding to the PTH1R or PTH3R receptor. In particular, the method involves contacting the PTH1R or PTH3R receptor with a PTH or a PTHrP polypeptide and a candidate compound and determining whether PTH or PTHrP polypeptide binding to the PTH1R or PTH3R receptor is increased or decreased due to the presence of the candidate compound.

By "agonist" is intended naturally occurring and synthetic compounds capable of enhancing or potentiating PTH1R or PTH3R receptor response (e.g., signaling through the cAMP or inositol phosphate pathway). By "antagonist" is intended naturally occurring and synthetic compounds capable of inhibiting PTH1R or PTH3R receptor response (e.g., signaling through the cAMP or inositol phosphate pathway). Whether any candidate "agonist" or "antagonist" of the present invention can enhance or inhibit PTH1R or PTH3R receptor activity can be determined using art-known competition binding assays, including those described in more detail below.

One such screening procedure involves the use of melanophores which are transfected to express a receptor of the present invention. Such a screening technique is described in PCT WO 92/01810, published Feb. 6, 1992. Such an assay may be employed, for example, for screening for a compound which inhibits (or enhances) activation of the PTH1R or PTH3R receptor polypeptide of the present invention by contacting the melanophore cells which encode the receptor with both PTH or PTHrP as a ligand and the candidate antagonist (or agonist). Inhibition or enhancement of the signal generated by the ligand indicates that the compound is an antagonist or agonist of the ligand/receptor signaling pathway.

Other screening techniques include the use of cells which express the receptor (for example, transfected CHO cells) in a system which measures extracellular pH changes caused by receptor activation, for example, as described in *Science* 246:181–296 (October 1989). For example, compounds may be contacted with a cell which expresses the PTH1R or PTH3R receptor polypeptide of the present invention and a second messenger response, e.g., signal transduction or pH changes, may be measured to determine whether the potential compound activates or inhibits the receptor.

Another such screening technique involves introducing RNA encoding the PTH1R or PTH3R receptor into Xenopus oocytes to transiently express the receptor. The receptor oocytes may then be contacted with the receptor ligand and a compound to be screened, followed by detection of inhibition or activation of a calcium signal in the case of screening for compounds which are thought to inhibit activation of the receptor.

Another screening technique involves expressing in cells a construct wherein the receptor is linked to a phospholipase C or D. Such cells include endothelial cells, smooth muscle cells, embryonic kidney cells, etc. The screening 110 may be accomplished as hereinabove described by detecting activation of the PTH1R or PTH3R receptor or inhibition of activation of the PTH1R or PTH3R receptor from the phospholipase signal.

Another method involves screening for compounds which inhibit activation of the receptor polypeptide of the present invention antagonists by determining inhibition of binding of labeled ligand to cells which have the receptor on the surface thereof. Such a method involves transfecting a eukaryotic cell with DNA encoding the PTH1R or PTH3R receptor such that the cell expresses the receptor on its surface and contacting the cell with a compound in the presence of a labeled form of a known ligand. The ligand can be labeled, e.g., by radioactivity. The amount of labeled ligand bound to the receptors is measured, e.g., by measuring radioactivity of the receptors. If the compound binds to the receptor as determined by a reduction of labeled ligand which binds to the receptors, the binding of labeled ligand to the receptor is inhibited.

Further screening assays for agonist and antagonist of the present invention are described in Tartaglia, L. A., and Goeddel, D. V., *J. Biol. Chem.* 267(7):4304–4307(1992).

Thus, in a further aspect, a screening method is provided for determining whether a candidate agonist or antagonist is capable of enhancing or inhibiting a cellular response to PTH or PTHrP. The method involves contacting cells which express the PTH1R or PTH3R polypeptide with a candidate compound and the PTH or PTHrP ligand, assaying a cellular response, and comparing the cellular response to a standard cellular response, the standard being assayed when contact is made with the ligand in absence of the candidate compound, whereby an increased cellular response over the standard indicates that the candidate compound is an agonist of the ligand/receptor signaling pathway and a decreased cellular response compared to the standard indicates that the candidate compound is an antagonist of the ligand/receptor signaling pathway. By "assaying a cellular response" is intended qualitatively or quantitatively measuring a cellular response to a candidate compound and/or PTH or PTHrP (e.g., determining or estimating an increase or decrease in cell proliferation or tritiated thymidine labeling). By the invention, a cell expressing the PTH1R or PTH3R polypeptide can be contacted with either an endogenous or exogenously administered PTH or PTHrP.

Agonist according to the present invention include naturally occurring and synthetic compounds such as, for example, PTH or PTHrP peptide fragments, or other known compounds that behave as PTH or PTHrP agonist. Preferred agonist include chemotherapeutic drugs such as, for example, cisplatin, doxorubicin, bleomycin, cytosine arabinoside, nitrogen mustard, methotrexate and vincristine. Others include ethanol and β-amyloid peptide. (*Science* 267: 1457–1458 (1995)). Further preferred agonist include polyclonal and monoclonal antibodies raised against the PTH1R or PTH3R polypeptide, or a fragment thereof.

Antagonist according to the present invention include naturally occurring and synthetic compounds such as, for example, the CD40 ligand, neutral amino acids, zinc, estrogen, androgens, viral genes (such as Adenovirus E1B, Baculovirus p35 and JAP, Cowpox virus crmA, Epstein-Barr virus BHRF1, LMP-1, African swine fever virus LMW5-HL, and Herpesvirus yl 34.5), calpain inhibitors, cysteine protease inhibitors, and tumor promoters (such as PMA, Phenobarbital, and α-Hexachlorocyclohexane).

Other potential antagonists include antisense molecules. Antisense technology can be used to control gene expression through antisense DNA or RNA or through triple-helix formation. Antisense techniques are discussed, for example, in Okano, *J. Neurochem.* 56:560 (1991); *Oligodeoxynucleotides as Antisense Inhibitors of Gene Expression*, CRC Press, Boca Raton, Fla. (1988). Triple helix formation is discussed in, for instance Lee et al., *Nucleic Acids Research* 6:3073 (1979); Cooney et al., *Science* 241:456 (1988); and Dervan et al., *Science* 251:1360 (1991). The methods are based on binding of a polynucleotide to a complementary DNA or RNA.

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide. The oligonucleotides described above can also be delivered to cells such that the antisense RNA or DNA may be expressed in vivo to inhibit production of the receptor.

Further antagonist according to the present invention include soluble forms of PTH1R or PTH3R fragments that include the ligand binding domain from the extracellular region of the full length receptor. Such soluble forms of the receptor, which may be naturally occurring or synthetic, antagonize PTH1R or PTH3R mediated signaling by competing with the cell surface PTH1R or PTH3R for binding to PTH or PTHrP. These are preferably expressed as dimers or trimers, since these have been shown to be superior to monomeric forms of soluble receptor as antagonists, e.g., IgGFc-PTH1R or IgGFc-PTH3R receptor family fusions.

Modes of Administration

It will be appreciated that conditions caused by a decrease in the standard or normal level of PTH1R or PTH3R receptor activity in an individual, can be treated by administration of PTH1R or PTH3R protein. Thus, the invention further provides a method of treating an individual in need of an increased level of PTH1R or PTH3R receptor activity comprising administering to such an individual a pharmaceutical composition comprising an effective amount of an isolated PTH1R or PTH3R polypeptide of the invention, effective to increase the PTH1R or PTH3R receptor activity level in such an individual.

The invention also relates to a method of treating an individual in need of an increased level of PTH 1R or PTH3R receptor activity comprising administering to such an individual a pharmaceutical composition comprising an effective amount of an agonist for PTH1R or PTH3R. The invention further relates to a method of treating an individual in need of a decreased level of PTH1R or PTH3R receptor activity comprising administering to such an individual a pharmaceutical composition comprising an effective amount of an antagonist for PTH1R or PTH3R.

As a general proposition, the total pharmaceutically effective amount of PTH1R or PTH3R polypeptide or its agonists or antagonists administered parenterally per dose will be in the range of about 1 µg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the PTH1R or PTH3R polypeptide is typically administered at a dose rate of about 1 µg/kg/hour to about 50 µg/kg/hour, either by 1–4 injections per day or by continuous subcutaneous infusions, for example, using a mini-pump. An intravenous bag solution may also be employed.

Pharmaceutical compositions containing the PTH1R or PTH3R polypeptide(s)of the invention or its agonists or antagonsits may be administered orally, rectally, parenterally, intracisternally, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Chromosome Assays

The nucleic acid molecules of the present invention are also valuable for chromosome identification. The sequence is specifically targeted to and can hybridize with a particular location on an individual human chromosome. The mapping of DNAs to chromosomes according to the present invention is an important first step in correlating those sequences with genes associated with disease.

In certain preferred embodiments in this regard, the cDNA herein disclosed is used to clone genomic DNA of a PTH1R or PTH3R receptor gene. This can be accomplished using a variety of well known techniques and libraries, which generally are available commercially. The genomic DNA then is used for in situ chromosome mapping using well known techniques for this purpose. In addition, in some cases, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes.

Fluorescence in situ hybridization ("FISH") of a cDNA clone to a metaphase chromosomal spread can be used to provide a precise chromosomal location in one step. This technique can be used with probes from the cDNA as short as 50 or 60 bp. For a review of this technique, see Verma et al., *Human Chromosomes: A Manual Of Basic Techniques*, Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance In Man*, available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

Having generally described the invention, the same will be more readily understood by reference to the following examples, which are provided by way of illustration and are not intended as limiting.

EXAMPLES

Example 1

Isolation of Genomic DNA Clones Encoding the Zebrafish PTH1R and a novel type-3 receptor, PTH3R Using zebrafish genomic DNA and several degenerate forward and reverse primers (FIG. 1), two distinct products of approximately 200 and 840 bp, respectively were obtained under stringent conditions. Forward (For) and reverse (Rev) degenerate primers (synthesized by the MGH Polymer core facility) for nested PCR (nPCR) were based on previously isolated mammalian and frog PTH1R sequences. Primers were located in exon M6/7 which encodes in mammals the third extracellular loop and the amino-terminal portion of transmembrane (TM) helix 7, and exon M7 which encodes the carboxy-terminal portion of TM7 and the beginning of the intracellular tail (Kong, et al., (1994); Schipani, et al., (1995)) (FIG. 1).

The primers for the first PCR reaction were the following: For M6a (5'TTYGGIGTSCAYTAYATHGTVTT; (SEQ ID NO:26) 576-fold degenerate), or For M6b (5'GTSYTBRT-GCCICTHYTYGG; (SEQ ID NO:6) 1152-fold degenerate), and Rev M7 (CTCDCCATTRCAGWARCAGTADAT; (SEQ ID NO:7) 72-fold degenerate) (FIG. 1). PCR was performed using 1 mg of zebrafish (Danio rerio) genomic DNA, Gibco Taq (5 units), and the following PCR profile [initial denaturation at 95° for 3 min, (denature at 94° for 1 min, anneal at 50° for 1 min, and polymerize at 72° for 4 or 6 min) for 35 cycles] on an MJ research thermal cycler (Watertown, Mass.). nPCR was performed using 2 µl of a 1:100 dilution of the initial PCR product with a degenerate nested primer Rev M7#2 (5'GTADATRATDGM-MACAAARAADCC; (SEQ ID NO:8) 432-fold degenerate), and either For M6a or For M6b using the same PCR profile as before (FIG. 1). nPCR products were identified on a 1.5% agarose gel with ethidium bromide, and DNA species of approximately 210 bp and 850 bp were excised, spun through a spin column (Bio 101, La Jolla, Calif.), ethanol precipitated overnight [(1/10 vol of 3M sodium acetate was added, 2 vol of ethanol, 1 µl of glycogen (Pharmacia, Uppsala, Sweden)], and ligated into pGEM-T (Promega, Madison, Wis.). After transformation of competent DH5a *E. coli* cells (Gibco, Grand Island, N. Y.), plasmid DNA from single colonies was purified using standard protocols, and sequenced by $^{33}$P cycle sequencing (Amersham, Arlington Heights, Ill.) on an 8M urea 6% polyacrylamide field gradient gel (Rubin et al, 1998). The DNA sequences, from the nested PCRs using For M6a or For M6b, were analyzed by the GCG package program (GCG, Univ. WI) and subsequently refered to as zPTH1R(TM6/7)/GEM-T and zPTH3R(TM6/7)/GEM-T, respectively.

Nucleotide sequence analysis revealed that both clones showed significant homology at their 5' and 3' ends with the hPTH1R (78% and 73% identity, respectively). While clone #1, zPTH1R(TM6/7), contained 84 bp of intronic sequence (compared to 81 bp of the hPTH1R) (Schipani, et al., (1995)), clone #2, zPTH3R(TM6/7), contained an intron of more than 700 bp. These findings indicated that portions of two distinct genes had been isolated which both share higher homology with PTH1R than with PTH2R (64% and 70% identity, respectively).

Example 2

Isolation of Partial cDNA Clones Encoding zPTH1R and zPTH3R

Total RNA from adult zebrafish was isolated as previously described (Rubin et al., (1999)) and used as a template for RT-PCR (Gibco). For and Rev primers for RT-PCR were based on either zPTH1R or zPTH3R genomic DNA sequences corresponding to the mammalian exons M6/7 and M7, zPTH1R(TM6/7)/GEM-T and zPTH3R(TM6/7)/GEM-T, respectively (FIG. 1). Reverse transcription (RT) was performed using Superscript II RNAase H⁻ reverse transcriptase and 5 µg total RNA at 42° C. with zPTH1R/Rev 6(1) (5'GCATTTCATAATGCATCTGGATTTG) (SEQ ID NO:9), or zPTH3R/Rev 6(1) (5'CTGTGAAGAATTGAA-GAGCATCTC) (SEQ ID NO: 10), respectively. PCR, using the For 313 (5'ACMAACTACTAYTGGATYCTGGTG (SEQ ID NO:11); 8-fold degenerate) and either of the two Rev 6(1) primers was performed using Gibco Taq (5 units) and the following PCR profile [initial denaturation at 95° for 3 min, (denature at 94° for 1 min, anneal at 56° for 1 min, and polymerize at 72° for 2 min) for 35 cycles]. nPCR was performed using 2 µl of a 1:100 dilution from the initial zPTH1R or zPTH3R RT-PCR product, and either zPTH1R/Rev 6(2) (5'AGAAACTTCTGTGTAAGGCATCGC) (SEQ ID NO: 12) or zPTH3R/Rev 6(2) (5' AAGAGCCATGAA-CAGCATGTAATG) (SEQ ID NO:13), and the For 313 primer using the previous PCR profile except for 35 cycles.

zPTH1R and zPTH3R PCR products were identified on a 1.5% agarose gel with ethidium bromide, cDNA species of approximately 450 bp were cloned, as described above, into pGEM-T to yield zPTH1R(TM3/6)/pGEMT and zPTH3R(TM3/6)/pGEMT, respectively.

Example 3

Isolation of Full-Length cDNAs Encoding the zPTH1R

RT-PCR using For313 and primers specific for zPTH1R (TM6/7) produced a 450 bp cDNA, zPTH1R(TM3/6), corresponding to TM3 through TM6 of the mammalian PTH1R. Subsequently, 5 ' and 3 ' RACE reactions were performed to generate overlapping sequences, and a full-length zPTH1R clone was constructed using a unique MfeI endonuclease restriction site (FIG. 1).

5' and 3' RACE reactions (Gibco) were performed using total RNA, and primers based on zPTH1R(TM3/6)/pGEMT nucleotide sequence. RT for 5' RACE was performed, as described above, except that Rev 6(2) was used. The first 5 'RACE PCR was performed using Rev 6(3) (5'GAAGAC-TATGTAGTGAACACCGAA) (SEQ ID NO:14), Gibco Taq (2.5 units) and the following PCR profile [initial denaturation at 95° for 3 min, (denature at 94° for 1 min, anneal at 55° for 1 min, and polymerize at 720 for 2 min) for 7 cycles, followed by 28 cycles with annealing at 64°. The first nPCR was performed using 5 µl of a 1:100 dilution from the previous PCR, Rev TM5 primer (5'ATATTGTTGTCTGGT-GTCACATCT) (SEQ ID NO: 15), (KlenTaq, 5.0 units) (Clontech, Calif.), and the following PCR profile [initial denaturation at 95° for 3 min, [(denature at 94° for 1 min, anneal at 62° for 1 min, and polymerize at 72° for 2 min) for 35 cycles} with a final extension of 10 min at 72°]. A second nPCR was performed using 5 µl of a 1:100 dilution from the first nPCR, Rev 4×primer (5'CGCATTTGTTTCTC-GAAGTTTTGTTGC) (SEQ ID NO:16), Gibco Taq (5.0 units) and the same PCR profile as the first NPCR. The second nPCR products were purified as described above and ligated into pGEM-T EASY (Promega) to yield zPTH1R (5')/pGEMTeasy, for transformation of TOP 10 E. coli cells (Invitrogen).

For 3' RACE, RT was performed as before but with an oligo-dT anchor primer (Gibco). PCR was performed using the For TM3 primer (5'ATCTTCATGACCTTCTTCTCA-GAC) (SEQ ID NO:17), Gibco Taq (2.5 units) and the following profile [initial denaturation at 95° for 3 min, [(denature at 94° for 1 min, anneal at 64° for 1 min, and polymerize at 72° for 3 min) for 35 cycles} with a final extension of 10 min at 72°]. nPCR was performed using the previous PCR profile with 5 µl of a 1:100 dilution from the previous PCR, and For 4(1) (5'AGGAAGTAC-CTCTGGGGCTTCA) (SEQ ID NO:18). The 3' RACE nPCR products were purified and cloned to yield zPTH1R (3')/pGEMTeasy.

Midiprep DNA of zPTH1R(5')/pGEMTeasy and zPTH1R (3')/pGEMTeasy were digested with Mfe I and Nde I (New England Biolabs, Beverly, Mass.), and a 1.0 Kb fragment from zPTH1R(3') was ligated into an approximately 4.5 Kb fragment from ZPTH1R(5 ')/pGEMTeasy to yield the full length zPTH1R clone, zPTH1R(FL)/pGEMTeasy. The zPTH1R(FL)/pGEMTeasy plasmid DNA was digested with EcoRI and SacI, and cloned into the corresponding sites in pGEM-3 (Promega) to yield zPTH1R(FL)/pGEM3. Subsequently, an EcoRI/SphI fragment, from the insert of zPTH1R(FL)/pGEM3 which comprises the entire coding region, of the zPTH1R was cloned into the corresponding sites of pcDNAI/Amp (Invitrogen) to yield zPTH1R(FL)/ pcDNAI/Amp (zPTH1R).

The 5' RACE reactions generated two PCR products which contained an identical Kozak sequence and coding region (including the putative signal sequence) but varied in the length of the 5' UT; 5'RACE#29 was 149 bp and 5'RACE#25 was 391 bp. Both clones, zPTH1R#25 and zPTH1R#29, were characterized by radioligand assay, total IP generation, and cAMP accumulation.

The amino acid sequence encoded by zPTH1R cDNA (536 residues, FIG. 2A) showed highest sequence homology to the frog and mammalian PTH1Rs (Bergwitz, et al., (1998); Kong, et al., (1994)). The overall amino acid sequence homology with the hPTH1R was 76% but only 68% when compared to the hPTH2R. Similar to the mammalian PTH1Rs, the 3' non-coding region of zPTH1R did not contain a typical polyadenylation signal sequence, however, an imperfect sequence was found (TATAAA) 49 bp upstream of the poly $A_{(n)}$ tail.

Example 4

Isolation of Full-Length cDNAs Encoding the zPTH3R

The genomic clone, zPTH3R(TM6/7), contained, at the 5' and 3' end, nucleotide sequences which were similar to but distinct from zPTH1R and zPTH2R, and contained approximately 700 bp, rather than 84 bp, of intronic sequence. This information indicated that portions of a novel gene had been isolated, subsequently refered to as zPTH3R. RT-PCR using For313 and primers specific for zPTH3R(TM6/7) produced a 450 bp cDNA clone, zPTH3R(TM3/6), which encodes TM3 through TM6 of the zPTH3R.

A zebrafish 1 gt1 1 cDNA library (Clontech) was screened by plaque hybridization using a 450 bp $^{32}$P-radiolabeled cDNA probe which was generated by PCR from zPTH3R (TM3/6)/pGEMT. Filters containing $1.5 \times 10^6$ pfu were hybridized (42° for 18 hrs) in 50% formamide (Rubin et al., 1999), and washes were performed for 30 min each at RT, 50°, and at 55°, respectively, with 1×SSC/0.1% SDS. Autoradiography was performed for 5 days at −70° with a DuPont Cronex intensifying screen and Kodak XAR film. A single phage was plaque-purified and subcloned into the EcoRI site of pcDNAI/Amp using the λ TRAP phage kit (Clontech) to yield zeb3-3'/pcDNAI/Amp.

5' RACE reactions (Gibco) were performed as above using three successive reverse zPTH3R primers [TM1 (5' GAAGAGGTGGATGTGGATGTAGTT) (SEQ ID NO:19), G (5' GCAGTGGAGACGTTTGAAATA) (SEQ ID NO:20), and E3 (5' CCAGTTACCTGATGCATCACAGTG) (SEQ ID NO:21)]. The cDNA products were ligated to pGEMT-EASY (yielding zeb3-5'/pGEMT), minipreped, and their sequences analysed for homology to the known PTH receptors using GCG. Inserts which were determined to contain a nucleotide sequence with homology to the signal sequence of the mammalian PTH1Rs were ligated into zeb3-3'/pcD-NAI/Amp using sites for BamHI, ApaLI, and NotI to yield zPTH3R(FL)/pcDNAI/Amp (zPTH3R).

From $1.5 \times 10^6$ screened PFUs, a single phage clone was identified and the 2.5 Kb insert was subcloned to yield zeb3-3'/pcDNAI/Amp. Sequence analysis showed that the clone was closely related to the known PTH1Rs from the region corresponding to the mammalian exon E1 through the carboxy-terminal region encoded by exon T (Kong, et al., (1994)). However, the cDNA portion encoding the amino-terminal, extracellular domain and most of the 3' untranslated region immediately following the termination codon were missing. 5'RACE on total zebrafish RNA revealed the presence of several putative splice variants which is similar to the findings with the zPTH2R (Rubin et al., (1999)). Seven of the ten zeb3-5' clones were identified as containing cDNA sequences similar to the mammalian exons E3 and E1, which encode portions of the amino-terminal extracellular domain of the PTH1Rs. These clones also contained a Kozak sequence and a nucleotide sequence with homology to the signal peptide sequence found in the mammalian PTH1Rs (Kong, et al., (1994); Schipani, et al., (1995)). Three other zeb3-5' clones, which also contained the E3 and E1 equivalent, had different 5' ends and could therefore represent putative splice variants. Similar to the zPTH2R (Rubin et al., (1999)) and the human PTH1R (Joun et al. (1997), Bettoun et al., (1997)), one of these zPTH3R putative splice variants lacked a signal peptide sequence but did contain an initiator AUG two codons upstream of the exon E1 equivalent. The second putative splice variant lacked a Kozak sequence, an initiator AUG, and contained a highly charged sequence upstream of the equivalent of E1 which is unlikely to represent a signal peptide. Only those clones which contained a Kozak sequence, an inframe AUG, and a 5' coding region with homology to the zPTH1R, were ligated into the ApaLI site of zeb3-3'/pcDNAI/Amp to yield the full-length zPTH3R (FIG. 1).

Overall, the sequence encoded by this novel receptor (542 residues, FIG. 2B) shared 66% AA similarity and 59% AA identity with zPTH1R, but only 55% similarity with the zPTH2R. Similar to the frog PTH1Rs, zPTH1R and zPTH3R lacked the equivalent of the cDNA encoded by exon E2, suggesting that the appearance of this non-essential exon represents a mammalian evolutionary innovation (Lee, et al., (1994)).

In contrast to this mammalian E2 apomorphy, zPTH1R and zPTH3R contain the same eight extracellular cysteines as all known mammalian and non-mammalian members of this family of G protein-coupled receptors as well as several other "signature residues". However, there are differences in the number of consensus sequences (N-X-S or N-X-T) for potential N-glycosylation between zPTH1R and zPTH3R; only two are conserved for all zebrafish PTH receptors (FIG. 2C). Furthermore, analysis of the intracellular tail residues indicates that this region has a higher rate of sequence variation between PTH receptor subtypes and was therefore used for further comparison (Table 2). For example, the homology between zPTH1R and hPTHlR in this region is 56%, which is similar to the 58% AA similarity for zPTH2R and hPTH2R. In contrast, the homology between the tail regions of zPTH3R and hiPTH1R is 38%, and 28% when compared to hPTH2R (Table 2). The zPTH3R was therefore identified as a novel member within the PTH/PTHrP receptor family.

Example 5

Functional characterization of zPTH1R and zPTH3R in COS-7 cells

Plasmid DNAs encoding the two full length ZPTH1Rs (#25 and #29) and the zPTH3R were transiently expressed in COS-7 cells. COS-7 African green monkey kidney cells (approximately 200,000 cells/well in a 24-well plate) were cultured and transfected with plasmid DNA (200 ng/well) as described (Rubin et al., (1998)). After transfection, cells were cultured for 72 hrs at 37° with daily exchanges of medium, followed by an additional 24 hrs at 33° (Gardella et al., (1997)) until they were functionally evaluated after 96 hrs.

Radioligand studies with COS-7 cells expressing either zPTH1R or zPTH3R were performed as described using either $^{125}$I-labeled [Nle$^{8,21}$,Tyr$^{34}$]rPTH-(1–34)amide (rPTH) (SEQ ID NO:22) or $^{125}$I-labeled [Tyr$^{36}$]hPTHrP-(1–36)amide (PTHrP) (SEQ ID NO:23), and increasing concentrations of either [Tyr$^{34}$]hPTH(1–34)amide (PTH) (SEQ ID NO:24), or [Tyr36]hPTHrP(1–36)amide (PTHrP) (SEQ ID NO:25) (Bergwitz et al., (1997)). Peptides were synthesized by the MGH polymer core facility as described (Gardella et al., (1996)). Specific binding was calculated by subtracting radioligand binding in the presence of excess unlabeled peptide from the total binding. All points represent mean±S.E.M. of two to three replicates from two or more independent experiments. IC$_{50}$ values (dose of a competing ligand which resulted in 50% inhibition of radioligand binding) were calculated as previously described (Gardella et al., (1996)).

In order to assess agonist-dependent cAMP accumulation of COS-7 cells expressing zPTH1R and zPTH3R, experiments were done in 24-well plates with COS-7 cells stimulated in the presence of increasing concentrations of either PTH or PTHrP, and intracellular cAMP was determined as described (Bergiwtz et al.,(1998)). EC$_{50}$ values were determined as previously described (Gardella et al., (1996)).

In order to determine total inositol phosphate turnover for COS-7 cells expressing zPTH1R, zPTH3R, and hPTH1R, cells were grown in 6-well plates with COS-7 cells (approximately 200,00 cells/well transfected with either 1 μg/well of zPTH1R, zPTH3R, or hPTH 1R (stina)). Cells were cultured for 3 days inDMEM/7% fetal bovine serum (FBS) at 37° C. with daily exchanges of medium. The cells were then preloaded with 3 μCi/ml myo-[$^3$H]inositol (New England Nuclear, Boston, Mass.) in inositol-free DMEM (Gibco)/7% FBS (33° C. for 18 hr). The following day, plates were rinsed and then incubated with 10$^{-6}$ M of either PTH, PTHrP in DMEM/0.1% BSA, or with DMEM/0.1% BSA alone (40 min at 37° C.), in the presence of 30 mM LiCl. Total inositol phosphate (IPs) were isolated by anion exchange column chromatography as previously described (Iida-Klein et al., (1994 and 1995)), and 1 ml of the eluate (⅛th of total) was counted in a liquid scintillation counter (model LS 60001C, Beckman, Fullerton, Calif.). All points represent mean±S.E.M. of two to three replicates from two or more independent experiments.

Both zPTH1R clones showed high affinity binding of radiolabeled rPTH and PTHrP (Table 2, FIG. 4). Apparently, due to the shorter 5' UT, zPTH1R#29 showed in comparison to #25 slightly higher expression levels and higher maximal cAMP accumulation (101.6 pmole/well for hPT1rP and 106.2 pmole/well for hPTH versus 92.4 pmole/well for hPTHrP and 90.4 pmole/well for hPTH; see Table 2), but otherwise both clones were indistinguishable. Only the functional data for zPTH1R#29 are therefore presented (FIG. 3, Table 3). Interestingly, zPTH3R showed a higher specific binding for radiolabeled PTHrP than rPTH. Furthermore, the zPTH3R showed a higher apparent Kd for PTHrP than PTH (approximately 3 nM versus approximately 100 nM, respectively). These results indicate that zPTH3R preferentially interacts with PTHrP.

Similar to these binding data, COS-7 cells expressing the zPTH1R showed very similar EC$_{50s}$ for cAMP accumulation in response to either PTH or PTHrP which is similar to the findings with mammalian PTH1Rs (EC$_{50}$: 0.8±0.03 nM for PTH and 0.3±0.04 nM for PTHrP, Table 2). The zPTH3R showed a higher maximal cAMP accumulation (285.4 nM for PTH and 227.4 for PTHrP nM), but in contrast to the zPTH1R, zPTH3R showed a reduced efficacy for PTH (EC$_{50s}$: 5.98±0.24 nM for PTH and 0.49±0.17 nM for PTHrP, Table 2, FIG. 4). Furthermore, in addition to being more efficiently activated by PTHrP, the zPTH3R showed a significant activation at $10^{-11}$ M (FIG. 4). These results confirmed the radioreceptor studies which had indicated that the zPTH3R interacts preferentially with PTHrP.

Similar to the mammalian PTH1Rs, COS-7 cells expressing the zPTH1R showed an equivalent increase of IP accumulation (2-fold) when stimulated with either PTH or PTHrP. In contrast, despite higher expression levels, no IP accumulation was detectable when challenged with either ligand (FIG. 5). The lack of signaling through this second messenger may be related to significant structural alterations in the second intracellular loop of zPTH3R (FIG. 4). Previous studies with the rat PTH1R have shown that this portion of the receptor is important for IP signaling, since replacement of some residues in this "EKKY" cassette either impaired or abolished phospholipase C activation. While the ZPTH1R contains a conserved DRKY sequence instead of the mammalian EKKY, the corresponding AA residues of the zPTH3R are DKNC (FIG. 3). The two most important residues are therefore altered in the novel receptor which could explain the signaling selectivity of the zPTH3R. The zPTH3R is therefore a naturally occurring PTH/PTHrP receptor which appears to be incapable of signaling through IP.

Example 6

Southern Blot Analysis of Zebrafish Genomic DNA

To confirm that zPTH1R and zPTH3 Rare encoded by distinct genes, three infrequently cutting restriction endonucleases were utilized to digest zebrafish genomic DNA to completion (data not shown). Approximately 16 µg of zebrafish genomic DNA was digested to completion with either BamHI, EcoRI, or HindIII, split into two equal aliquots for electrophoresis through a 0.8% agarose gel containing ethidium bromide, and transferred onto a nitrocellulose membrane (MSI, Westborough, Mass.). After baking in vacuo for 2 hr at 80° C., the blots were hybridized in 50% formamide (42° for 18 hrs) with PCR-generated $^{32}$p-labeled probes (Schowalter and Sommer, 1989) encoding either the carboxy-terminal tail of zPTH1R or zPTH3R (240 and 335 bp, respectively). Washes were performed for 30 min each at RT and 42° in 1×SSC/0.1% SDS, and at 50° in 0.5×SSC/0.1% SDS followed by autoradiography at −70° for 7 days with a DuPont Cronex intensifying screen and Kodak XAR film.

Initial Southern blot data using probes corresponding to TM3 through TM6 of either receptor showed multiple hybridizing DNA species, indicating that these probes cross hybridized with each others gene or with closely related genes (data not shown). To increase the specificity for either subtype, hybridizations were performed with radiolabeled probes comprising only the tail region of each receptor, zPTH1R/tail or zPTH3R/tail, which showed the highest rates of sequence variation between PTH receptor subtypes. For each digest the tail probes hybridized, under stringent conditions, to a single but different genomic DNA fragment indicating that distinct genes encode zPTH1R and zPTH3R (data not shown).

Example 7

Phylogenetic and Structural Analyses of All Known PTHRs

Alignment of all known PTH1Rs, PTH2Rs, the goldfish VIP receptor (#U56391), and the human CRF receptor (#P34998) sequences was performed as previously described (Rubin et al., (1999)). Sequences were subsequently aligned within MacClade 3.0 (Maddison and Maddison, 1992) and gaps were entered to maximize the homology of the native proteins. Each AA was treated as an unweighted character when analyzed using the branch-and-bound search option of PAUP 3.1 (Swofford, 1993). A bootstrapping analysis using the branch-and-bound option on 100 replicates (Hedges, (1992)) was performed and only groups which were compatible with the 50% majority-rule consensus were retained (Swofford and Olsen, (1990); Swofford, (1993)).

GCG was used for comparing the tail regions of zPTH1R, zPTH2R, zPTH3R, hPTH1R, and hPTH2R. A further analysis was performed within MacClade to determine unambiguous residues which may be character-dependent for each PTH/PTHrP receptor subtype (Madison and Maddison, 1992; Swofford, 1993; Rubin et al., 1999).

The single most parsimonious Bootstrap consensus tree revealed two statistically significant PTH/PTHrP receptor clades; the PTH1R/PTH3R clade and the PTH2R clade (FIG. 7). Furthermore, within the PTH1R/PTH3R lade, the PTH1R groups significantly different from PTH3R and, at least for the PTH1R, the terminal branches contained within are congruent with morphologically based phylogenies (Pough, et al., (1989)).

Whereas the overall amino acid conservation between zPTH1R and zPTH3R is relatively high, particularly within the transmembrane region, multivariate analysis led to the identification of amino acid residues that may be specific for PTH3Rs (FIG. 3). Although additional PTH3R sequences from other species are required to confirm the receptor specificity of these residues, the limited number of amino acid changes may already allow mutational studies to explore their functional importance, particularly with regard to phospholipase C activation.

Example 7

Southern Blot Analysis of Mouse Genomic DNA

In order to establish the occurrence of PTH3R in mammals, Southern blot analysis was done with genomic DNA from a wild-type mouse (FIG. 7, left lane, 10 µg) and from a mouse lacking both copies of the PTH/PTHrP receptor gene (FIG. 7, right lane 2 µg).

Briefly, genomic DNAs were digested to completion with the restriction enzyme BamHI, subjected to agarose gel electrophoresis and transferred to a membrane for probing with radiolabeled PTH3R DNA (approximately 300 bp encoding the tail portion of the zPTH3R). Hybridization was performed under conditions of 30% formamide at 42 degrees Celsius overnight. The blot was subjected to a final wash of 1×SSC at 60 degrees Celsius. Radiography was performed by exposing the blot to film for 3 days at −80 C with an intensifying screen. The detection of a band in the PTH/PTHrP receptor knockout (KO) DNA indicates the presence of PTH3R in mouse genomic DNA.

Table 2. Comparisons of the Amino Acid sequences of the Intracellular, Carboxy-Terminal Tail of Different PTH Receptors Residues comprising the tail region of the zPTH1R and zPTH3R were compared to corresponding regions of the zPTH2R, and the human PTH1R or PTH2R. Percent similarity and percent identity are indicated.

TABLE 2

|        | zPTH1R | zPTH2R | zPTH3R | hPTH1R |
|--------|--------|--------|--------|--------|
| zPTH2R | 38/31  |        |        |        |
| zPTH3R | 36/33  | 26/23  |        |        |
| hPTH1R | 56/50  | 35/28  | 38/33  |        |
| hPTH2R | 38/29  | 58/53  | 28/25  | 38/31  |

Table 3. Binding and cAMP Signaling Properties of PTH and PTHrP Analogs on the zPTH1R and the zPTH3R Competitive binding and cAMP stimulation assays were performed at room temperature with intact COS-7 cells that expressed either the zPTH1R or the zPTH3R, as described in Materials and Methods. Homologous binding reactions utilized $^{125}$I-rPTH with unlabeled rPTH, and $^{125}$I-hPTHrP with unlabeled hPTHrP, heterologous binding reactions utilized $^{125}$I-hPTH with unlabeled rPTH. $EC_{50}$ and $IC_{50}$ values were determined as previously described (Gardella et al., 1996). Values are the mean±SEM of at least three independent transfections. ND, not determined.

TABLE 3

| | zPPR3 | | | zPPR1#29 | | | zPPR1#25 | | |
|---|---|---|---|---|---|---|---|---|---|
| Ligand | Binding $IC_{50}$ (nM) | cAMP $EC_{50}$ (nM) | cAMP Maximum (pmol/well) | Binding $IC_{50}$ (nM) | cAMP $EC_{50}$ (nM) | cAMP Maximum (pmol/well) | Binding $IC_{50}$ (nM) | cAMP $EC_{50}$ (nM) | cAMP Maximum (pmol/well) |
| hPTHrP | ~3.0 | 0.49 ± 0.17 | 285.4 ± 3.4 | ~3.0 | 0.3 ± 0.04 | 101.6 ± 3.6 | ~3.0 | 0.90 ± 0.09 | 92.4 ± 8.00 |
| hPTH | ~100 | 5.98 ± 0.24 | 227.4 ± 41.6 | ~3.0 | 0.8 ± 0.03 | 106.2 ± 4.8 | ~3.0 | ~3.0 | 90.4 ± 11.4 |

LIST OF OTHER REFERENCES CITED HEREIN:

1. Potts, J. T., Jr., Jüppner, H.: Parathyroid hormone and parathyroid hormone-related peptide in calcium homeostasis, bone metabolism, and bone development: the proteins, their genes, and receptors. In: Avioli L V, Krane S M, eds. Metabolic Bone Disease, 3 ed. New York: Academic Press, 1997; 51–94.
2. Bergwitz, C., Klein, P., Kohno, H., Forman, S. A., Lee, K., Rubin, D., Jüppner, H. (1998). Identification, functional characterization, and developmental expression of two nonallelic parathyroid hormone (PTH)/PTH-related peptide (PTHrP) receptor isoforms in Xenopus laevis (Daudin). Endocrinology 139, 723–732
3. Broadus, A. E., Stewart, A. F.: Parathyroid hormone-related protein: Structure, processing, and physiological actions. In: Bilezikian J P, Levine M A, Marcus R, eds. The parathyroids. Basic and Clinical Concepts. New York: Raven Press, 1994; 259–294.
4. Karaplis, A. C., Luz, A., Glowacki, J., Bronson, R., Tybulewicz, V., Kronenberg, H. M., Mulligan, R. C. (1994). Lethal skeletal dysplasia from targeted disruption of the parathyroid hormone-related peptide gene. Genes Develop 8, 277–289.
5. Lanske, B., Karaplis, A. C., Luz, A., Vortkamp, A., Pirro, A., Karperien, M., Defize, L. H. K., Ho, C., Mulligan, R. C., Abou-Samra, A. B., Jüppner, H., Segre, G. V., Kronenberg, H. M. (1996). PTH/PTHrP receptor in early development and Indian hedgehog-regulated bone growth. Science 273, 663–666.
6. Wysolmerski, J. J., Broadus, A. E., Zhou, J., Fuchs, E., Milstone, L. M., Philbrick, W. M. (1994). Overexpression of parathyroid hormone-related protein in the skin of transgenic mice interferes with hair follicle development. Proc. Natl. Acad. Sci. USA 91, 1133–1137.
7. Wysolmerski, J. J., McCaughern-Carucci, J. F., Daifotis, A. G., Broadus, A. E., Philbrick, W. M. (1996). Overexpression of parathyroid hormone-related protein or parathyroid hormone in transgenic mice impairs branching morphogenesis during mammary gland development. Development 121, 3539–3547.
8. Weir, E. C., Philbrick, W. M., Amling, M., Neff, L. A., Baron, R., Broadus, A. E. (1996). Targeted overexpression of parathyroid hormone-related peptide in chondrocytes causes skeletal dysplasia and delayed endochondral bone formation. Proc. Natl. Acad. Sci. USA 93, 10240–10245.
9. Philbrick, W. M., Dreyer, B. E., Nakchbandi, I. A., Karaplis, A. C. (1998). Parathyroid hormone-related protein is required for tooth eruption. Proc. Natl. Acad. Sci. USA 95, 11846–11851.
10. Usdin, T. B., Gruber, C., Bonner, T. I. (1995). Identification and functional expression of a receptor selectively recognizing parathyroid hormone, the PTH2 receptor. J. Biol. Chem. 270, 15455–15458.
11. Usdin, T. B., Bonner, T. I., Harta, G., Mezey, E. (1996). Distribution of PTH-2 receptor messenger RNA in rat. Endocrinology 137, 4285–4297.
12. Rubin, D. A., Hellman, P., Zon, L. I., Lobb, C. J., Bergwitz, C., Jüppner, H. (1999). A teleost parathyroid hormone type-2 receptor is activated by PTH and not PTHrP: implications for the evolutionary conservation of calcium-regulating peptide hormones. J. Bio. Chem. 271, 23035–23042.
13. Usdin, T. B. (1997). Evidence for a parathyroid hormone-2 receptor selective ligand in the hypothalamus. Endocrinology 138, 831–834.
14. Orloff, J. J., Ganz, M. B., Ribaudo, A. E., Burtis, W. J., Reiss, M., Milstone, L. M., Stewart, A. F. (1992). Analysis of PTHrP binding and signal transduction mechanisms in benign and malignant squamous cells. Am J Physiol 262, E599–607.
15. Gaich, G., Orloff, J. J., Atillasoy, E. J., Burtis, W. J., Ganz, M. B., Stewart, A. F. (1993). Amino-terminal parathyroid hormone-related portein: specific binding and cytosolic calcium responses in rat insulinoma cells. Endocrinology 132, 1402–1409.
16. Orloff, J. J., Kats, Y., Urena, P., Schipani, E., Vasavada, R. C., Philbrick, W. M., Behal, A., Abou-Samra, A. B., Segre, G. V., Jüppner, H. (1995). Further evidence for a novel receptor for amino-terminal parathyroid hormone-related protein on keratinocytes and squamous carcinoma cell lines. Endocrinology 136, 3016–3023.

17. Fukayama, S., Tashjian, A. H., Davis, J. N. (1995). Signaling by N- and C-terminal sequences of parathyroid hormone-related protein in hippocampal neurons. Proc. Natl. Acad. Sci. USA 92, 10182–10886.
18. Yamamoto, S., Morimoto, I., Yanagihara, N., Zeki, K., Fujihira, T., Izumi, F., Yamashita, H., Eto, S. (1997). Parathyroid hormone-related peptide-(1–34) [PTHrP-(1–34)] induces vasopressin release from the rat supraoptic nucleus in vitro through a novel receptor distinct from a type I or type II PTH/PTHrP receptor. Endocrinology 138, 2066–2072.
19. Yamamoto, S., Morimoto, I., Zeki, K., Ueta, Y., Yamashita, H., Kannan, H., Eto, S. (1998). Centrally administered parathyroid hormone (PTH)-related protein (1–34) but not PTH(1–34) stimulates arginine-vasopressin secretion and its messenger ribonucleoic acid expression in supraoptic nucleus of the conscious rats. Endocrinology 139, 383–388.
20. Kovacs, C. S., Lanske, B., Hunzelman, J. L., Guo, J., Karaplis, A. C., Kronenberg, H. M. (1996). Parathyroid hormone-related peptide (PTHrP) regulates fetal placental calcium transport through a receptor distinct from the PTH/PTHrP receptor. Proc. Natl. Acad. Sci. USA 93, 15233–15238.
21. Wu, T. L., Vasavada, R. C., Yang, K., Massfelder, T., Ganz, M., Abbas, S. K., Care, A. D., Stewart, A. F. (1996). Structural and physiological characterization of the mid-region secretory species of parathyroid hormone-related protein. J. Biol. Chem. 271, 24371–24381.
22. Orloff, J. J., Ganz, M. B., Nathanson, H., Moyer, M. S., Kats, Y., Mitnick, M., Behal, A., Gasalla-Herraiz, J., Isales, C. M. (1996). A midregion parathyroid hormone-related peptide mobilizes cytosolic calcium and stimulates formation of inositol trisphosphate in a squamous carcinoma cell line. Endocrinology 137, 5376–5385.
23. Inomata, N., Akiyama, M., Kubota, N., Jüppner, H. (1995). Characterization of a novel PTH-receptor with specificity for the carboxyl-terminal region of PTH (1–84). Endocrinology 136, 4732–4740.
24. Takasu, H., Baba, H., Inomata, N., Uchiyama, Y., Kubota, N., Kumaki, K., Matsumoto, A., Nakajima, K., Kimura, T., Sakakibara, S., Fujita, T., Chihara, K., Nagai, I. (1996). The 69–84 amino acid region of the parathyroid hormone molecule is essential for the interaction of the hormone with the binding sites with carboxyl-terminal specificity. Endocrinology 137, 5537–5543.
25. Gardella, T. J., Luck, M. D., Jensen, G. S., Usdin, T. B., Jüppner, H. (1996). Converting parathyroid hormone-related peptide (PTHrP) into a potent PTH-2 receptor agonist. J. Biol. Chem. 271, 19888–19893.
26. Bergwitz, C., Jusseaume, S. A., Luck, M. D., Jüppner, H., Gardella, T. J. (1997). Residues in the membrane-spanning and extracellular regions of the parathyroid hormone (PTH)-2 receptor determine signaling selectivity for PTH and PTH-related peptide. J. Biol. Chem. 272, 28861–28868.
27. Schipani, E., Karga, H., Karaplis, A. C., Potts, J. T., Jr., Kronenberg, H. M., Segre, G. V., Abou-Samra, A. B., Jüppner, H. (1993). Identical complementary deoxyribonucleic acids encode a human renal and bone parathyroid hormone (PTH)/PTH-related peptide receptor. Endocrinology 132, 2157–2165.
28. Iida-Klein, A., Guo, J., Drake, M. T., Kronenberg, H. M., Abou-Samra, A. B., Bringhurst, F. R., Segre, G. V. (1994). Structural requirements of PTH/PTHrP receptors for phospholipase C activation and regulation of phosphate uptake. J. Bone Miner. Res.
29. Iida-Klein, A., Guo, J., Xie, L. Y., Jüppner, H., Potts, J. T., Jr., Kronenberg, H. M., Bringhurst, F. R., Abou-Samra, A. B., Segre, G. V. (1995). Truncation of the carboxyl-terminal region of the parathyroid hormone (PTH)/PTH-related peptide receptor enhances PTH stimulation of adenylate cyclase but not phospholipase C. J. Biol. Chem. 270, 8458–8465.
30. Kong, X. F., Schipani, E., Lanske, B., Joun, H., Karperien, M., Defize, L. H. K., Jüppner, H., Potts, J. T., Segre, G. V., Kronenberg, H. M., Abou-Samra, A. B. (1994). The rat, mouse and human genes encoding the receptor for parathyroid hormone and parathyroid hormone-related peptide are highly homologous. Biochem. Biophys. Res. Comm. 200, 1290–1299.
31. Schipani, E., Weinstein, L. S., Bergwitz, C., Iida-Klein, A., Kong, X. F., Stuhrmann, M., Kruse, K., Whyte, M. P., Murray, T., Schmidtke, J., van Dop, C., Brickman, A. S., Crawford, J. D., Potts, J. T., Jr., Kronenberg, H. M., Abou-Samra, A. B., Segre, G. V., Jüppner, H. (1995). Pseudohypoparathyroidism type Ib is not caused by mutations in the coding exons of the human parathyroid hormone (PTH)/PTH-related peptide receptor gene. J. Clin. Endocrinol. Metab. 80, 1611–1621.
32. Joun, H., Lanske, B., Karperien, M., Qian, F., Defize, L., Abou-Samra, A. (1997). Tissue-specific transcription start sites and alternative splicing of the parathyroid hormone (PTH)/PTH-related peptide (PTHrP) receptor gene: a new PTH/PTHrP receptor splice variant that lacks the signal peptide. Endocrinology 138, 1742–1749.
33. Bettoun, J. D., Minagawa, M., Kwan, M. Y., Lee, H. S., Yasuda, T., Hendy, G. N., Goltzman, D., White, J. H. (1997). Cloning and characterization of the promoter regions of the human parathyroid hormone (PTH)/PTH-related peptide receptor gene: analysis of deoxyribonucleic acid from normal subjects and patients with pseudohypoparathyroidism type Ib. J. Clin. Endocrinol. Metab. 82, 1031–1040.
34. Bettoun, J. D., Minagawa, M., Hendy, G. N., Alpert, L. C., Goodyer, C. G., Goltzman, D., White, J. H. (1998). Developmental upregulation of the human parathyroid hormone (PTH)/PTH-related peptide receptor gene expression from conserved and human-specific promoters. J. Clin. Invest. 102, 958–967.
35. Lee, C., Gardella, T. J., Abou-Samra, A. B., Nussbaum, S. R., Segre, G. V., Potts, J. T., Jr., Kronenberg, H. M., Jüppner, H. (1994). Role of the extracellular regions of the parathyroid hormone (PTH)/PTH-related peptide receptor in hormone binding. Endocrinology 135, 1488–1495.
36. Maddison, W. P., and Maddison, M. D. (1992) McClade, 3rd Ed., Sinauer Associates, Inc., Sunderland, Mass.
37. Hedges, S. B., (1992) Mol. Cell. Evol. 9: 366–369.
38. Swofford, D. L., (1993) PAUP: Phylogenetic Analysis Using Parsimony, 3.1 ED., Illinois Natural History Survey, Champaign, Ill.
39. Swofford, D. L., and Olsen, G. J., (1990) in Molecular Systematics (Hillis, D. M., and Moritz, C., eds.) pp 411–501, Sinauer Associates, Inc., Sunderland, Mass.
40. Rubin, D. A., and Jüppner, H., (1999) Zebrafish Express the Common Parathyroid Hormone/Parathyroid Hormone-related Peptide (PTH1R) and a Novel Receptor (PTH3R) That Is Preferentially Activated by Mammalian and Fugufish Parathyroid Hormone-related Peptide. J. Bio. Chem. 274: 28185–28190.

41. Pough, F. H., Heiser, J. B., and McFarland, W. N. (1989) Vertebrate Life, 3rd Ed., Macmillan, N. Y.

42. Usdin, T. B., Hoare, S. R. J., Wang, T., Mezey, E., and Kowalak, J. A. (1999) TIP39: A New Neuropeptide and PTH2-receptor Agonist From Hypothalamus Nature Neuroscience 2: 941–943.

SEQUENCE LISTING

<160> NUMBER OF SEQ ID NOS: 25

<210> SEQ ID NO 1
<211> LENGTH: 1609
<212> TYPE: DNA
<213> ORGANISM: Danio rerio
<220> FEATURE:
<221> NAME/KEY: CDS
<222> LOCATION: (1)..(1608)

<400> SEQUENCE: 1

```
atg gga gcc acg ctg atc gta cgc act tta ggc ttt ctc ttc tgc ggc      48
Met Gly Ala Thr Leu Ile Val Arg Thr Leu Gly Phe Leu Phe Cys Gly
  1               5                  10                  15 acc ttg ctg agt ttc gtc tat ggt ctg gtc gat gca gat gat gtc ctc      96
Thr Leu Leu Ser Phe Val Tyr Gly Leu Val Asp Ala Asp Asp Val Leu
             20                  25                  30 aca aag gag gag caa atc tat ctt ctg ttc aac gca aaa cga aaa tgt     144
Thr Lys Glu Glu Gln Ile Tyr Leu Leu Phe Asn Ala Lys Arg Lys Cys
         35                  40                  45 gag cga gca atc aag tcc aag cat aaa acg tct gag gga tcc tgt ctg     192
Glu Arg Ala Ile Lys Ser Lys His Lys Thr Ser Glu Gly Ser Cys Leu
     50                  55                  60 cca gag tgg gat ggc atc cta tgt tgg ccc gag gga gtt cct gga aag     240
Pro Glu Trp Asp Gly Ile Leu Cys Trp Pro Glu Gly Val Pro Gly Lys
 65                  70                  75                  80 atg gtg tcc act tca tgc cca gag tac ata tat gac ttc aac cac aaa     288
Met Val Ser Thr Ser Cys Pro Glu Tyr Ile Tyr Asp Phe Asn His Lys
                 85                  90                  95 ggt cat gcc tac cgg cgc tgc gac ctg aac ggg acc tgg gaa ctg gcc     336
Gly His Ala Tyr Arg Arg Cys Asp Leu Asn Gly Thr Trp Glu Leu Ala
            100                 105                 110 tca cat aac aac aaa acc tgg gct aat tac agc gaa tgt gcc aaa ttc     384
Ser His Asn Asn Lys Thr Trp Ala Asn Tyr Ser Glu Cys Ala Lys Phe
        115                 120                 125 ttc ccc cat tat aac cag aac cag gag agg gag gtt ttc gac aga ctt     432
Phe Pro His Tyr Asn Gln Asn Gln Glu Arg Glu Val Phe Asp Arg Leu
    130                 135                 140 tac ctg atc tac aca gtg ggc tac tcc atc tct ctg gga tca ctt atg     480
Tyr Leu Ile Tyr Thr Val Gly Tyr Ser Ile Ser Leu Gly Ser Leu Met
145                 150                 155                 160 gtg gcc aca gtc atc ctc gga tac ttt cga cgg ctc cac tgc acc agg     528
Val Ala Thr Val Ile Leu Gly Tyr Phe Arg Arg Leu His Cys Thr Arg
                165                 170                 175 aac tac atc cac atg cac ctg ttt cta tcg ttc atg ttg agg gcc att     576
Asn Tyr Ile His Met His Leu Phe Leu Ser Phe Met Leu Arg Ala Ile
            180                 185                 190 agt atc ttc gtg aag gat gtg gtg ctg tac tct ggt tcg gcg ctg cag     624
Ser Ile Phe Val Lys Asp Val Val Leu Tyr Ser Gly Ser Ala Leu Gln
        195                 200                 205 gaa atg gaa cga atc act gtg gag gat ctc aaa tcc atc act gaa gcc     672
Glu Met Glu Arg Ile Thr Val Glu Asp Leu Lys Ser Ile Thr Glu Ala
    210                 215                 220
```

```
cct cct gcc aac aaa acc cag ttt atc ggc tgt aag gtg gcg gtg acg        720
Pro Pro Ala Asn Lys Thr Gln Phe Ile Gly Cys Lys Val Ala Val Thr
225                 230                 235                 240 ctc ttc ttg tac ttc ttg gcc act aat tat tac tgg att ctg gtg gaa        768
Leu Phe Leu Tyr Phe Leu Ala Thr Asn Tyr Tyr Trp Ile Leu Val Glu
                245                 250                 255 ggc ctg tac ctg cac agc ctt atc ttc atg acc ttc ttc tca gac agg        816
Gly Leu Tyr Leu His Ser Leu Ile Phe Met Thr Phe Phe Ser Asp Arg
            260                 265                 270 aag tac ctc tgg ggc ttc act ctg att ggt tgg ggt gtt cct gcg atg        864
Lys Tyr Leu Trp Gly Phe Thr Leu Ile Gly Trp Gly Val Pro Ala Met
        275                 280                 285 ttt gtc acc atc tgg gcg agt gtt aga gcc aca ctt gct gac act gag        912
Phe Val Thr Ile Trp Ala Ser Val Arg Ala Thr Leu Ala Asp Thr Glu
    290                 295                 300 tgc tgg gat ttg agt gca gga aac ctg aaa tgg att gtg cag atc ccc        960
Cys Trp Asp Leu Ser Ala Gly Asn Leu Lys Trp Ile Val Gln Ile Pro
305                 310                 315                 320 att ctt act gca att gtt gtc aat ttt ttg ttg ttc ctg aat ata att       1008
Ile Leu Thr Ala Ile Val Val Asn Phe Leu Leu Phe Leu Asn Ile Ile
                325                 330                 335 cga gtc ttg gca aca aaa ctt cga gaa aca aat gcg ggc aga tgt gac       1056
Arg Val Leu Ala Thr Lys Leu Arg Glu Thr Asn Ala Gly Arg Cys Asp
            340                 345                 350 acc aga caa caa tat agg aag ctg ctg aag tcg act ctg gtc ctc atg       1104
Thr Arg Gln Gln Tyr Arg Lys Leu Leu Lys Ser Thr Leu Val Leu Met
        355                 360                 365 ccg ttg ttc ggt gtt cac tac ata gtc ttc atg gcg atg cct tac aca       1152
Pro Leu Phe Gly Val His Tyr Ile Val Phe Met Ala Met Pro Tyr Thr
    370                 375                 380 gaa gtt tct gga gta ctg tgg caa atc cag atg cat tat gaa atg ctc       1200
Glu Val Ser Gly Val Leu Trp Gln Ile Gln Met His Tyr Glu Met Leu
385                 390                 395                 400 ttt aac tca gtc cag gga ttc ttt gtt gcg att ata tat tgc ttc tgc       1248
Phe Asn Ser Val Gln Gly Phe Phe Val Ala Ile Ile Tyr Cys Phe Cys
                405                 410                 415 aac gga gag gtc caa gcg gaa atc aag aag gcc tgg aac aga agg act       1296
Asn Gly Glu Val Gln Ala Glu Ile Lys Lys Ala Trp Asn Arg Arg Thr
            420                 425                 430 ctt gct ctg gac ttc aag aga aaa gcc agg agc ggc agt aac aca tac       1344
Leu Ala Leu Asp Phe Lys Arg Lys Ala Arg Ser Gly Ser Asn Thr Tyr
        435                 440                 445 agc tat gga ccc atg gtt tct cac acc agt gtt acc aat gtg acg gcg       1392
Ser Tyr Gly Pro Met Val Ser His Thr Ser Val Thr Asn Val Thr Ala
    450                 455                 460 cgg ggg ccg ctg gcc ctt cac ctc acc aac cga ctg ggg cac gtc acc       1440
Arg Gly Pro Leu Ala Leu His Leu Thr Asn Arg Leu Gly His Val Thr
465                 470                 475                 480 act aac ggc cac aga aac ctt ccg gga tac ata aaa aac ggc tcc gtt       1488
Thr Asn Gly His Arg Asn Leu Pro Gly Tyr Ile Lys Asn Gly Ser Val
                485                 490                 495 tca gaa aac tcc atc ccg tcc tcg ggt cac gag ctt cac att cag gag       1536
Ser Glu Asn Ser Ile Pro Ser Ser Gly His Glu Leu His Ile Gln Glu
            500                 505                 510 gaa gag cct tcg aag acc ttc cag atg gag aaa acc atc cag gtg gtg       1584
Glu Glu Pro Ser Lys Thr Phe Gln Met Glu Lys Thr Ile Gln Val Val
        515                 520                 525 gag gag gaa aga gaa acc gtc atg t                                     1609
Glu Glu Glu Arg Glu Thr Val Met
```

```
                530             535

<210> SEQ ID NO 2
<211> LENGTH: 536
<212> TYPE: PRT
<213> ORGANISM: Danio rerio

<400> SEQUENCE: 2

Met Gly Ala Thr Leu Ile Val Arg Thr Leu Gly Phe Leu Phe Cys Gly
 1               5                  10                  15

Thr Leu Leu Ser Phe Val Tyr Gly Leu Val Asp Ala Asp Asp Val Leu
            20                  25                  30

Thr Lys Glu Glu Gln Ile Tyr Leu Leu Phe Asn Ala Lys Arg Lys Cys
        35                  40                  45

Glu Arg Ala Ile Lys Ser His Lys Thr Ser Glu Gly Ser Cys Leu
    50                  55                  60

Pro Glu Trp Asp Gly Ile Leu Cys Trp Pro Glu Gly Val Pro Gly Lys
65                  70                  75                  80

Met Val Ser Thr Ser Cys Pro Glu Tyr Ile Tyr Asp Phe Asn His Lys
                85                  90                  95

Gly His Ala Tyr Arg Arg Cys Asp Leu Asn Gly Thr Trp Glu Leu Ala
            100                 105                 110

Ser His Asn Asn Lys Thr Trp Ala Asn Tyr Ser Glu Cys Ala Lys Phe
        115                 120                 125

Phe Pro His Tyr Asn Gln Asn Gln Glu Arg Glu Val Phe Asp Arg Leu
    130                 135                 140

Tyr Leu Ile Tyr Thr Val Gly Tyr Ser Ile Ser Leu Gly Ser Leu Met
145                 150                 155                 160

Val Ala Thr Val Ile Leu Gly Tyr Phe Arg Arg Leu His Cys Thr Arg
                165                 170                 175

Asn Tyr Ile His Met His Leu Phe Leu Ser Phe Met Leu Arg Ala Ile
            180                 185                 190

Ser Ile Phe Val Lys Asp Val Val Leu Tyr Ser Gly Ser Ala Leu Gln
        195                 200                 205

Glu Met Glu Arg Ile Thr Val Glu Asp Leu Lys Ser Ile Thr Glu Ala
    210                 215                 220

Pro Pro Ala Asn Lys Thr Gln Phe Ile Gly Cys Lys Val Ala Val Thr
225                 230                 235                 240

Leu Phe Leu Tyr Phe Leu Ala Thr Asn Tyr Tyr Trp Ile Leu Val Glu
                245                 250                 255

Gly Leu Tyr Leu His Ser Leu Ile Phe Met Thr Phe Ser Asp Arg
            260                 265                 270

Lys Tyr Leu Trp Gly Phe Thr Leu Ile Gly Trp Gly Val Pro Ala Met
        275                 280                 285

Phe Val Thr Ile Trp Ala Ser Val Arg Ala Thr Leu Ala Asp Thr Glu
    290                 295                 300

Cys Trp Asp Leu Ser Ala Gly Asn Leu Lys Trp Ile Val Gln Ile Pro
305                 310                 315                 320

Ile Leu Thr Ala Ile Val Asn Phe Leu Leu Phe Leu Asn Ile Ile
                325                 330                 335

Arg Val Leu Ala Thr Lys Leu Arg Glu Thr Asn Ala Gly Arg Cys Asp
            340                 345                 350

Thr Arg Gln Gln Tyr Arg Lys Leu Leu Lys Ser Thr Leu Val Leu Met
        355                 360                 365
```

-continued

```
Pro Leu Phe Gly Val His Tyr Ile Val Phe Met Ala Met Pro Tyr Thr
    370                 375                 380

Glu Val Ser Gly Val Leu Trp Gln Ile Gln Met His Tyr Glu Met Leu
385                 390                 395                 400

Phe Asn Ser Val Gln Gly Phe Val Ala Ile Ile Tyr Cys Phe Cys
                405                 410                 415

Asn Gly Glu Val Gln Ala Glu Ile Lys Lys Ala Trp Asn Arg Arg Thr
            420                 425                 430

Leu Ala Leu Asp Phe Lys Arg Lys Ala Arg Ser Gly Ser Asn Thr Tyr
        435                 440                 445

Ser Tyr Gly Pro Met Val Ser His Thr Ser Val Thr Asn Val Thr Ala
    450                 455                 460

Arg Gly Pro Leu Ala Leu His Leu Thr Asn Arg Leu Gly His Val Thr
465                 470                 475                 480

Thr Asn Gly His Arg Asn Leu Pro Gly Tyr Ile Lys Asn Gly Ser Val
                485                 490                 495

Ser Glu Asn Ser Ile Pro Ser Ser Gly His Glu Leu His Ile Gln Glu
            500                 505                 510

Glu Glu Pro Ser Lys Thr Phe Gln Met Glu Lys Thr Ile Gln Val Val
        515                 520                 525

Glu Glu Glu Arg Glu Thr Val Met
    530                 535
```

<210> SEQ ID NO 3
<211> LENGTH: 2152
<212> TYPE: DNA
<213> ORGANISM: Danio rerio
<220> FEATURE:
<221> NAME/KEY: CDS
<222> LOCATION: (394)..(2019)
<220> FEATURE:
<221> NAME/KEY: misc_feature
<222> LOCATION: (2125)..(2125)
<223> OTHER INFORMATION: n is any nucleotide of a,t,g or c

<400> SEQUENCE: 3

```
ttacaccata actcacagga gatcacatct ctggacacat ctccaacaag tctctcttta      60
aaacatctac aattggactg acaaatctct tctttaatca aggatctgag ttaatacaaa     120
aaaaaatctg atgaatggaa gaaaatcatc tgtgatggta ttccagaagt taaaatctca     180
acaaaaacaa acaacgggtc ggacttcaac agatgtgtgt ccgcttgaca cggcagcatc     240
agaaagaaac aacatcttta acacaatgaa gaagtaatgg ctgcaaacgt ctgcgcttct     300
ctccacatcg acgcgactgc catgtcctga agagaaacag gagctctctg gagagcagga     360
gttctggaaa aggtcaaagg tcctgggtta agc atg gtg tca gtg gag gtc tct      414
                                   Met Val Ser Val Glu Val Ser
                                     1               5 gtg gct tta gtg ctg tgc tgt gtt tgt atg gga gcc aga gct ctg att        462
Val Ala Leu Val Leu Cys Cys Val Cys Met Gly Ala Arg Ala Leu Ile
        10                  15                  20 gat tca gat gat gtc atc aca aga gat gaa cag atc ttt ctc ctc att        510
Asp Ser Asp Asp Val Ile Thr Arg Asp Glu Gln Ile Phe Leu Leu Ile
    25                  30                  35 ggt gcg cgg tcg agg tgt gag aga acc atc cgt gca cag tca gac gtg        558
Gly Ala Arg Ser Arg Cys Glu Arg Thr Ile Arg Ala Gln Ser Asp Val
40                  45                  50                  55 gtc aga gag aat aac tgc gct cct gag tgg gat ggg atc att tgc tgg        606
Val Arg Glu Asn Asn Cys Ala Pro Glu Trp Asp Gly Ile Ile Cys Trp
                60                  65                  70
```

-continued

| | | |
|---|---|---|
| ccc aca gga aaa ccc aat cag atg gtg gca gtt ctg tgt cct gag tac<br>Pro Thr Gly Lys Pro Asn Gln Met Val Ala Val Leu Cys Pro Glu Tyr<br>75                        80                  85 | 654 |
| atc tat gac ttc aac cac aga gga tac gcg tat cga cac tgt gat gca<br>Ile Tyr Asp Phe Asn His Arg Gly Tyr Ala Tyr Arg His Cys Asp Ala<br>90                        95                  100 | 702 |
| tca ggt aac tgg gag cag gtg tcc att ata aac cgg acg tgg gca aac<br>Ser Gly Asn Trp Glu Gln Val Ser Ile Ile Asn Arg Thr Trp Ala Asn<br>105                      110                115 | 750 |
| tac acg gaa tgc acc act tac ctg cac acc aac cac agt gat cag gag<br>Tyr Thr Glu Cys Thr Thr Tyr Leu His Thr Asn His Ser Asp Gln Glu<br>120                      125                130                135 | 798 |
| gaa gtg ttt gag cgc ctt tac ctc atg tac act att gga tac tcc ata<br>Glu Val Phe Glu Arg Leu Tyr Leu Met Tyr Thr Ile Gly Tyr Ser Ile<br>                140                145                150 | 846 |
| tca ctg gca gcg tta ctg gtg gcg gtc tct atc ctt tgc tat ttc aaa<br>Ser Leu Ala Ala Leu Leu Val Ala Val Ser Ile Leu Cys Tyr Phe Lys<br>                155                160                165 | 894 |
| cgt ctc cac tgc act cgt aac tac atc cac atc cac ctc ttc acc tcg<br>Arg Leu His Cys Thr Arg Asn Tyr Ile His Ile His Leu Phe Thr Ser<br>170                      175                180 | 942 |
| ttc ata tgt cga gca atc agt att ttt gtg aaa gac gcc gtt ctt tac<br>Phe Ile Cys Arg Ala Ile Ser Ile Phe Val Lys Asp Ala Val Leu Tyr<br>185                      190                195 | 990 |
| gcc gtc acg aat gat gga gaa cta gaa gat ggg gca gtg gaa caa aga<br>Ala Val Thr Asn Asp Gly Glu Leu Glu Asp Gly Ala Val Glu Gln Arg<br>200                      205                210                215 | 1038 |
| ccc atg gtg ggc tgc aag gct gct gtg acc ctc ttc ctg tat ctg ttg<br>Pro Met Val Gly Cys Lys Ala Ala Val Thr Leu Phe Leu Tyr Leu Leu<br>                220                225                230 | 1086 |
| gcg acc aat cat tat tgg atc ctg gtg gag ggt ttg tac ttg cat agt<br>Ala Thr Asn His Tyr Trp Ile Leu Val Glu Gly Leu Tyr Leu His Ser<br>                235                240                245 | 1134 |
| ctg atc ttc atg gcc ttc ctg tct gat aag aac tgc ctg tgg gct ttg<br>Leu Ile Phe Met Ala Phe Leu Ser Asp Lys Asn Cys Leu Trp Ala Leu<br>250                      255                260 | 1182 |
| aca atc ata ggc tgg ggg atc cca gca gtg ttt gtg tct ata tgg gtc<br>Thr Ile Ile Gly Trp Gly Ile Pro Ala Val Phe Val Ser Ile Trp Val<br>265                      270                275 | 1230 |
| agt gcc agg gtg tct ctg gca gac aca cag tgc tgg gat atc agt gca<br>Ser Ala Arg Val Ser Leu Ala Asp Thr Gln Cys Trp Asp Ile Ser Ala<br>280                      285                290                295 | 1278 |
| ggc aat ttg aaa tgg att tat caa gta cca atc ctg gca gcc att gtt<br>Gly Asn Leu Lys Trp Ile Tyr Gln Val Pro Ile Leu Ala Ala Ile Val<br>                300                305                310 | 1326 |
| gta aac ttc ttc ctc ttc ctc aat atc atc agg gtt ttg gcc tct aag<br>Val Asn Phe Phe Leu Phe Leu Asn Ile Ile Arg Val Leu Ala Ser Lys<br>                315                320                325 | 1374 |
| ttg tgg gaa aca aac acg gga aaa ctg gac cct aga cag cag tac agg<br>Leu Trp Glu Thr Asn Thr Gly Lys Leu Asp Pro Arg Gln Gln Tyr Arg<br>330                      335                340 | 1422 |
| aag ctg ctg aag tca aca atg gtg ctg atg cca ctg ttt gga gtt cat<br>Lys Leu Leu Lys Ser Thr Met Val Leu Met Pro Leu Phe Gly Val His<br>345                      350                355 | 1470 |
| tac atg ctg ttc atg gct ctt ccg tac act gat gtg act ggt ttg ctg<br>Tyr Met Leu Phe Met Ala Leu Pro Tyr Thr Asp Val Thr Gly Leu Leu<br>360                      365                370                375 | 1518 |
| agg cag att ctg atg cat tac gag atg ctc ttc aat tct tca cag ggt<br>Arg Gln Ile Leu Met His Tyr Glu Met Leu Phe Asn Ser Ser Gln Gly | 1566 |

```
               380                  385                  390
ttc ttt gtg gcg ttt att tac tgc ttc tgc aat ggg gag gtg cag gca    1614
Phe Phe Val Ala Phe Ile Tyr Cys Phe Cys Asn Gly Glu Val Gln Ala
            395                  400                  405 gag gtg aag aag gcc tgg ttg cga cgc agt ctt gcg tta gac ctg aag    1662
Glu Val Lys Lys Ala Trp Leu Arg Arg Ser Leu Ala Leu Asp Leu Lys
            410                  415                  420 cag aag gct cga gtc cac agc agt gcg gga tgt gga agt ggt tac tat    1710
Gln Lys Ala Arg Val His Ser Ser Ala Gly Cys Gly Ser Gly Tyr Tyr
    425                  430                  435 gga gga atg atg tcc cac acc aca aca cag agc gtg tgt ctt agt gtc    1758
Gly Gly Met Met Ser His Thr Thr Thr Gln Ser Val Cys Leu Ser Val
440                  445                  450                  455 agt ggt gct aaa ggc ggt cat tct ctg cac acc ata gga gcc aaa gga    1806
Ser Gly Ala Lys Gly Gly His Ser Leu His Thr Ile Gly Ala Lys Gly
                460                  465                  470 caa tcc cat cta caa cat tca gga aac tta ccc ggc tac gcg cct cag    1854
Gln Ser His Leu Gln His Ser Gly Asn Leu Pro Gly Tyr Ala Pro Gln
            475                  480                  485 gac aca gag act ttg ttt tac cca gtg gtc cca aag cag aaa gag act    1902
Asp Thr Glu Thr Leu Phe Tyr Pro Val Val Pro Lys Gln Lys Glu Thr
            490                  495                  500 cca tgc aga cag agc agc agg aat gca gag gaa agc gag cat gat ttt    1950
Pro Cys Arg Gln Ser Ser Arg Asn Ala Glu Glu Ser Glu His Asp Phe
    505                  510                  515 gag cca tat ttc gta gcg gat gag gaa cat tct gga tcc atg tct tgg    1998
Glu Pro Tyr Phe Val Ala Asp Glu Glu His Ser Gly Ser Met Ser Trp
520                  525                  530                  535 aaa gaa cta gaa acg atg ctt tgatgtaact tgctggatat tataaagtgg      2049
Lys Glu Leu Glu Thr Met Leu
                540 tgcttgctat tgtcagaagt tctaagttat aaaagcttgg tttttgccca gaatcaaaac  2109 attcaataat aattgnagct ttttatctcc aaaaaaaaaa aaa                   2152

<210> SEQ ID NO 4
<211> LENGTH: 542
<212> TYPE: PRT
<213> ORGANISM: Danio rerio

<400> SEQUENCE: 4

Met Val Ser Val Glu Val Ser Val Ala Leu Val Leu Cys Cys Val Leu
1               5                   10                  15
Met Gly Ala Arg Ala Leu Ile Asp Ser Asp Asp Val Ile Thr Arg Asp
            20                  25                  30
Glu Gln Ile Phe Leu Leu Ile Gly Ala Arg Ser Arg Cys Glu Arg Thr
        35                  40                  45
Ile Arg Ala Gln Ser Asp Val Val Arg Glu Asn Asn Cys Ala Pro Glu
    50                  55                  60
Trp Asp Gly Ile Ile Cys Trp Pro Thr Gly Lys Pro Asn Gln Met Val
65                  70                  75                  80
Ala Val Leu Cys Pro Glu Tyr Ile Tyr Asp Phe Asn His Arg Gly Tyr
                85                  90                  95
Ala Tyr Arg His Cys Asp Ala Ser Gly Asn Trp Glu Gln Val Ser Ile
            100                 105                 110
Ile Asn Arg Thr Trp Ala Asn Tyr Thr Glu Cys Thr Thr Tyr Leu His
        115                 120                 125
Thr Asn His Ser Asp Gln Glu Glu Val Phe Glu Arg Leu Tyr Leu Met
    130                 135                 140
Tyr Thr Ile Gly Tyr Ser Ile Ser Leu Ala Ala Leu Leu Val Ala Val
145                 150                 155                 160
Ser Ile Leu Cys Tyr Phe Lys Arg Leu His Cys Thr Arg Asn Tyr Ile
                165                 170                 175
His Ile His Leu Phe Thr Ser Phe Ile Cys Arg Ala Ile Ser Ile Phe
            180                 185                 190
Val Lys Asp Ala Val Leu Tyr Ala Val Thr Asn Asp Gly Glu Leu Glu
```

```
                195                 200                 205
Asp Gly Ala Val Glu Gln Arg Pro Met Val Gly Cys Lys Ala Ala Val
    210                 215                 220
Thr Leu Phe Leu Tyr Leu Leu Ala Thr Asn His Tyr Trp Ile Leu Val
225                 230                 235                 240
Glu Gly Leu Tyr Leu His Ser Leu Ile Phe Met Ala Phe Leu Ser Asp
                245                 250                 255
Lys Asn Cys Leu Trp Ala Leu Thr Ile Ile Gly Trp Gly Ile Pro Ala
            260                 265                 270
Val Phe Val Ser Ile Trp Val Ser Ala Arg Val Ser Leu Ala Asp Thr
        275                 280                 285
Gln Cys Trp Asp Ile Ser Ala Gly Asn Leu Lys Trp Ile Tyr Gln Val
    290                 295                 300
Pro Ile Leu Ala Ala Ile Val Val Asn Phe Leu Phe Leu Asn Ile
305                 310                 315                 320
Ile Arg Val Leu Ala Ser Lys Leu Trp Glu Thr Asn Thr Gly Lys Leu
                325                 330                 335
Asp Pro Arg Gln Gln Tyr Arg Lys Leu Leu Lys Ser Thr Met Val Leu
            340                 345                 350
Met Pro Leu Phe Gly Val His Tyr Met Leu Phe Met Ala Leu Pro Tyr
        355                 360                 365
Thr Asp Val Thr Gly Leu Leu Arg Gln Ile Leu Met His Tyr Glu Met
    370                 375                 380
Leu Phe Asn Ser Ser Gln Gly Phe Phe Val Ala Phe Ile Tyr Cys Phe
385                 390                 395                 400
Cys Asn Gly Glu Val Gln Ala Glu Val Lys Lys Ala Trp Leu Arg Arg
                405                 410                 415
Ser Leu Ala Leu Asp Leu Lys Gln Lys Ala Arg Val His Ser Ser Ala
            420                 425                 430
Gly Cys Gly Ser Gly Tyr Tyr Gly Gly Met Met Ser His Thr Thr Thr
        435                 440                 445
Gln Ser Val Cys Leu Ser Val Ser Gly Ala Lys Gly Gly His Ser Leu
    450                 455                 460
His Thr Ile Gly Ala Lys Gly Gln Ser His Leu Gln His Ser Gly Asn
465                 470                 475                 480
Leu Pro Gly Tyr Ala Pro Gln Asp Thr Glu Thr Leu Phe Tyr Pro Val
                485                 490                 495
Val Pro Lys Gln Lys Glu Thr Pro Cys Arg Gln Ser Ser Arg Asn Ala
            500                 505                 510
Glu Glu Ser Glu His Asp Phe Glu Pro Tyr Phe Val Ala Asp Glu Glu
        515                 520                 525
His Ser Gly Ser Met Ser Trp Lys Glu Leu Glu Thr Met Leu
    530                 535                 540

<210> SEQ ID NO 5
<211> LENGTH: 575
<212> TYPE: PRT
<213> ORGANISM: Danio rerio

<400> SEQUENCE: 5

Met Leu Thr Val Ser Leu Leu Ile Leu Cys Lys Pro Ser Ser Ser Pro
 1               5                  10                  15

Ser Pro Val Lys Ile Ile Pro Val Asp Asp Leu Pro Ala Thr Ala Glu
                20                  25                  30

Leu Arg Ala Ser Val Leu Arg Val Ser Leu Pro Lys Thr Phe Ile Lys
            35                  40                  45

Ser Phe Leu Asn His Leu Leu Gln Ala Gly Glu Asp Gly Glu Ile Thr
        50                  55                  60

Ala Glu Glu Gln Val Gln Met Leu Leu Asp Ala Lys Leu Gln Cys Leu
    65                  70                  75                  80

Gln Lys Val Ser Ser Asp Asp Pro Ala Val Gly Val Cys Val Pro Glu
                85                  90                  95

Trp Asp Gly Leu Ile Cys Trp Pro Gln Gly Phe Pro Gly Thr Leu Thr
                100                 105                 110

Lys Thr Pro Cys Pro Gly Tyr Ile Tyr Asp Phe Asn His Ala Ala His
            115                 120                 125

Ala Tyr Arg Arg Cys Asp Ser Asn Gly Ser Ser Val Leu Ala Glu Ser
        130                 135                 140
```

-continued

```
Ser Asn Lys Thr Trp Val Asn Tyr Thr Glu Cys Ile Lys Ser Pro Glu
145                 150                 155                 160

Pro Asn Lys Lys Arg Gln Val Phe Phe Glu Arg Leu His Ile Met Tyr
                165                 170                 175

Thr Val Gly Tyr Ala Val Ser Phe Ser Ser Leu Leu Val Ala Ile Phe
            180                 185                 190

Ile Ile Gly Tyr Phe Arg Arg Leu His Cys Thr Arg Asn Tyr Ile His
        195                 200                 205

Met His Leu Phe Val Ser Phe Met Leu Arg Ala Ala Ser Ile Phe Val
    210                 215                 220

Lys Asp His Val Val His Thr Ser Ala Gly Leu Gln Glu Ser Asp Ala
225                 230                 235                 240

Val Leu Met Asn Asn Phe Thr Asn Ala Val Asp Val Ala Pro Val Asp
                245                 250                 255

Thr Ser Gln Tyr Met Gly Cys Lys Val Thr Val Leu Leu Phe Ile Tyr
            260                 265                 270

Phe Leu Ala Thr Asn Tyr Tyr Trp Ile Leu Val Glu Gly Leu Tyr Leu
        275                 280                 285

His Ser Leu Ile Phe Met Ala Phe Leu Ser Asp Ser Lys Tyr Leu Trp
    290                 295                 300

Gly Phe Thr Leu Ile Gly Trp Gly Val Pro Ala Val Phe Val Ala Ala
305                 310                 315                 320

Trp Ala Val Val Arg Ala Thr Leu Ala Asp Ala Arg Cys Trp Glu Leu
                325                 330                 335

Ser Ala Gly Asn Ile Lys Trp Ile Tyr Gln Glu Pro Ile Leu Thr Ala
            340                 345                 350

Ile Gly Leu Asn Phe Ile Leu Phe Val Asn Ile Val Arg Val Leu Ala
        355                 360                 365

Thr Lys Ile Arg Glu Thr Asn Gly Gly Arg Tyr Asp Thr Arg Lys Gln
370                 375                 380

Tyr Arg Lys Leu Ala Lys Ser Thr Gln Val Leu Val Phe Val Phe Gly
385                 390                 395                 400

Val His Tyr Ile Val Phe Val Gly Met Pro His Thr Phe Glu Gly Leu
                405                 410                 415

Gly Trp Glu Glu Arg Met Tyr Cys Glu Leu Phe Phe Asn Ser Phe Gln
            420                 425                 430

Gly Phe Phe Val Ser Ile Ile Tyr Cys Tyr Cys Asn Gly Glu Val Gln
        435                 440                 445

Thr Glu Ile Lys Lys Thr Trp Thr Arg Trp Asn Leu Ala Phe Asp Trp
    450                 455                 460

Lys Gly Pro Val Val Cys Gly Ser Asn Arg Tyr Gly Ser Val Leu Thr
465                 470                 475                 480

Gly Leu Asn Asn Ser Thr Ser Ser Gln Ser Gln Leu Ala Ala Gly Gly
                485                 490                 495

Pro Gly Thr Arg Ser Thr Thr Leu Phe Ser Ser Arg Val Tyr Arg Ser
            500                 505                 510

Ser Gly Gly Pro Thr Val Ser Thr His Ala Thr Leu Pro Gly Tyr Val
        515                 520                 525

Leu Asn Ser Asp Ala Asp Ser Leu Pro Pro Ser Ile Pro Glu Glu Pro
    530                 535                 540

Glu Asp Ser Ala Lys Gln Val Asp Asp Ile Leu Leu Lys Glu Ser Leu
545                 550                 555                 560

Pro Thr Arg Pro Ser Ser Gly Leu Glu Asp Asp Glu Glu Thr Leu
```

```
<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: DNA Primer
<220> FEATURE:
<221> NAME/KEY: modified_base
<222> LOCATION: (12)..(12)
<223> OTHER INFORMATION: i

<400> SEQUENCE: 6
gtsytbrtgc cncthytygg                                               20

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: DNA Primer

<400> SEQUENCE: 7
ctcdccattr cagwarcagt adat                                          24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: DNA Primer

<400> SEQUENCE: 8
gtadatratd gmmacaaara adcc                                          24

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: DNA Primer

<400> SEQUENCE: 9
gcatttcata atgcatctgg atttg                                         25

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: DNA Primer

<400> SEQUENCE: 10
ctgtgaagaa ttgaagagca tctc                                          24

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: DNA Primer

<400> SEQUENCE: 11
acmaactact aytggatyct ggtg                                          24
```

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: DNA Primer

<400> SEQUENCE: 12
agaaacttct gtgtaaggca tcgc                                            24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: DNA Primer

<400> SEQUENCE: 13
aagagccatg aacagcatgt aatg                                            24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: DNA Primer

<400> SEQUENCE: 14
gaagactatg tagtgaacac cgaa                                            24

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: DNA Primer

<400> SEQUENCE: 15
atattgttgt ctggtgtcac atct                                            24

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 16
cgcatttgtt tctcgaagtt ttgttgc                                         27

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: DNA Primer

<400> SEQUENCE: 17
atcttcatga ccttcttctc agac                                            24

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: DNA Primer -continued

```
<400> SEQUENCE: 18
aggaagtacc tctggggctt ca                                              22

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: DNA Primer

<400> SEQUENCE: 19
gaagaggtgg atgtggatgt agtt                                            24

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: DNA Primer

<400> SEQUENCE: 20
gcagtggaga cgtttgaaat a                                               21

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: DNA Primer

<400> SEQUENCE: 21
ccagttacct gatgcatcac agtg                                            24

<210> SEQ ID NO 22
<211> LENGTH: 34
<212> TYPE: PRT
<213> ORGANISM: rat
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (21)..(21)
<223> OTHER INFORMATION: Nle

<400> SEQUENCE: 22

Ala Val Ser Glu Ile Gln Leu Xaa His Asn Leu Gly Lys His Leu Ala
 1               5                  10                  15

Ser Val Glu Arg Xaa Gln Trp Leu Arg Lys Lys Leu Gln Asp Val His
                20                  25                  30

Asn Tyr

<210> SEQ ID NO 23
<211> LENGTH: 36
<212> TYPE: PRT
<213> ORGANISM: Homo sapiens

<400> SEQUENCE: 23

Ala Val Ser Glu His Gln Leu Leu His Asp Lys Gly Lys Ser Ile Gln
 1               5                  10                  15

Asp Leu Arg Arg Arg Phe Phe Leu His His Leu Ile Ala Glu Ile His
                20                  25                  30

Thr Ala Glu Tyr
```

```
<210> SEQ ID NO 24
<211> LENGTH: 34
<212> TYPE: PRT
<213> ORGANISM: Homo sapiens

<400> SEQUENCE: 24

Ala Val Ala Glu Ile Gln Leu Met His Asn Leu Gly Lys His Leu Asn
 1               5                  10                  15

Ser Met Glu Arg Val Glu Trp Leu Arg Lys Lys Leu Gln Asp Val His
            20                  25                  30

Asp Tyr

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: DNA Primer
<220> FEATURE:
<221> NAME/KEY: modified_base
<222> LOCATION: (6)..(6)
<223> OTHER INFORMATION: i

<400> SEQUENCE: 25
ttyggngtsc aytayathgt vtt                                          23
```

What is claimed is:

1. An isolated PTH1R polypeptide selected from the group consisting of:
   (a) the amino acid sequence of the PTH1R polypeptide having the complete amino acid sequence from positions 1 to 536 in SEQ ID NO:2;
   (b) the amino acid sequence of the PTH1R polypeptide having the amino acid sequence from positions 2 to 536 in SEQ ID NO:2;
   (c) the amino acid sequence of the mature PTH1R polypeptide having the amino acid sequence from positions 25 to 536 in SEQ ID NO:2;
   (d) the amino acid sequence of the PTH1R polypeptide having the complete amino acid sequence encoded by the cDNA clone deposited with the ATCC as patent deposit PTA-916;
   (e) the amino acid sequence of the mature PTH1R polypeptide having the amino acid sequence encoded by the eDNA clone deposited with the ATCC as patent deposit PTA-916;
   (f) the amino acid sequence of the PTH1R receptor extracellular domain, said extracellular domain having the amino acid sequence from position 25 to position 147 in SEQ ID NO:2;
   (g) the amino acid sequence of the PTH1R receptor transmembrane domain, said transmembrane domain consisting of the amino acid sequence from position 148 to position 416 in SEQ ID NO:2.

2. The polypeptide of claim 1, wherein said polypeptide has the amino acid sequence of position 1 to 536 of SEQ ID NO:2.

3. The polypeptide of claim 1, wherein said polypeptide has the amino acid sequence of position 2 to 536 of SEQ ID NO:2.

4. The polypeptide of claim 1, wherein said polypeptide has the amino acid sequence of position 25 to 536 of SEQ ID NO:2.

5. The polypeptide of claim 1, wherein said polypeptide has the complete amino acid sequence encoded by the cDNA clone deposited with the ATCC as patent deposit PTA-916.

6. The polypeptide of claim 1, wherein said polypeptide has the amino acid sequence of position 25 to 147 of SEQ ID NO:2.

7. The polypeptide of claim 1, wherein said polypeptide has the amino acid sequence of position 148 to 416 of SEQ ID NO:2.

* * * * *